(12) United States Patent
Desnoyers et al.

(10) Patent No.: US 11,220,544 B2
(45) Date of Patent: Jan. 11, 2022

(54) ANTI-CD166 ANTIBODIES AND USES THEREOF

(71) Applicant: CytomX Therapeutics, Inc., South San Francisco, CA (US)

(72) Inventors: Luc Roland Desnoyers, South San Francisco, CA (US); Amy Grace DuPage, South San Francisco, CA (US)

(73) Assignee: CytomX Therapeutics, Inc., South San Francisco, CA (US)

(*) Notice: Subject to any disclaimer, the term of this patent is extended or adjusted under 35 U.S.C. 154(b) by 0 days.

(21) Appl. No.: 16/630,975

(22) PCT Filed: Jul. 13, 2018

(86) PCT No.: PCT/US2018/042074
§ 371 (c)(1),
(2) Date: Jan. 14, 2020

(87) PCT Pub. No.: WO2019/014586
PCT Pub. Date: Jan. 17, 2019

(65) Prior Publication Data
US 2020/0223919 A1  Jul. 16, 2020

Related U.S. Application Data

(60) Provisional application No. 62/532,889, filed on Jul. 14, 2017.

(51) Int. Cl.
*C07K 16/28* (2006.01)

(52) U.S. Cl.
CPC ...... *C07K 16/2803* (2013.01); *C07K 2317/24* (2013.01); *C07K 2317/515* (2013.01);
(Continued)

(58) Field of Classification Search
None
See application file for complete search history.

(56) References Cited

U.S. PATENT DOCUMENTS

| 5,998,172 A | 12/1999 | Haynes et al. |
|---|---|---|
| 6,022,540 A | 2/2000 | Bruder et al. |

(Continued)

FOREIGN PATENT DOCUMENTS

| EP | 1324771 A2 | 7/2003 |
|---|---|---|
| EP | 1523503 A1 | 4/2005 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*

(Continued)

*Primary Examiner* — Adam Weidner
(74) *Attorney, Agent, or Firm* — Fish & Richardson P.C.

(57) ABSTRACT

The present invention provides, among other things, an antibody or antigen-binding polypeptide that binds or is capable of binding CD 166, compositions including the same, and uses thereof. In certain embodiments, an anti-CD 166 antibody or antigen-binding polypeptide of the present invention binds or is capable of binding all or a portion of an intracellular domain ("ICD") of CD 166. The present invention also includes, among other things, a nucleic acid molecule encoding an antibody or antigen-binding polypeptide that binds or is capable of binding CD 166. In various embodiments, an anti-CD 166 antibody or antigen-binding polypeptide is useful in a method of detecting or treating a condition or disease.

46 Claims, 13 Drawing Sheets
Specification includes a Sequence Listing.

Prevalence of CD166 Expression Across Metastatic Indications

(52) U.S. Cl.
CPC .. *C07K 2317/565* (2013.01); *C07K 2317/622* (2013.01); *C07K 2317/76* (2013.01); *C07K 2317/92* (2013.01)

(56) References Cited

U.S. PATENT DOCUMENTS

| | | | |
|---|---|---|---|
| 7,465,790 | B2 | 12/2008 | Waldmann et al. |
| 7,582,441 | B1 | 9/2009 | Ruben et al. |
| 8,003,762 | B2 | 8/2011 | Tsukamoto |
| 8,513,390 | B2 | 8/2013 | Stagliano et al. |
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,765,133 | B2 | 7/2014 | Tsukamoto |
| 9,593,162 | B2 | 3/2017 | Liu et al. |
| 10,059,762 | B2 | 8/2018 | Stagliano et al. |
| 10,077,300 | B2 | 9/2018 | Daugherty et al. |
| 10,118,961 | B2 | 11/2018 | Stagliano et al. |
| 10,745,481 | B2 | 8/2020 | West et al. |
| 2004/0048319 | A1 | 3/2004 | Mather et al. |
| 2007/0065430 | A1* | 3/2007 | Ellis ............... A61P 25/00 424/143.1 |
| 2009/0070890 | A1 | 3/2009 | Stassar |
| 2009/0203538 | A1 | 8/2009 | Sugioka et al. |
| 2009/0269787 | A1 | 10/2009 | Tsukamoto et al. |
| 2010/0233165 | A1 | 9/2010 | Liu et al. |
| 2011/0262929 | A1 | 10/2011 | Kawai et al. |
| 2012/0149061 | A1 | 6/2012 | Stagliano et al. |
| 2012/0207756 | A1 | 8/2012 | Stagliano et al. |
| 2012/0237512 | A1 | 9/2012 | Daugherty et al. |
| 2012/0237977 | A1 | 9/2012 | Daugherty et al. |
| 2012/0244154 | A1 | 9/2012 | Daugherty et al. |
| 2013/0309230 | A1 | 11/2013 | Stagliano et al. |
| 2014/0024810 | A1 | 1/2014 | Stagliano et al. |
| 2014/0045195 | A1 | 2/2014 | Daugherty et al. |
| 2015/0071937 | A1 | 3/2015 | Liu et al. |
| 2016/0228546 | A1 | 8/2016 | Stagliano et al. |
| 2017/0081397 | A1 | 3/2017 | Stagliano et al. |
| 2017/0233488 | A1 | 8/2017 | Liu et al. |
| 2017/0362331 | A1 | 12/2017 | Lin |
| 2018/0207269 | A1 | 7/2018 | Suciu-Foca et al. |
| 2018/0320137 | A1 | 11/2018 | Valamehr et al. |
| 2019/0117789 | A1 | 4/2019 | Carman et al. |
| 2019/0119370 | A1 | 4/2019 | Stagliano et al. |
| 2019/0211089 | A1 | 7/2019 | Daugherty et al. |
| 2020/0291113 | A1 | 9/2020 | West et al. |

FOREIGN PATENT DOCUMENTS

| | | |
|---|---|---|
| EP | 1930346 B1 | 10/2011 |
| EP | 1956032 B1 | 7/2015 |
| EP | 3325006 A1 | 5/2018 |
| JP | 2009-055899 A | 3/2009 |
| WO | WO-02/030460 A2 | 4/2002 |
| WO | WO-2004/009638 A1 | 1/2004 |
| WO | WO-2008/117049 A1 | 10/2008 |
| WO | WO-2009/025846 A2 | 2/2009 |
| WO | WO-2009/039192 A2 | 3/2009 |
| WO | WO-2009/103113 A1 | 8/2009 |
| WO | WO-2010/081173 A2 | 7/2010 |
| WO | WO-2010/119704 A1 | 10/2010 |
| WO | WO 2010119704 | 10/2010 |
| WO | WO-2013/163631 A2 | 10/2013 |
| WO | WO-2013/192546 A1 | 12/2013 |
| WO | WO-2014/026136 A2 | 2/2014 |
| WO | WO-2014/107599 A2 | 7/2014 |
| WO | WO-2014/197612 A1 | 12/2014 |
| WO | WO-2016/179285 A1 | 11/2016 |
| WO | WO-2017/015227 A1 | 1/2017 |
| WO | WO-2017/078807 A1 | 5/2017 |
| WO | WO-2018/067991 A1 | 4/2018 |
| WO | WO-2018/071058 A1 | 4/2018 |
| WO | WO-2019/014586 A1 | 1/2019 |
| WO | WO-2019/046652 A1 | 3/2019 |
| WO | WO 2020/092881 | 5/2020 |

OTHER PUBLICATIONS

Kussie "A Single Engineered Amino Acid Substitution Changes Antibody Fine Specificity" J immunol 152(1):146-52 (Year: 1994).*

Koenig "Mutational landscape of antibody variable domains reveals a switch modulating the interdomain conformational dynamics and antigen binding" PNAS E486-E495 (Year: 2017).*

Boni, V. et al., CX-2009, a CD166-directed probody drug conjugate (PDC): Results from the first-in-human study in patients (Pts) with advanced cancer including breast cancer (BC), J. Clin. Oncol., 38(15 Suppl):526-526 (2020).

Carter, A. et al., Cross-species reactivity of a panel of antibodies with monkey and porcine tissue, Xenotransplantation, 6:123-130 (1999).

Chari, R. et al., Antibody-Drug Conjugates: An Emerging Concept in Cancer Therapy, Angew. Chem. Int. Ed., 53:3796-3827 (2014).

Chomet, M. et al., The tumor targeting performance of anti-CD166 Probody drug conjugate CX-2009 and its parental derivatives as monitored by 89 Zr-immune-PET in xenograft bearing mice, Theranostics, 10(13):5815-5828 (2020).

CytomX Therapeutics: CytomX Announces the First Patient Treated in Phase 1/2 PROCLAIM-CX-2009 Trial, dated Jun. 28, 2017, Retrieved from the Internet: URL:https://globenewswire.com/news-release/2017/06/28/1029952/0/en/CytomX-Announces the-First-Patient-Treated-in-Phase-1-2-PROCLAIM-CX-2009-Trial.html <URL:https://globenewswire.com/news-release/2017/06/28/1029952/0/en/CytomX-Announces%20the-First-Patient-Treated-in-Phase-1-2-PROCLAIM-CX-2009-Trial.html>.

CytomX Therapeutics: PROCLAIM-CX-2009: A Trial to Find Safe and Active Doses of an Investigational Drug CX-2009 for Patients with Selected Solid Tumors, dated Nov. 16, 2018 and marked as first posted May 11, 2017, 6 pages, Retrieved from the Internet: <URL:https://clinicaltrials.gov/ct2/show/NCT03149549>.

CytomX: Publications-CytomX, XP055664554, cited in ISR on Feb. 14, 2020 as retrieved on Feb. 3, 2020, 3 pages, Retrieved from the Internet: <URL:https://cytomx.com/probody-therapeutics/publications/>.

CytomX: Publications-CytomX, XP055664554, retrieved on Jul. 30, 20, 3 pages, Retrieved from the Internet: <URL:https://cytomx.com/probody-therapeutics/publications/>.

Erster, O. et al., Site-specific targeting of antibody activity in vivo mediated by disease-associated proteases Journal of Controlled Release, 161(3):804-812 (2012).

Garcia-Corbacho, Javier, PROCLAIM-CX-2009: A First-in-Human Trial to Evaluate CX-2009 in Adults with Metastatic or Locally Advanced Unresectable Solid Tumors, Poster ESMO 2017 Congress on Sep. 8, 2017. Retrieved from the Internet: URL: https://cytomx.com/wp-content/uploads/150103399 ESMO PROCLAIM-CX-2009-TiP_L1d_FINAL.pdf <https://cytomx.com/wp-content/uploads/150103399%20ESMO%20PROCLAIM-CX-2009-TiP_L1d_FINAL.pdf>.

Le Scolan, E. et al., Abstract 3202: A probody drug conjugate targeting CD166 (ALCAM) enhances preclinical antitumor activity of a probody therapeutic targeting PD-1, Cancer Research, 79(13 Suppl):3202, 4 pages (2019).

Le Scolan, Erwan, A ProbodyDrug Conjugate Targeting CD166 (ALCAM) Enhances Preclinical Antitumor Activity of a Probody Therapeutic Targeting PD-1, Poster, dated 2019, XP055664471; Retrieved from the Internet: URL:https://cytomx.com/wp-content/uploads/AACR_2019-PDC-Conjugate-ALCAM-Enhances-Preclinical-Antitumor-Activity.pdf<URL:https://cytomx.com/wp-content/uploads/AACR_%202019-PDC-Conjugate-ALCAM-Enhances-Preclinical-Antitumor-Activity.pdf>.

Liu, Bob, CD166-DM4 Probody Drug Conjugate (CX-2009) Treatment of 198 Patient-derived Xenograft Models (PDX) in a Mouse Clinical Trial Format, Poster, dated 2019, XP055664465, Retrieved from the Internet: URL: <https://cytomx.com/wp-content/ulpoads/AACR-2019-PDC-Conjugate-CX-2009-PDX.pdf>.

(56) References Cited

OTHER PUBLICATIONS

Meric-Bernstam, F. et al., Preliminary Results of PROCLAIM-CX-2009, a First-in-Human, Dose-Finding Study of the Probody Drug Conjugate CX-2009 in Patients with Advanced Solid Tumors, Poster, dated Mar. 29-Apr. 3, 2019, XP055664498, Retrieved from the Internet: <URL:https://cytomx.com/wp-content/uploads/AACR-2019-PROCLAIM-CX-2D09 Preliminary-Results HI-RES.pdf>.
Pauthner et al., Antibody Engineering & Therapeutics, the Annual Meeting of the Antibody Society, Dec. 7-10, 2015, San Diego, CA, USA, MABS, 8(3):617-652 (2016).
Piazza, T. et al., Internalization and recycling of ALCAM/CD166 detected by a fully human single-chain recombinant antibody, J. Cell Sci., 118(Pt7):1515-1525 (2005).
Polu, K. and Lowman, H., Probody therapeutics for targeting antibodies to diseased tissue, Expert Opin Biol Ther., 14(8):1049-1053 (2014).
Strassberger, V. et al., A comprehensive surface proteome analysis of myeloid leukemia cell lines for therapeutic antibody Development, J. Proteomics, 99:138-151 (2014).
Weaver, A. et al., Abstract C165: Development of a probody drug conjugate (PDC) against CD166 for the treatment of multiple cancers, Mol. Cancer Ther., 14(12 Supp2):1535-7163 (2015).
Wiiger, MT et al., A novel human recombinant single-chain antibody targeting CD166/ALCAM inhibits cancer cell invasion in vitro and in vivo tumour growth, Cancer Immunol. Immunother., 59(11):1665-1674 (2010).
International Search Report for PCT/US2018/042074 (ANTI-CD166 Antibodies and Uses Thereof, filed Jul. 13, 2018), issued by ISA/EP, 10 pages (dated Jan. 2, 2019).
Weaver, A. Y. et al., Development of a ProbodyTM Drug Conjugate (PDC) Targeting CD166 for the Treatment of Multiple Cancers, Retrieved from the Internet: http://cytomx.com/wp-content/uploads/2015/11/20151104_CD166_AACR_NCI_EORTC_poster_TO_PRINT_FINAL.pdf, retrieved on Jul. 26, 2016, the whole document.
Weaver, A. Y. et al., Development of a ProbodyTM Drug Conjugate (PDC) Targeting CD166 for the Treatment of Multiple Cancers, Retrieved from the Internet: <https://cytomx.com/wp-content/uploads/20151104_CD166_AACR_NCI_EORTC_poster_TO_PRINT_FINAL.pdf, retrieved on Jul. 9, 2020, the whole document.
Written Opinion for PCT/US2018/042074 (ANTI-CD166 Antibodies and Uses Thereof, filed Jul. 13, 2018), issued by ISA/EP, 12 pages (dated Jan. 2, 2019).
Search Report in Singapore Appln. No. 11202000105Q, dated Jul. 8, 2021, 8 pages.

\* cited by examiner

No Primary (media)

HCC1806

BT20

Prostate

ABCAM®
EPR2759(2)/
ab109215

Ab2

Ab1

Stomach

ABCAM®
EPR2759(2)/
ab109215

Ab2

Ab1

Liver

ABCAM®
EPR2759(2)/
ab109215

Ab2

Ab1

Spleen

ABCAM®
EPR2759(2)/
ab109215

Ab2

Ab1

Skeletal Muscle

Abcam EPR2759(2)

Ab2

Ab1

Brain

ABCAM®
EPR2759(2)/
ab109215

Ab2

Ab1

Prevalence of CD166 Expression Across Metastatic Indications

SEQUENCE LISTING

```
<160> NUMBER OF SEQ ID NOS: 72

<210> SEQ ID NO 1
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Lys Ile Asp Pro Glu Asn Gly Glu Thr Lys Tyr Ala Pro Lys Phe
    50                  55                  60

Gln Gly Lys Ala Thr Ile Thr Ala Asp Thr Ser Ser Ser Thr Ala Tyr
65                  70                  75                  80

Leu Gln Leu Ser Ser Leu Thr Ser Glu Asp Thr Ala Val Tyr Tyr Cys
                85                  90                  95

Ala Arg Glu Gly Phe Met Asp Tyr Trp Gly Gln Gly Ala Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190
```

Gln Thr Val Thr Cys Asn Val Ala His Pro Ser Ser Thr Lys Val
            195                 200                 205

Asp Lys Lys Ile Val Pro Arg Asp Cys Gly Cys Lys Pro Cys Ile Cys
210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
            245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
            275                 280                 285

Asn Ser Thr Phe Arg Ser Val Ser Glu Leu Pro Ile Met His Gln Asp
            290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
                340                 345                 350

Asp Lys Val Ser Leu Thr Cys Met Ile Thr Asp Phe Phe Pro Glu Asp
                355                 360                 365

Ile Thr Val Glu Trp Gln Trp Asn Gly Gln Pro Ala Glu Asn Tyr Lys
            370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
                420                 425                 430

Leu Ser His Ser Pro Gly Lys
            435

<210> SEQ ID NO 2
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Lys Ile Asp Pro Glu Asn Gly Glu Thr Lys Tyr Ala Pro Lys Phe
    50                  55                  60

Gln Gly Lys Ala Thr Ile Thr Ala Asp Thr Ser Ser Ser Thr Ala Tyr
65                  70                  75                  80

Leu Gln Leu Ser Ser Leu Thr Ser Glu Asp Thr Ala Val Tyr Tyr Cys
                85                  90                  95

```
Ala Arg Glu Gly Phe Met Asp Tyr Trp Gly Gln Gly Ala Ser Val Thr
            100                 105                 110

Val Ser Ser
        115

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asp Tyr Tyr Met His
1               5

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Lys Ile Asp Pro Glu Asn Gly Glu Thr Lys Tyr Ala Pro Lys Phe Gln
1               5                   10                  15

Gly

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Gly Phe Met Asp Tyr
1               5

<210> SEQ ID NO 6
<211> LENGTH: 1317
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
gaagtccagc tccaacaaag tggggcagag ctcgtgaaac tggtgcgtc cgtaaagttg      60 tcctgtacgg catctgggtt aacatcaaa gattactata tgcattgggt gaaacaacgc     120
acggagcagg ggttggaatg gattggtaaa attgaccccg aaaatggtga aacaaaatac    180
gccccgaagt ttcaaggaaa agctactata actgctgaca ctagtagctc taccgcctat    240
ttgcagctgt caagcctcac ctcagaagat acagcggtgt attattgcgc gagggaagga    300
ttcatggact actggggcca gggagcctca gtcacagtca gctctgcgaa aactacgcct    360
cccagtgtat atcctttggc ccccggctca gctgcccaga ctaatagtat ggtgactctt    420
```

```
ggctgtttgg taaaaggtta ttttcctgaa cctgtgactg tcacatggaa ttctgggtcc      480
ctgtcctccg gagtccacac gtttcctgct gtattgcaga gtgacctcta cacgctttct      540
agctccgtta cagtgccttc tagtacatgg ccctcacaga cagtaacgtg caacgtcgca      600
catccggcaa gctcaacgaa ggtagacaaa aagatagttc ccagggattg tggttgcaag      660
ccatgcatct gtacagtgcc cgaagtatct agtgtgttta ctttccccc aaaaccaaag       720 gacgtactta ctattaccct taccccaag gtcacttgtg tcgtagtaga tatatctaaa       780
gatgacccgg aagtacaatt ctcctggttc gtggatgacg tagaagttca cacggctcag      840
acacagccac gcgaggagca gttcaactct acttttagaa gcgttagtga actgccaatt      900
atgcatcagg actggctcaa cggcaaagag tttaaatgta gggtcaatag tgccgctttt      960
ccggccccca tcgagaagac tatctctaaa acgaagggcc gcccaaaagc acctcaagta     1020
tacaccatac ccccgccgaa ggaacaaatg gccaaagata aggtttcatt gacatgtatg     1080
ataaccgatt ttttcccaga agatataact gtggagtggc aatggaatgg acaacctgct     1140
gagaattaca aaaatacccca gccgatcatg gacaccgatg gaagctattt cgtgtatagc     1200
aagctcaacg tgcaaaaatc caactgggaa gctgggaaca cattcacgtg tagcgtgctc     1260
cacgaagggc ttcataatca tcacactgaa aagtccctct cccacagtcc gggcaaa       1317

<210> SEQ ID NO 7
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gaggttcagc tgcagcagtc tggggcagag cttgtgaagc caggggcctc agtcaagttg       60
tcctgcacag cttctggctt caacattaaa gactactata tgcactgggt gaagcagagg      120
actgaacagg gcctggagtg gattggaaag attgatcctg agaatggtga aactaaatat      180
gccccgaaat tccagggcaa ggccactata acagcagaca catcctccag cacagcctac      240
ctgcaactca gcagcctgac atctgaggac actgccgtct attactgtgc tagagagggt      300
tttatggact actggggtca aggagcctca gtcaccgtct cctca                     345

<210> SEQ ID NO 8
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gattactata tgcat                                                       15

<210> SEQ ID NO 9
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
```
aaaattgacc cgaaaatgg tgaaacaaaa tacgccccga agtttcaagg a  51

<210> SEQ ID NO 10
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
gaaggattca tggactac  18

<210> SEQ ID NO 11
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Phe Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 12
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 12

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Phe Val Pro Leu Thr Phe Gly Ala Gly Thr Lys Leu Glu Leu Lys
            100                 105                 110

<210> SEQ ID NO 13
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Arg Ser Ser Gln Ser Leu Val His Ser Asn Gly Asn Thr Tyr Leu His
1               5                   10                  15

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Val Ser Asn Arg Phe Ser
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Gln Ser Thr Phe Val Pro Leu Thr
1               5

<210> SEQ ID NO 16
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

```
gatgtagtaa tgacgcagac gccactttcc cttccagtgt ctctcggaga tcaggcttca      60
ataagttgcc ggtctagtca atccctcgtt cattccaacg ggaataccta tttgcattgg     120
tatctccaga aacctgggca gtccccgaaa ctcctgatct acaaagtatc aaatcgattt     180
tctggagtcc ctgatcgctt ctcaggttcc ggaagcggaa cggactttac gctcaagata     240
agtcgcgttg aggccgagga cctgggtgtt tatttctgta gccaatccac gtttgtacca     300
ctcacattcg gagcaggaac gaagctggaa ctgaagaggg cggatgcggc gccgacagtt     360
tcaatctttc ctccaagttc cgagcagctt actagcggag gggcatctgt cgtgtgtttt     420
ttgaataact tttaccctaa ggatatcaat gtcaagtgga agatcgacgg gagtgaacgg     480
cagaacggcg tcctcaacag ttggacagac caagatagta aagactcaac ctatagtatg     540
agttcaacac tcacactcac taaagacgag tacgagaggc acaatagcta tacttgtgag     600
gctacacaca aaacaagtac atcacctatc gtgaaaagct tcaatcggaa cgaatgc       657
```

<210> SEQ ID NO 17
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggaa cagatttcac actcaagatc     240
agcagagtgg aggctgagga tctgggagtt tatttctgct ctcaaagtac atttgttccg     300
ctcacgttcg gtgctgggac caagctggag ctgaaa                               336
```

<210> SEQ ID NO 18
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18

```
cggtctagtc aatccctcgt tcattccaac gggaatacct atttgcat                   48
```

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19

```
aaagtatcaa atcgattttc t                                                21
```

<210> SEQ ID NO 20

```
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
agccaatcca cgtttgtacc actcaca                                              27

<210> SEQ ID NO 21
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Arg Gln Arg Thr Glu Gln Gly Leu Glu Trp Ile
        35                  40                  45

Gly Lys Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Glu Gly Phe Met Asp Tyr Trp Gly Gln Gly Thr Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Gln Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp

```
                290                 295                 300
Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Lys Glu Gln Met Ala Lys
                340                 345                 350

Asp Lys Val Ser Leu Thr Cys Met Ile Thr Asp Phe Phe Pro Glu Asp
                355                 360                 365

Ile Thr Val Glu Trp Gln Trp Asn Gly Gln Pro Ala Glu Asn Tyr Lys
370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
                420                 425                 430

Leu Ser His Ser Pro Gly Lys
                435
```

```
<210> SEQ ID NO 22
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
                20                  25                  30

Tyr Met His Trp Val Arg Gln Arg Thr Glu Gln Gly Leu Glu Trp Ile
            35                  40                  45

Gly Lys Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Glu Gly Phe Met Asp Tyr Trp Gly Gln Gly Thr Ser Val Thr
                100                 105                 110

Val Ser Ser
        115
```

```
<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Tyr Tyr Met His
1               5
```

<210> SEQ ID NO 24
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 24

Lys Ile Asp Pro Glu Asp Gly Glu Thr Lys Tyr Ala Pro Lys Phe Gln
1               5                   10                  15

Gly

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 25

Glu Gly Phe Met Asp Tyr
1               5

<210> SEQ ID NO 26
<211> LENGTH: 1317
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26
gaagtacagc tccagcagag tggagcggaa ctggtcaaac tgggggcttc cgtcaagctt      60
tcatgcaccg cctccggttt caatataaag gactactata tgcattgggt gcggcaacga     120
actgagcagg ggttggagtg gatcggcaag attgatccag aagacggtga aaccaaatat     180
gccccgaaat ttcagggtaa ggcaactatt acagcggata caagctcaaa tacagcatat     240
cttcagcttt ccagtcttac tagcgaagat acagcggtct actattgtgc tcgggagggg     300
ttcatggact actgggggca gggcacgtct gtaacagtta gctcagccaa gacaacgcca     360
ccttctgttt atcctttggc tcctgggtcc gctgctcaga cgaatagcat ggtcaccctg     420
ggttgcctgg tcaaaggcta cttccctgaa ccagtgactg ttacatggaa ttcaggctct     480
ctctcatctg gagtccacac ctttcctgca gtccttcagt cagatcttta cacattgtcc     540
tccagtgtaa cggttccttc atctacatgg cccagtcaga ctgttacctg taatgtggca     600
catccagcga gttccacgaa agtagataaa aagattgtgc cgagggactg tgggtgtaaa     660
ccatgtatct gcacagttcc agaagtgtca agcgtcttca tcttcccacc caaaccaaaa     720
gatgtattga cgataactct tacacctaag gtgacatgcg tggtagtcga catttctaaa     780
gacgacccag aggtccaatt cagttggttt gtcgatgatg tagaggtaca taccgctcaa     840
actcagccta gagaggaaca gttcaactca accttccggt cagtttctga gttgccaata     900
atgcatcaag attggctcaa cggaaaagaa tttaagtgcc gagtgaattc agcagcattt     960
ccagcaccta tagagaaaac aatcagcaaa acgaaggggc ggccgaaagc accacaggtg    1020

```
tacacgatac cacccccgaa ggaacaaatg gcgaaggata aagtgagcct cacgtgcatg    1080
ataacagact tttttcctga agatataaca gtcgaatggc agtggaatgg tcaaccagca    1140
gaaaattaca agaatacaca gccgatcatg gacactgacg gatcctactt cgtgtattca    1200
aagctcaatg tccagaaaag caactgggag gctgggaaca ctttcacgtg tagcgttttg    1260
cacgaagggc tgcataatca tcataccgaa aagtcactca gccactcccc cggcaag      1317
```

<210> SEQ ID NO 27
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27

```
gaggttcagc tgcagcagtc tggggcagag cttgtgaagc caggggcctc agtcaagttg     60
tcctgcacag cttctggctt caacattaaa gactactata tgcactgggt gaggcagagg    120
actgaacagg gcctggagtg gattggaaag attgatcctg aggatggtga aactaaatat    180
gccccgaaat tccagggcaa ggccactata acagcagaca catcctccaa cacagcctac    240
ctgcaactca gcagcctgac atctgaggac actgccgtct attactgtgc tagagagggt    300
tttatggact actggggtca aggaacctca gtcaccgtct cctca                   345
```

<210> SEQ ID NO 28
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 28

```
gactactata tgcat                                                     15
```

<210> SEQ ID NO 29
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 29

```
aagattgatc cagaagacgg tgaaaccaaa tatgccccga aatttcaggg t              51
```

<210> SEQ ID NO 30
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 30

```
gaggggttca tggactac                                                  18
```

<210> SEQ ID NO 31
<211> LENGTH: 219

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

```
Asp Asn Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 32
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

```
Asp Asn Val Met Thr Gln Thr Pro Leu Ser Leu Ser Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
```

```
                    85                  90                  95
Thr His Val Pro Leu Thr Phe Gly Ala Gly Thr Lys Leu Glu Leu Lys
            100                 105                 110
```

<210> SEQ ID NO 33
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

```
Arg Ser Ser Gln Ser Leu Val His Ser Asn Gly Asn Thr Tyr Leu His
1               5                   10                  15
```

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

```
Lys Val Ser Asn Arg Phe Ser
1               5
```

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

```
Ser Gln Ser Thr His Val Pro Leu Thr
1               5
```

<210> SEQ ID NO 36
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36

| | | |
|---|---|---|
| gataacgtaa tgacacagac accactctct tgtccgtctc cctgggcga ccaggcgagt | 60 |
| atctcctgtc ggagttctca gtctcttgtc catagtaatg gaataccta tctgcactgg | 120 |
| tatttgcaga agccaggaca atcccctaag cttttgatct ataaagtctc aaacaggttt | 180 |
| agtggtgtac cggatcgctt tagtgggagt ggaagcggga ctgactttac gctcaaaatt | 240 |
| agccgagtcg aagcagagga tcttggggtg tacttctgtt ctcagagtac gcatgttccg | 300 |
| ttgactttg gagcgggtac gaaactcgag ttgaagcggg cggatgccgc acccacagtc | 360 |
| agcatcttcc ctcctagttc cgagcagctg acgtccggtg gtgcgtccgt cgtatgtttt | 420 |
| ctcaataact tctatcctaa agatataaac gtcaaatgga agatagatgg gagcgaacga | 480 |
| cagaatgggg tgctcaactc ttggaccgat caagattcca aagactccac ttatagtatg | 540 | agctctacat tgacgctgac caaggacgag tatgagcgac acaactctta cacctgcgag    600 gcgacccata agacttcaac ttctcccatc gtgaaaagct ttaatcgaaa cgaatgc       657

<210> SEQ ID NO 37
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
gataatgtga tgacccaaac tccactctcc ctgtctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct ataaagtttc caaccgattt   180
tctggggtcc cagacaggtt cagtggcagt ggatcaggga cagatttcac actcaagatc   240
agcagagtgg aggctgagga tctgggagtt tatttctgct ctcaaagcac acatgttccg   300
ctcacgttcg gtgctgggac caagctggag ctgaaa                             336

<210> SEQ ID NO 38
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cggagttctc agtctcttgt ccatagtaat gggaataacct atctgcac                48

<210> SEQ ID NO 39
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
aaagtctcaa acaggtttag t                                              21

<210> SEQ ID NO 40
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
tctcagagta cgcatgttcc gttgact                                        27

<210> SEQ ID NO 41
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:

```
            Synthetic polypeptide"
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (109)..(109)
<223> OTHER INFORMATION: Any amino acid

<400> SEQUENCE: 41

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Xaa Gln Arg Thr Glu Gln Gly Leu Glu Trp Ile
        35                  40                  45

Gly Lys Ile Asp Pro Glu Xaa Gly Glu Thr Lys Tyr Ala Pro Lys Phe
    50                  55                  60

Gln Gly Lys Ala Thr Ile Thr Ala Asp Thr Ser Ser Xaa Thr Ala Tyr
65                  70                  75                  80

Leu Gln Leu Ser Ser Leu Thr Ser Glu Asp Thr Ala Val Tyr Tyr Cys
                85                  90                  95

Ala Arg Glu Gly Phe Met Asp Tyr Trp Gly Gln Gly Xaa Ser Val Thr
            100                 105                 110

Val Ser Ser
        115

<210> SEQ ID NO 42
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (98)..(98)
<223> OTHER INFORMATION: Any amino acid

<400> SEQUENCE: 42

Asp Xaa Val Met Thr Gln Thr Pro Leu Ser Leu Xaa Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Xaa Val Pro Leu Thr Phe Gly Ala Gly Thr Lys Leu Glu Leu Lys
            100                 105                 110
```

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Any amino acid

<400> SEQUENCE: 43

```
Lys Ile Asp Pro Glu Xaa Gly Glu Thr Lys Tyr Ala Pro Lys Phe Gln
1               5                   10                  15

Gly
```

<210> SEQ ID NO 44
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

```
Lys Ile Asp Pro Glu Asx Gly Glu Thr Lys Tyr Ala Pro Lys Phe Gln
1               5                   10                  15

Gly
```

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid

<400> SEQUENCE: 45

```
Ser Gln Ser Thr Xaa Val Pro Leu Thr
1               5
```

<210> SEQ ID NO 46
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

-continued

```
Gln Ile Thr Leu Lys Glu Ser Gly Pro Thr Leu Val Lys Pro Thr Gln
 1               5                  10                  15
Thr Leu Thr Leu Thr Cys Thr Phe Ser Gly Phe Ser Leu Ser Thr Tyr
            20                  25                  30
Gly Met Gly Val Gly Trp Ile Arg Gln Pro Pro Gly Lys Ala Leu Glu
        35                  40                  45
Trp Leu Ala Asn Ile Trp Trp Ser Glu Asp Lys His Tyr Ser Pro Ser
    50                  55                  60
Leu Lys Ser Arg Leu Thr Ile Thr Lys Asp Thr Ser Lys Asn Gln Val
65                  70                  75                  80
Val Leu Thr Ile Thr Asn Val Asp Pro Val Asp Thr Ala Thr Tyr Tyr
                85                  90                  95
Cys Val Gln Ile Asp Tyr Gly Asn Asp Tyr Ala Phe Thr Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
```

```
                       420                 425                 430

His Glu Ala Leu His Asn His Tyr Thr Gln Lys Ser Leu Ser Leu Ser
        435                 440                 445

Pro Gly Lys
    450

<210> SEQ ID NO 47
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser
        115                 120

<210> SEQ ID NO 48
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Ser Glu Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser
        115                 120
```

```
<210> SEQ ID NO 49
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Phe Ser Leu Ser Thr Tyr Gly Met Gly Val Gly
1               5                   10

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Asn Ile Trp Trp Ser Glu Asp Lys His
1               5

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ile Asp Tyr Gly Asn Asp Tyr Ala Phe Thr Tyr
1               5                   10

<210> SEQ ID NO 52
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110
```

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 53
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110

<210> SEQ ID NO 54
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile

Ser Arg Val Glu Ala Glu Asp Val Gly Val Tyr Tyr Cys Ala Gln Asn
65                  70                  75                  80

Ser Arg Val Glu Ala Glu Asp Val Gly Val Tyr Tyr Cys Ala Gln Asn
                    85                  90                  95

Leu Glu Leu Pro Tyr Thr Phe Gly Gln Gly Thr Lys Leu Glu Ile Lys
                100                 105                 110

<210> SEQ ID NO 55
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
                100                 105                 110

<210> SEQ ID NO 56
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
    50                  55                  60

Asp Arg Phe Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
                100                 105                 110

<210> SEQ ID NO 57
<211> LENGTH: 16
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 57

Arg Ser Ser Lys Ser Leu Leu His Ser Asn Gly Ile Thr Tyr Leu Tyr
1               5                   10                  15

<210> SEQ ID NO 58
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Arg Ser Ser Gln Ser Leu Leu His Ser Asn Gly Ile Thr Tyr Leu Tyr
1               5                   10                  15

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Met Ser Asn Leu Ala Ser
1               5

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gln Met Ser Asn Arg Ala Ser
1               5

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ala Gln Asn Leu Glu Leu Pro Tyr Thr
1               5

<210> SEQ ID NO 62
<211> LENGTH: 34
<212> TYPE: PRT
<213> ORGANISM: Homo sapiens

<400> SEQUENCE: 62

Tyr Met Lys Lys Ser Lys Thr Ala Ser Lys His Val Asn Lys Asp Leu
```

```
                1               5                  10                  15
Gly Asn Met Glu Glu Asn Lys Lys Leu Glu Glu Asn Asn His Lys Thr
                20                  25                  30

Glu Ala

<210> SEQ ID NO 63
<211> LENGTH: 21
<212> TYPE: PRT
<213> ORGANISM: Homo sapiens

<400> SEQUENCE: 63

Cys Tyr Met Lys Lys Ser Lys Thr Ala Ser Lys His Val Asn Lys Asp
1               5                   10                  15

Leu Gly Asn Met Glu
                20

<210> SEQ ID NO 64
<211> LENGTH: 20
<212> TYPE: PRT
<213> ORGANISM: Homo sapiens

<400> SEQUENCE: 64

Tyr Met Lys Lys Ser Lys Thr Ala Ser Lys His Val Asn Lys Asp Leu
1               5                   10                  15

Gly Asn Met Glu
                20

<210> SEQ ID NO 65
<211> LENGTH: 20
<212> TYPE: PRT
<213> ORGANISM: Homo sapiens

<400> SEQUENCE: 65

Cys Leu Gly Asn Met Glu Glu Asn Lys Lys Leu Glu Glu Asn Asn His
1               5                   10                  15

Lys Thr Glu Ala
                20

<210> SEQ ID NO 66
<211> LENGTH: 19
<212> TYPE: PRT
<213> ORGANISM: Homo sapiens

<400> SEQUENCE: 66

Leu Gly Asn Met Glu Glu Asn Lys Lys Leu Glu Glu Asn Asn His Lys
1               5                   10                  15

Thr Glu Ala

<210> SEQ ID NO 67
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (55)..(55)
<223> OTHER INFORMATION: Any amino acid
```

```
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (109)..(109)
<223> OTHER INFORMATION: Any amino acid

<400> SEQUENCE: 67

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Xaa Gln Arg Thr Glu Gln Gly Leu Glu Trp Ile
        35                  40                  45

Gly Lys Ile Asp Pro Glu Xaa Gly Glu Thr Lys Tyr Ala Pro Lys Phe
50                  55                  60

Gln Gly Lys Ala Thr Ile Thr Ala Asp Thr Ser Ser Xaa Thr Ala Tyr
65                  70                  75                  80

Leu Gln Leu Ser Ser Leu Thr Ser Glu Asp Thr Ala Val Tyr Tyr Cys
                85                  90                  95

Ala Arg Glu Gly Phe Met Asp Tyr Trp Gly Gln Gly Xaa Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Gln Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365
```

```
Ile Thr Val Glu Trp Gln Trp Asn Gly Gln Pro Ala Glu Asn Tyr Lys
    370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
                420                 425                 430

Leu Ser His Ser Pro Gly Lys
        435

<210> SEQ ID NO 68
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (98)..(98)
<223> OTHER INFORMATION: Any amino acid

<400> SEQUENCE: 68

Asp Xaa Val Met Thr Gln Thr Pro Leu Ser Leu Xaa Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Xaa Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205
```

Pro Ile Val Lys Ser Phe Asn Arg Asn Glu Cys
    210                 215

<210> SEQ ID NO 69
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
gaagtccagc tccaacaaag tggggcagag ctcgtgaaac ctggtgcgtc cgtaaagttg    60
tcctgtacgg catctgggtt taacatcaaa gattactata tgcattgggt gaaacaacgc   120
acggagcagg ggttggaatg gattggtaaa attgaccccg aaaatggtga acaaaatac    180 gccccgaagt ttcaaggaaa agctactata actgctgaca ctagtagctc taccgcctat   240
ttgcagctgt caagcctcac ctcagaagat acagcggtgt attattgcgc gagggaagga   300
ttcatggact actggggcca gggagcctca gtcacagtca gctct               345

<210> SEQ ID NO 70
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
gatgtagtaa tgacgcagac gccactttcc cttccagtgt ctctcggaga tcaggcttca    60
ataagttgcc ggtctagtca atccctcgtt cattccaacg gaataccta tttgcattgg   120 tatctccaga aacctgggca gtccccgaaa ctcctgatct acaaagtatc aaatcgattt   180
tctggagtcc ctgatcgctt tcaggttcc ggaagcggaa cggactttac gctcaagata    240
agtcgcgttg aggccgagga cctgggtgtt tatttctgta gccaatccac gtttgtacca   300
ctcacattcg gagcaggaac gaagctggaa ctgaag                         336

<210> SEQ ID NO 71
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
gaagtacagc tccagcagag tggagcggaa ctggtcaaac ctggggcttc cgtcaagctt    60
tcatgcaccg cctccggttt caatataaag gactactata tgcattgggt gcggcaacga   120
actgagcagg ggttggagtg gatcggcaag attgatccag aagacggtga aaccaaatat   180
gccccgaaat ttcagggtaa ggcaactatt acagcggata caagctcaaa tacagcatat   240
cttcagcttt ccagtcttac tagcgaagat acagcggtct actattgtgc tcgggagggg   300
ttcatggact actggggca gggcacgtct gtaacagtta gctca                345

<210> SEQ ID NO 72
<211> LENGTH: 336
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
gataacgtaa tgacacagac accactctct ttgtccgtct ccctgggcga ccaggcgagt      60
atctcctgtc ggagttctca gtctcttgtc catagtaatg ggaataccta tctgcactgg     120
tatttgcaga agccaggaca atcccctaag cttttgatct ataaagtctc aaacaggttt     180
agtggtgtac cggatcgctt tagtgggagt ggaagcggga ctgactttac gctcaaaatt     240
agccgagtcg aagcagagga tcttggggtg tacttctgtt ctcagagtac gcatgttccg     300
ttgacttttg gagcgggtac gaaactcgag ttgaag                              336
```

ANTI-CD166 ANTIBODIES AND USES THEREOF

RELATED APPLICATIONS

This application is a National Stage Entry of International Patent Application No. PCT/US18/42074, filed on Jul. 13, 2018, which claims the benefit of U.S. Provisional Application No. 62/532,889, filed Jul. 14, 2017, each tof which is herein incorporated by reference in its entirety.

BACKGROUND

CD166, also known as activated leukocyte cell adhesion molecule (ALCAM), is a type I transmembrane molecule of the immunoglobulin super family. It was first described as a CD6 ligand on leukocytes. CD166, according to some studies, can include an extracellular domain of 500 amino acids, a transmembrane domain of 22 amino acids, and a short intracellular domain of 34 amino acids. CD166, according to some studies, can have a molecular mass of 105 kDa (69 kDa after deglycosylation). An extraceullar domain of CD166 can include five immunoglobulin-like domains. The human gene encoding CD166 is located on chromosome 3 (3q13.1q13.2), is composed of 16 exons, and has a size of over 200 kb.

SUMMARY

The present invention provides, among other things, an antibody or antigen-binding polypeptide that binds or is capable of binding CD166, compositions including the same, and uses thereof. In certain embodiments, an anti-CD166 antibody or antigen-binding polypeptide of the present invention binds or is capable of binding all or a portion of an intracellular domain ("ICD") of CD166. An antibody or antigen-binding polypeptide of the present invention that binds or is capable of binding all or a portion of an intracellular domain of CD166 can be referred to as an "anti-CD166 ICD antibody or antigen-binding polypeptide." Portions thereof can be referred to accordingly, e.g., an anti-CD166 ICD CDR. The present invention also includes, among other things, a nucleic acid molecule encoding an antibody or antigen-binding polypeptide that binds or is capable of binding CD166. In various embodiments, an anti-CD166 antibody or antigen-binding polypeptide is useful in a method of detecting or treating a condition or disease.

In some embodiments, an antibody or antigen-binding polypeptide comprises a heavy chain variable domain. In some embodiments, the present disclosure provides an antibody or antigen-binding polypeptide comprises a heavy chain variable domain comprising one or more of (i) a heavy chain complementarity-determining region 1 (HCDR1) comprising an amino acid sequence that is identical to SEQ ID NO: 3 or SEQ ID NO: 23 at 3, 4, or 5 of 5 amino acid positions, (ii) a heavy chain complementarity-determining region 2 (HCDR2) comprising an amino acid sequence that is identical to SEQ ID NO: 4, SEQ ID NO: 24, SEQ ID NO: 43, or SEQ ID NO: 44 at 12, 13, 14, 15, 16, or 17 of 17 amino acid positions, and (iii) a heavy chain complementarity-determining region 3 (HCDR3) comprising an amino acid sequence that is identical to SEQ ID NO: 5 or SEQ ID NO: 25 at 4, 5, or 6 of 6 amino acid positions.

In some embodiments, a heavy chain variable domain comprises a heavy chain HCDR1 comprising or consisting of the amino acid sequence of SEQ ID NO: 3 or SEQ ID NO: 23. In some embodiments, a heavy chain variable domain comprises a heavy chain HCDR2 comprising or consisting of the amino acid sequence of SEQ ID NO: 4, SEQ ID NO: 24, SEQ ID NO: 43, or SEQ ID NO: 44. In some embodiments, a heavy chain variable domain comprises a heavy chain HCDR3 comprising or consisting of the amino acid sequence of SEQ ID NO: 5 or SEQ ID NO: 25.

In some embodiments, a heavy chain variable domain comprises an amino acid sequence having at least 90%, at least 95%, at least 97%, at least 98%, or at least 99% identity to the amino acid sequence of SEQ ID NO: 2, SEQ ID NO: 22, or SEQ ID NO: 41. In some embodiments, a heavy chain variable domain comprises or consists of an amino acid sequence of SEQ ID NO: 2, SEQ ID NO: 22, or SEQ ID NO: 41.

In some embodiments, an antibody or antigen-binding polypeptide comprises a light chain variable domain. In some embodiments, the present disclosure provides an antibody or antigen-binding polypeptide comprising a light chain variable domain comprising one or more of (i) a light chain complementarity-determining region 1 (LCDR1) comprising an amino acid sequence that is identical to SEQ ID NO: 13 or SEQ ID NO: 33 at 12, 13, 14, 15, or 16 of 16 amino acid positions, (ii) a light chain complementarity-determining region 2 (LCDR2) comprising an amino acid sequence that is identical to SEQ ID NO: 14 or SEQ ID NO: 34 at 5, 6, or 7 of 7 amino acid positions, and (iii) a light chain complementarity-determining region 3 (LCDR3) comprising an amino acid sequence that is identical to SEQ ID NO: 15, SEQ ID NO: 35, or SEQ ID NO: 45 at 7, 8, or 9 of 9 amino acid positions.

In some embodiments, a light chain variable domain comprises a light chain LCDR1 comprising or consisting of the amino acid sequence of SEQ ID NO: 13, SEQ ID NO: 33. In some embodiments, a light chain variable domain comprises a light chain LCDR2 comprising or consisting of the amino acid sequence of SEQ ID NO: 14 or SEQ ID NO: 34. In some embodiments, a light chain variable domain comprises a light chain LCDR3 comprising or consisting of the amino acid sequence of SEQ ID NO: 15, SEQ ID NO: 35, or SEQ ID NO: 45. In some embodiments, a light chain variable domain comprises an amino acid sequence having at least 90%, at least 95%, at least 97%, at least 98%, or at least 99% identity to the amino acid sequence of SEQ ID NO: 12, SEQ ID NO: 32, or SEQ ID NO: 42. In some embodiments, a light chain variable domain comprises or consists of an amino acid sequence of SEQ ID NO: 12, SEQ ID NO: 32, or SEQ ID NO: 42.

In some embodiments, an antibody or antigen-binding polypeptide specifically binds to an epitope within a C-terminal intracellular domain of CD166 (e.g., a mammalian, primate, or human CD166).

In some embodiments, an antibody or antigen-binding polypeptide specifically binds to an epitope within SEQ ID NO: 62, SEQ ID NO: 64, or SEQ ID NO: 66.

In some embodiments, an antibody or antigen-binding polypeptide specifically competes for binding to an epitope with an antibody or antigen-binding polypeptide comprising a heavy chain variable domain comprising one or more of (i) a heavy chain complementarity-determining region 1 (HCDR1) comprising an amino acid sequence that is identical to SEQ ID NO: 3 or SEQ ID NO: 23 at 3, 4, or 5 of 5 amino acid positions, (ii) a heavy chain complementarity-determining region 2 (HCDR2) comprising an amino acid sequence that is identical to SEQ ID NO: 4, SEQ ID NO: 24, SEQ ID NO: 43, or SEQ ID NO: 44 at 12, 13, 14, 15, 16, or 17 of 17 amino acid positions, and (iii) a heavy chain complementarity-determining region 3 (HCDR3) comprising an amino acid sequence that is identical to SEQ ID NO: 5 or SEQ ID NO: 25 at 4, 5, or 6 of 6 amino acid positions.

In some embodiments, an antibody or antigen-binding polypeptide specifically competes for binding to an epitope with an antibody or antigen-binding polypeptide comprising a a light chain variable domain comprising one or more of (i) a light chain complementarity-determining region 1 (LCDR1) comprising an amino acid sequence that is identical to SEQ ID NO: 13 or SEQ ID NO: 33 at 12, 13, 14, 15, or 16 of 16 amino acid positions, (ii) a light chain complementarity-determining region 2 (LCDR2) comprising an amino acid sequence that is identical to SEQ ID NO: 14 or SEQ ID NO: 34 at 5, 6, or 7 of 7 amino acid positions, and (iii) a light chain complementarity-determining region 3 (LCDR3) comprising an amino acid sequence that is identical to SEQ ID NO: 15, SEQ ID NO: 35, or SEQ ID NO: 45 at 7, 8, or 9 of 9 amino acid positions.

In some embodiments, an antibody or antigen-binding polypeptide specifically competes for binding to an epitope with an antibody or antigen-binding polypeptide comprising (I) a heavy chain variable domain comprising (i) a heavy chain complementarity-determining region 1 (HCDR1) comprising an amino acid sequence that is identical to SEQ ID NO: 3 or SEQ ID NO: 23 at 3, 4, or 5 of 5 amino acid positions, (ii) a heavy chain complementarity-determining region 2 (HCDR2) comprising an amino acid sequence that is identical to SEQ ID NO: 4, SEQ ID NO: 24, SEQ ID NO: 43, or SEQ ID NO: 44 at 12, 13, 14, 15, 16, or 17 of 17 amino acid positions, and (iii) a heavy chain complementarity-determining region 3 (HCDR3) comprising an amino acid sequence that is identical to SEQ ID NO: 5 or SEQ ID NO: 25 at 4, 5, or 6 of 6 amino acid positions, and (II) a light chain variable domain comprising (i) a light chain complementarity-determining region 1 (LCDR1) comprising an amino acid sequence that is identical to SEQ ID NO: 13 or SEQ ID NO: 33 at 12, 13, 14, 15, or 16 of 16 amino acid positions, (ii) a light chain complementarity-determining region 2 (LCDR2) comprising an amino acid sequence that is identical to SEQ ID NO: 14 or SEQ ID NO: 34 at 5, 6, or 7 of 7 amino acid positions, and (iii) a light chain complementarity-determining region 3 (LCDR3) comprising an amino acid sequence that is identical to SEQ ID NO: 15, SEQ ID NO: 35, or SEQ ID NO: 45 at 7, 8, or 9 of 9 amino acid positions.

In some embodiments, an antibody or antigen-binding polypeptide that binds with an epitope within a C-terminal intracellular domain of CD166 with a $K_D$ in a range of 100 nM to 10 pM, 50 nM to 10 pM, 50 nM to 100 pM, 50 nM to 500 pM, 50 nM to 1 nM, 25 nM to 10 pM, 25 nM to 100 pM, 25 nM to 500 pM, 25 nM to 1 nM, 10 nM to 10 pM, 10 nM to 100 pM, 10 nM to 500 pM, or 10 nM to 1 nM. In some embodiments, an antibody or antigen-binding polypeptide that binds with an epitope within SEQ ID NO: 62, SEQ ID NO: 64, or SEQ ID NO: 66 with a $K_D$ in a range of 100 nM to 10 pM, 50 nM to 10 pM, 50 nM to 100 pM, 50 nM to 500 pM, 50 nM to 1 nM, 25 nM to 10 pM, 25 nM to 100 pM, 25 nM to 500 pM, 25 nM to 1 nM, 10 nM to 10 pM, 10 nM to 100 pM, 10 nM to 500 pM, or 10 nM to 1 nM.

In some embodiments, an antibody or antigen-binding polypeptide is an IgA, IgG, IgM, IgE, or IgD antibody. In some embodiments, an IgG antibody is an IgG1, IgG2, IgG3, or IgG4 antibody.

In some embodiments, an antibody or antigen-binding polypeptide is or comprises a fusion protein.

In some embodiments, an antigen-binding polypeptide is or comprises a Fab fragment, a Fab' fragment, a F(ab')$_2$ fragment, a Fd fragment, a Fd' fragment, a Fv fragment, a dAb fragment, a scFv, an isolated HCDR region, an isolated LCDR region, a dsFv diabody, a scAb, a single domain heavy chain antibody, a single domain light chain antibody, or a single chain antibody.

In some embodiments, an antibody or antigen-binding polypeptide is a mouse antibody or antigen-binding polypeptide, a rabbit antibody or antigen-binding polypeptide, or a hamster antibody or antigen-binding polypeptide. In some embodiments, an antibody or antigen-binding polypeptide is a human or humanized antibody or antigen-binding polypeptide. In some embodiments, an antibody or antigen-binding polypeptide is a codon-optimized antibody or antigen-binding polypeptide.

In some embodiments, an antibody or antigen-binding polypeptide is chimeric or reverse chimeric.

In some embodiments, an antibody or antigen-binding polypeptide is conjugated to an agent. In some embodiments, an agent is or includes a detectable moiety or a therapeutic moiety.

In some embodiments, a detectable moiety is or comprises a label. In some embodiments, a label is or comprises biotin, an enzymatic reporter, a fluorescent label, a chemiluminescent label, an in vivo imaging agent, or a radioactive label. In some embodiments, a label is or comprises an enzymatic reporter selected from peroxidase, alkaline phosphatase (AP), glucose oxidase, or 1-galactosidase. In some embodiments, a label is or comprises a radioactive label. A radioactive label can comprise zirconium-89 (89Zr), iodine-124 (124I), iodine-131 (131I), iodine-125 (125I), bismuth-212 (212Bi), bismuth-213 (213Bi), astatine-221 (221At), copper-67 (67Cu), copper-64 (64Cu), rhenium-186 (186Re), rhenium-188 (188Re), phosphorus-32 (32P), samarium-153 (153Sm), lutetium-177 (177Lu), technetium-99m (99mTc), gallium-67 (67Ga), indium-111 (111In), or thallium-201 (201Tl).

In some embodiments, a therapeutic moiety is or comprises a drug (e.g., a cytotoxic agent, chemotherapeutic agent, toxin, or radionuclide).

Among other things, the present disclosure provides a composition comprising an antibody or antigen-binding polypeptide described herein. In some embodiments, a composition includes a pharmaceutically acceptable carrier or excipient.

In some embodiments, a composition comprises CD166 (e.g., a mammalian CD166, a primate CD166, a human CD166). In some embodiments, a composition comprises an antibody or antigen-binding polypeptide of the present disclosure bound to CD166.

In some embodiments, a composition includes a secondary antibody characterized by an ability to bind to the antibody or antigen-binding polypeptide. In some instances, a secondary antibody is conjugated to an agent, e.g., a detectable moiety. In some embodiments, a detectable moiety is or comprises biotin, an enzymatic reporter, a fluorescent label, a chemiluminescent label, an in vivo imaging agent, or a radioactive label. In some embodiments, a detectable moiety is or comprises an enzymatic reporter selected from peroxidase, alkaline phosphatase (AP), glucose oxidase, or β-galactosidase. In some embodiments, a detectable moiety is or comprises a radioactive label that comprises zirconium-89 (89Zr), iodine-124 (124I), iodine-131 (131I), iodine-125 (125I), bismuth-212 (212Bi), bismuth-213 (213Bi), astatine-221 (221At), copper-67 (67Cu), copper-64 (64Cu), rhenium-186 (186Re), rhenium-188 (188Re), phosphorus-32 (32P), samarium-153 (153Sm), lutetium-177 (177Lu), technetium-99m (99mTc), gallium-67 (67Ga), indium-111 (111In), or thallium-201 (201Tl).

In some embodiments, a composition includes a secondary antibody bound to an antibody or antigen-binding polypeptide.

The present disclosure provides a nucleic acid sequence comprising a sequence encoding a heavy chain variable domain and/or a light chain variable domain of an antibody or antigen-binding polypeptide of the present disclosure. The present disclosure additionally provides a vector comprising such a nucleic acid sequence. A host cell comprising such a nucleic acid sequence or vector is also provided. As described herein, a method of producing an antibody or antigen-binding polypeptide comprises culturing a host cell comprising a nucleic acid sequence or vector encoding a heavy chain variable domain and/or a light chain variable domain of an antibody or antigen-binding polypeptide of the present disclosure under conditions that allow the host cell to express the antibody or antigen-binding polypeptide. In some embodiments, a method comprises isolating the antibody or antigen-binding polypeptide.

The present disclosure provides a kit comprising an antibody or antigen-binding polypeptide described herein.

In some embodiments, a kit comprises a secondary antibody characterized by an ability to bind to the antibody or antigen-binding polypeptide. In some embodiments, a secondary antibody is conjugated to an agent, e.g., a detectable moiety. In some embodiments, a detectable moiety is or comprises biotin, an enzymatic reporter, a fluorescent label, a chemiluminescent label, an in vivo imaging agent, or a radioactive label. In some embodiments, a detectable moiety is or comprises an enzymatic reporter selected from peroxidase, alkaline phosphatase (AP), glucose oxidase, or β-galactosidase. In some embodiments, a detectable moiety is or comprises a radioactive label, e.g., a radioactive label that comprises zirconium-89 (89Zr), iodine-124 (124I), iodine-131 (131I), iodine-125 (125I), bismuth-212 (212Bi), bismuth-213 (213Bi), astatine-221 (221At), copper-67 (67Cu), copper-64 (64Cu), rhenium-186 (186Re), rhenium-188 (188Re), phosphorus-32 (32P), samarium-153 (153Sm), lutetium-177 (177Lu), technetium-99m (99mTc), gallium-67 (67Ga), indium-111 (111In), or thallium-201 (201Tl).

In some embodiments, a kit comprises one or more of (i) a nuclei staining reagent, (ii) a blocking buffer, (iii) a wash buffer, and a mounting medium.

In some embodiments, a kit comprises a therapeutic agent, e.g., a therapeutic antibody or antigen binding polypeptide. In some embodiments, a therapeutic antibody or antigen binding polypeptide specifically binds to an immune checkpoint protein (e.g., PD-L1 or PD-1).

In some embodiments, a therapeutic antibody or antigen binding polypeptide specifically binds to CD166. In some embodiments, a therapeutic antibody or antigen binding polypeptide is a therapeutic anti-CD166 antibody or antigen binding polypeptide comprising:

(i) a heavy chain variable domain comprising one or more of:
 (a) a heavy chain HCDR1 that is identical to SEQ ID NO: 49 at 12 of 12, 11 of 12, or 10 of 12 amino acid positions;
 (b) a heavy chain HCDR2 that is identical to SEQ ID NO: 50 at 9 of 9, 8 of 9, or 7 of 9 amino acid positions; and
 (c) a heavy chain HCDR3 that is identical to SEQ ID NO: 51 at 11 of 11, 10 of 11, or 9 of 11 amino acid positions; and/or (ii) comprising a light chain variable domain comprising one or more of:
 (a) a light chain LCDR1 that is identical to SEQ ID NO: 57 or SEQ ID NO: 58 at 16 of 16, 15 of 16, 14 of 16, or 13 of 16 amino acid positions;
 (b) a light chain LCDR2 that is identical to SEQ ID NO: 59 or SEQ ID NO: 60 at 7 of 7, 6 of 7, or 5 of 7 amino acid positions; and
 (c) a light chain LCDR3 that is identical to SEQ ID NO: 61 at 9 of 9, 8 of 9, or 7 of 9 amino acid positions.

In some embodiments, a therapeutic antibody or antigen binding polypeptide comprises a heavy chain variable domain comprising an amino acid sequence having at least 90%, at least 95%, at least 97%, at least 98%, or at least 99% identity to the amino acid sequence of SEQ ID NO: 47 or SEQ ID NO: 48. In some embodiments, a therapeutic antibody or antigen binding polypeptide comprises a heavy chain variable domain comprising or consisting of an amino acid sequence of SEQ ID NO: 47 or SEQ ID NO: 48.

In some embodiments, a therapeutic antibody or antigen binding polypeptide comprises a light chain variable domain comprising an amino acid sequence having at least 90%, at least 95%, at least 97%, at least 98%, or at least 99% identity to the amino acid sequence of SEQ ID NO: 53, SEQ ID NO: 54, SEQ ID NO: 55, or SEQ ID NO: 56. In some embodiments, a therapeutic antibody or antigen binding polypeptide comprises a light chain variable domain comprising or consisting of an amino acid sequence of SEQ ID NO: 53, SEQ ID NO: 54, SEQ ID NO: 55, or SEQ ID NO: 56.

In some embodiments, a therapeutic antibody or antigen binding polypeptide is an activatable therapeutic antibody or antigen binding polypeptide.

In some embodiments, a therapeutic antibody or antigen binding polypeptide is conjugated to an agent (e.g., a therapeutic moiety). In some embodiments, a therapeutic moiety is or comprises a drug (e.g., a cytotoxic agent, chemotherapeutic agent, toxin, or radionuclide).

In one aspect provided herein, a method of detecting CD166 in a sample comprises contacting the sample with an antibody or antigen-binding polypeptide of the present disclosure, and detecting the presence or absence of antibody or antigen-binding polypeptide binding with a portion of the sample, thereby detecting the presence or absence of CD166 (e.g., a mammalian CD166, a primate CD166, or a human CD166).

In one aspect provided herein, a method of detecting an CD166-expressing cell in a tissue sample comprises contacting the tissue sample with an antibody or antigen-binding polypeptide of the present disclosure, and detecting the presence or absence of antibody or antigen-binding polypeptide binding with at least one cell in the tissue sample, thereby detecting the presence or absence of a CD166-expressing cell in the tissue sample. In some embodiments, the CD166 expressed by the CD166-expressing cell is a mammalian CD166, a primate CD166, or a human CD166.

In one aspect provided herein, a method of detecting an activated lymphocyte or activated monocyte (leukocyte) in a tissue sample comprises contacting the tissue sample with an antibody or antigen-binding polypeptide of the present disclosure, and detecting the presence or absence of antibody or antigen-binding polypeptide binding with at least one cell in the sample, thereby detecting the presence or absence of the activated lymphocyte or the activated monocyte (leukocyte) in the tissue sample.

In some embodiments, a sample comprises cells from a tumor cell line. In some embodiments, a sample is from a subject. In some embodiments, a sample comprises cancer cells (e.g., solid tumor cells). In some embodiments, cancer cells comprise non-small cell lung cancer cells, breast cancer cells, ovarian cancer cells, endometrial cancer cells, cholangiocarcinoma cells, head and neck cancer cells, or castration-resistant prostate cancer cells. In some embodiments, cancer cells comprise H292 cells, HCC1806 cells, MDA-MB-231 cells, BXPC3 cells, HT29 cells, or BT20 cells.

In some embodiments, a sample is fixed. In some embodiments, a sample is embedded in a medium (e.g., a formalin-fixed paraffin-embedded sample).

In some embodiments, detecting the presence or absence of antibody or antigen-binding polypeptide binding with a portion of the sample comprises performing immunohistochemistry, electropherography, Western blot analysis, immunoprecipitation analysis, and/or microscopy.

In some embodiments, detecting the presence or absence of antibody or antigen-binding polypeptide binding with a portion of the sample comprises detecting a level of antibody or antigen-binding polypeptide binding with a portion of the sample, thereby detecting a level of CD166.

In some embodiments, a method includes comparing a level of antibody or antigen-binding polypeptide binding with a portion of the sample, or comparing the level of CD166 with a reference value.

The present disclosure provides a method of treating a disease or disorder comprising administering a therapeutic antibody or antigen-binding polypeptide to a subject at risk of or suffering from the disease or disorder, where prior to administration, the presence of CD166 was detected in a sample from the subject. In some embodiments, the presence of CD166 was detected in a sample from the subject by performing the steps of contacting the sample with an antibody or antigen-binding polypeptide of the present disclosure, and detecting the presence or absence of antibody or antigen-binding polypeptide binding with a portion of the sample, thereby detecting the presence or absence of CD166.

In some embodiments, detecting the presence or absence of antibody or antigen-binding polypeptide binding with a portion of the sample comprises performing immunohistochemistry, electropherography, Western blot analysis, immunoprecipitation analysis, and/or microscopy.

In some embodiments, a method comprises, subsequent to the administration, detecting the presence of CD166 in the sample from the subject. In some embodiments, detecting the presence of CD166 in the sample from the subject includes performing the steps of contacting the sample with an antibody or antigen-binding polypeptide of the present disclosure, and detecting the presence or absence of antibody or antigen-binding polypeptide binding with a portion of the sample, thereby detecting the presence or absence of CD166.

In some embodiments, detecting the presence or absence of antibody or antigen-binding polypeptide binding with a portion of the sample comprises performing immunohistochemistry, electropherography, Western blot analysis, immunoprecipitation analysis, and/or microscopy.

In some embodiments, a therapeutic antibody or antigen binding polypeptide specifically binds to an immune checkpoint protein (e.g., PD-L1 or PD-1).

In some embodiments, a therapeutic anti-CD166 antibody or antigen-binding polypeptide.

In some embodiments, a therapeutic antibody or antigen binding polypeptide is an activatable therapeutic antibody or antigen binding polypeptide.

In some embodiments, a therapeutic antibody or antigen binding polypeptide is conjugated to an agent (e.g., a therapeutic moiety).

In some embodiments, a therapeutic anti-CD166 antibody or antigen binding polypeptide comprises:

(i) a heavy chain variable domain comprising one or more of:
  (a) a heavy chain HCDR1 that is identical to SEQ ID NO: 49 at 12 of 12, 11 of 12, or 10 of 12 amino acid positions;
  (b) a heavy chain HCDR2 that is identical to SEQ ID NO: 50 at 9 of 9, 8 of 9, or 7 of 9 amino acid positions; and
  (c) a heavy chain HCDR3 that is identical to SEQ ID NO: 51 at 11 of 11, 10 of 11, or 9 of 11 amino acid positions; and/or (ii) comprising a light chain variable domain comprising one or more of:
  (a) a light chain LCDR1 that is identical to SEQ ID NO: 57 or SEQ ID NO: 58 at 16 of 16, 15 of 16, 14 of 16, or 13 of 16 amino acid positions;
  (b) a light chain LCDR2 that is identical to SEQ ID NO: 59 or SEQ ID NO: 60 at 7 of 7, 6 of 7, or 5 of 7 amino acid positions; and
  (c) a light chain LCDR3 that is identical to SEQ ID NO: 61 at 9 of 9, 8 of 9, or 7 of 9 amino acid positions.

In some embodiments, a sample comprises cancer cells. In some embodiments, a sample comprises non-small cell lung cancer cells, breast cancer cells, ovarian cancer cells, endometrial cancer cells, cholangiocarcinoma cells, head and neck cancer cells, prostate cancer cells, or castration-resistant prostate cancer cells. In some embodiments, a sample comprises cancer cells comprising H292 cells, HCC1806 cells, MDA-MB-231 cells, BXPC3 cells, HT29 cells, or BT20 cells.

In some embodiments, a sample comprises an activated lymphocyte or activated monocyte (leukocyte).

In some embodiments, a disease or disorder is a cancer. In some embodiments, a cancer is a prostate cancer, squamous cell skin cancer, breast cancer, ovarian cancer, lung adenocarcinoma, small cell lung cancer, non-small cell lung cancer, small cell cancer of the esophagus, clear cell kidney cancer, cancer of the small intestine, adenocarcinoma of the colon, papillary thyroid cancer, endometrial cancer, rectal cancer, squamous cell lung cancer, laryngeal cancer, pancreatic cancer, squamous cell cervical cancer, squamous cell esophageal cancer, liver cancer, cancer of the gastric cardia, stomach cancer, cancer of the abdominal cavity, transitional cell cancer of the bladder, melanoma, breast cancer, endometrial cancer, cholangiocarcinoma, or castration-resistant prostate cancer.

The present disclosure provides a method of aiding in the selection of a therapy for a subject at risk of or suffering from a disease or disorder comprising contacting a sample from the subject with an antibody or antigen-binding polypeptide of the present disclosure, detecting the presence or absence of antibody or antigen-binding polypeptide binding with a portion of the sample, thereby detecting the presence or absence of CD166, and recording the presence or absence of CD166 in the sample.

In some embodiments, a method comprises classifying the individual as one that could benefit from administration of a therapeutic anti-CD166 antibody or antigen-binding polypeptide if the presence of CD166 is detected in the sample.

In some embodiments, detecting the presence of antibody or antigen-binding polypeptide binding with a portion of the sample comprises performing immunohistochemistry, electropherography, Western blot analysis, immunoprecipitation analysis, and/or microscopy.

In some embodiments, detecting the presence of antibody or antigen-binding polypeptide binding with a portion of the sample comprises detecting a level of antibody or antigen-binding polypeptide binding with a portion of the sample, thereby detecting a level of CD166.

In some embodiments, a method includes comparing the level of antibody or antigen-binding polypeptide binding with a portion of the sample or the level of CD166 with a reference value.

In some embodiments, a method includes administering a therapeutic antibody or antigen binding polypeptide. In some embodiments, a therapeutic antibody or antigen binding polypeptide is a therapeutic anti-CD166 antibody or antigen binding polypeptide. In some embodiments, a therapeutic antibody or antigen binding polypeptide is an activatable anti-CD166 therapeutic antibody or antigen binding polypeptide.

In some embodiments, an antibody or antigen binding polypeptide is conjugated to an agent (e.g., a detectable moiety or a therapeutic moiety).

In some embodiments, an antibody or antigen binding polypeptide is a therapeutic anti-CD166 antibody or antigen binding polypeptide comprising:
(i) a heavy chain variable domain comprising one or more of:
  (a) a heavy chain HCDR1 that is identical to SEQ ID NO: 49 at 12 of 12, 11 of 12, or 10 of 12 amino acid positions;
  (b) a heavy chain HCDR2 that is identical to SEQ ID NO: 50 at 9 of 9, 8 of 9, or 7 of 9 amino acid positions; and
  (c) a heavy chain HCDR3 that is identical to SEQ ID NO: 51 at 11 of 11, 10 of 11, or 9 of 11 amino acid positions; and/or
(ii) comprising a light chain variable domain comprising one or more of:
  (a) a light chain LCDR1 that is identical to SEQ ID NO: 57 or SEQ ID NO: 58 at 16 of 16, 15 of 16, 14 of 16, or 13 of 16 amino acid positions;
  (b) a light chain LCDR2 that is identical to SEQ ID NO: 59 or SEQ ID NO: 60 at 7 of 7, 6 of 7, or 5 of 7 amino acid positions; and
  (c) a light chain LCDR3 that is identical to SEQ ID NO: 61 at 9 of 9, 8 of 9, or 7 of 9 amino acid positions.

In some embodiments, a sample comprises cancer cells. In some embodiments, a sample comprises non-small cell lung cancer cells, breast cancer cells, ovarian cancer cells, endometrial cancer cells, cholangiocarcinoma cells, head and neck cancer cells, prostate cancer cells, or castration-resistant prostate cancer cells. In some embodiments, a sample comprises cancer cells comprising H292 cells, HCC1806 cells, MDA-MB-231 cells, BXPC3 cells, HT29 cells, or BT20 cells.

In some embodiments, a disease or disorder is a cancer. In some embodiments, a cancer is prostate cancer, squamous cell skin cancer, breast cancer, ovarian cancer, lung adenocarcinoma, small cell lung cancer, non-small cell lung cancer, small cell cancer of the esophagus, clear cell kidney cancer, cancer of the small intestine, adenocarcinoma of the colon, papillary thyroid cancer, endometrial cancer, rectal cancer, squamous cell lung cancer, laryngeal cancer, pancreatic cancer, squamous cell cervical cancer, squamous cell esophageal cancer, liver cancer, cancer of the gastric cardia, stomach cancer, cancer of the abdominal cavity, transitional cell cancer of the bladder, melanoma, breast cancer, endometrial cancer, cholangiocarcinoma, or castration-resistant prostate cancer.

The present disclosure provides a use of an antibody or antigen-binding polypeptide as described herein for detecting CD166.

The present disclosure provides a use of an antibody or antigen-binding polypeptide as described herein for treating a disease or disorder.

The present disclosure also provides a use of an antibody or antigen-binding polypeptide as described herein for selecting a therapy for a subject at risk of or suffering from a disease or disorder. In some embodiments, a disease or disorder is cancer.

The present disclosure provides an antibody or antigen-binding polypeptide as described herein for treating a disease or disorder.

The present disclosure provides an antibody or antigen-binding polypeptide as described herein for use in the manufacture of a medicament for treating a disease or disorder. In some embodiments, a disease or disorder is cancer.

These, and other aspects encompassed by the present disclosure, are described in more detail below and in the claims.

DEFINITIONS

A or An: The articles "a" and "an" are used herein to refer to one or to more than one (i.e., to at least one) of the grammatical object of the article. By way of example, "an element" means one element or more than one element.

Affinity: As used herein, the term "affinity" refers to the characteristics of a binding interaction between a binding moiety and a target and that indicates the strength of the binding interaction. In some embodiments, the measure of affinity is expressed as a dissociation constant ($K_D$). In some embodiments, a binding moiety has a high affinity for a target (e.g., a $K_D$ of less than about $10^{-7}$ M, less than about $10^{-8}$ M, or less than about $10^{-9}$ M). In some embodiments, a binding moiety has a low affinity for a target (e.g., a $K_D$ of higher than about $10^{-7}$ M, higher than about $10^{-6}$ M, higher than about $10^{-5}$ M, or higher than about $10^{-4}$ M).

Administration: As used herein, the term "administration" refers to the administration of a composition to a subject or system, e.g., a human. Those of ordinary skill in the art will be aware of a variety of routes that may, in appropriate circumstances, be utilized for administration to a subject. For example, in some embodiments, a route of administration may be ocular, oral, parenteral, topical, etc. In some embodiments, administration may be bronchial (e.g., by bronchial instillation), buccal, dermal (e.g., topical to dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. Administration may be according to any regimen described herein or known in the art.

Agent: In general, the term "agent," as used herein, can refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. In some embodiments, an agent may be utilized in isolated or pure form. In some embodiments, an agent may be utilized in crude or impure form. In some embodiments, agents may be provided as collections or libraries, for example that may be screened to identify or characterize active agents within them. In some cases, the term "agent" may refer to a compound or entity that is or includes a polymer or a plurality of same or distinct polymers.

Amelioration: As used herein, the term "amelioration" refers to the prevention, reduction or palliation of a state, or improvement of the state of a subject. Amelioration includes, but does not require complete recovery or complete prevention of a disease, disorder or condition (e.g., radiation injury).

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses immunoglobulins of types IgA, IgG, IgE, IgD, IgM (as well as subtypes thereof). A light chains of an immunoglobulin can be a kappa light chain or lambda light chain.

Associated with: Two events or entities are "associated" with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another. In some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: As used herein, the term "binding" typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system such as a cell).

Binding Moiety: As used herein, a "binding moiety" is any molecule or part of a molecule capable of specifically binding a target, e.g., a target of interest. Binding moieties include, e.g., antibodies and antigen binding fragments thereof. As used herein, an "antigen-binding polypeptide" is any polypeptide including a binding moiety, which antigen-binding polypeptide can be, in certain non-limiting examples, an antibody or a fragment thereof. An "antigen-binding polypeptide" can be any of, without limitation, a heavy chain antibody, light chain antibody, LRR-based antibody, other protein scaffold with antibody-like properties, or other immunological binding moiety known in the art, including, e.g., a four-chain immunoglobulin, imunoadhesin, diabody, dsFv, diabody, triabody, tetrabody, minibody, maxibody, TandAb, single chain antibody, heavy chain antibody, single domain heavy chain antibody, particular HCDR, particular LCDR, heavy chain variable domain, light chain variable domain, DVD, BiTe, scFv, scAb, Fab, Fab', $Fab_2$, $Fab_3$, $F(ab')_2$, Fd, Fd', Fv or the like, or any combination thereof.

Biomarker: As used herein, the term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or include a marker for a particular disease or therapeutic outcome, or likelihood thereof. Thus, in some embodiments, a biomarker is predictive, prognostic, and/or diagnostic, of a relevant biological event or state of interest. A biomarker can be an entity of any chemical class. For example, in some embodiments, a biomarker may be or include a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc.

Cancer: As used herein, the terms "cancer," "malignancy," "neoplasm," "tumor," and "carcinoma" refer to cells that exhibit relatively abnormal, uncontrolled, and/or autonomous growth, so that they exhibit an aberrant growth phenotype characterized by a significant loss of control of cell proliferation. In some embodiments, a tumor may be or include cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers are known in the art.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil, or the like. In some embodiments, a carrier is or includes one or more solid components.

CDR-grafted antibody: As used herein, the term "CDR-grafted antibody" refers to an antibody whose amino acid sequence comprises heavy and light chain variable region sequences of a first species but in which the sequences of one or more of the CDR regions of $V_H$ and/or $V_L$ are replaced with CDR sequences of another species, such as (to provide just one example) an antibody having murine $V_H$ and $V_L$ regions in which one or more of the murine CDRs (e.g., CDR3) has been replaced with human CDR sequences. Likewise, a "CDR-grafted antibody" encompasses, as an example, an antibody having human $V_H$ and $V_L$ regions in which one or more of the human CDRs (e.g., CDR3) has been replaced with mouse CDR sequences.

Constant region: As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

Dosage form or unit dosage form: As used herein, the term "dosage form" may be used to refer to a physically discrete unit, aliquot, or amount of an agent (e.g., a therapeutic or diagnostic agent) for administration to a subject. Typically, each such unit contains a predetermined quantity of active agent, e.g., a predetermined mass or number of moles of an agent.

Epitope: As used herein, the term "epitope" includes any moiety that is specifically recognized by an antibody or antigen-binding polypeptide, or a binding moiety thereof. In some embodiments, an epitope is comprised of a plurality of chemical atoms or groups on an antigen. In some embodiments and/or antigen conformations, such chemical atoms or groups are physically near to each other in space. In various embodiments, an epitope is understood to be represented by an amino acid sequence. It is understood that an epitope represented by an amino acid sequence can, some embodiments, entail a particular conformation of indicated amino acids, e.g., a conformation adopted by indicated amino acids when present in a particular protein and/or in a particular context.

Excipient: As used herein, the term "excipient" refers to an agent that may be included in a composition, for example to provide or contribute to a desired consistency or stabilizing effect. In some embodiments, a suitable excipient can be or include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. An excipient can be a component of a composition or formulation that includes an antibody or antigen-binding polypeptide, which excipient is not an antibody or antigen-binding polypeptide.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar. Comparison or alignment of sequences and determination of percent homology between two sequences can be accomplished using a mathematical algorithm, such as BLAST (basic local alignment search tool).

Human antibody: As used herein, the term "human antibody" is intended to include antibodies having variable and constant regions generated, assembled, or derived from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), e.g., in one or more CDRs.

Humanized: As used herein, the term "humanized" can refer to an antibody or antigen-binding polypeptide having an amino acid sequence that includes $V_H$ and $V_L$ region sequences from a reference antibody raised in a non-human species (e.g., a mouse), but also includes modifications in those sequences relative to the reference antibody intended to render them more "human-like," i.e., more similar to human germline variable sequences. In some embodiments, a "humanized" antibody or antigen-binding polypeptide is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody or antigen-binding polypeptide can be a antibody or antigen-binding polypeptide in which substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody or antigen-binding polypeptide includes at least a portion of an immunoglobulin constant region (Fc), typically that of a human immunoglobulin constant region. In some embodiments, a humanized antibody or antigen-binding polypeptide contains both the light chain as well as at least the variable domain of a heavy chain. A humanized antibody or antigen-binding polypeptide can include a $C_H1$, hinge, $C_H2$, $C_H3$, and, optionally, a $C_H4$ region of a heavy chain constant region. In some embodiments, a humanized antibody or antigen-binding polypeptide only contains a humanized $V_L$ region. In some embodiments, a humanized antibody or antigen-binding polypeptide only contains a humanized $V_H$ region. In some certain embodiments, a humanized antibody or antigen-binding polypeptide contains humanized $V_H$ and $V_L$ regions.

Identity: As used herein, the term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known in the art. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences can be accomplished using a mathematical algorithm, such as BLAST (basic local alignment search tool).

"Improved," "increased," or "reduced": As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

In vitro: The term "in vitro" as used herein refers to events occurring in an artificial environment, e.g., in a test tube, reaction vessel, cell culture, etc., rather than within a multicellular organism.

In vivo: As used herein, the term "in vivo" refers to events that occur within a multi-cellular organism, such as a human or a non-human animal. In the context of cell-based systems, the term may be used to refer to events that occur within a living cell (as opposed to, for example, in vitro systems).

Isolated: as used herein, refers to a substance that (1) has been separated from at least some components with which it was associated at an earlier time or with which the substance would otherwise be associated, and/or (2) is present in a composition that is or includes a limited or defined amount or concentration of one or more known or unknown contaminants. An isolated substance, in some embodiments, can be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of other non-substance components with which the substance was associated at an earlier time, e.g., other particular components or contaminants with which the substance was previously or otherwise would be associated. In certain instances, a substance is isolated if it is present in a composition that includes a limited or reduced amount or concentration of molecules of a same or similar type. For instance, in certain instances, a nucleic acid, DNA, or RNA substance is isolated if it is present in a composition that includes a limited or reduced amount or concentration of non-substance nucleic acid, DNA, or RNA molecules. For instance, in certain instances, a polypeptide substance is isolated if it is present in a composition that includes a limited or reduced amount or concentration of non-substance polypeptide molecules. In certain embodiments, an amount can be, e.g., an amount measured relative to the amount of a desired substance present in a composition. In certain embodiments, a limited amount can be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition. In certain instances, a composition is pure or substantially pure with respect to a particular substance. In some embodiments, an isolated substance is about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components or of contaminants. In some embodiments, as will be understood by those skilled in the art, a substance may still be considered "isolated" or even "pure," after having been combined with certain other components such as, for example, one or more carriers or excipients (e.g., buffer, solvent, water, etc.); in such embodiments, percent isolation or purity of the substance is calculated without including such carriers or excipients. To give but one non-limiting example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; and/or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

$K_a$: As used herein, "$K_a$" refers to an association rate of a particular binding moiety and a target to form a binding moiety/target complex.

$K_d$: As used herein, "$K_d$" refers to a dissociation rate of a particular binding moiety/target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Moiety: Those skilled in the art will appreciate that a "moiety" is a defined chemical group or entity with a particular structure and/or or activity, as described herein.

Reference: As used herein, a "reference" entity, system, amount, set of conditions, etc., is one against which a test entity, system, amount, set of conditions, etc. is compared as described herein. For example, in some embodiments, a "reference" antibody or antigen-binding polypeptide is a control antibody or antigen-binding polypeptide, e.g., an antibody or antigen-binding polypeptide that is not described herein.

Pharmaceutically acceptable: As used herein, the term "pharmaceutically acceptable" means a molecule or composition is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or that any deleterious effect is outweighed by a benefit to the recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Risk: As used herein, the term "risk" can refer to a risk of a disease, disorder, and/or condition, meaning a likelihood that a particular individual will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from individuals comparable to a particular individual. In some embodiments, relative risk is measured as fold change, e.g., a 0, 1, 2, 3, 4, 5, 6, 7, 8, 9, 10, or more fold increase or decrease in risk.

Selective binding: As used herein, "selective binding," "selectively binds" "specific binding," or "specifically binds" refers, with respect to a binding moiety and a target, preferential association of a binding moiety to a target and not to an entity that is not the target. A certain degree of non-specific binding may occur between a binding moiety and a non-target. In some embodiments, a binding moiety selectively binds a target if binding between the binding moiety and the target is greater than 2-fold, greater than 5-fold, greater than 10-fold, or greater than 100-fold as compared with binding of the binding moiety and a non-target. In some embodiments, a binding moiety selectively binds a target if the binding affinity is less than about $10^{-5}$ M, less than about $10^{-6}$ M, less than about $10^{-7}$ M, less than about $10^{-8}$ M, or less than about $10^{-9}$ M.

Subject: The term "subject," as used herein, means any subject for whom diagnosis, prognosis, or therapy is desired. For example, a subject can be an animal, e.g., a mammal, e.g., a human or non-human primate (such as an ape, monkey, orangutan, or chimpanzee), a dog, cat, guinea pig, rabbit, rat, mouse, horse, cattle, or cow.

Target: As used herein, a "target" is any molecule specifically bound by a binding moiety of a multi-specific binding molecule. In some embodiments, a target is an epitope antigen described herein.

Therapeutic agent: As used herein, the phrase "therapeutic agent" can refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, in accordance with presence or absence of a particular biomarker, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it can be marketed for administration to humans. In some embodiments, a therapeutic agent is an agent for which a medical prescription is required for administration to humans.

Therapeutically effective amount: As used herein, the term "therapeutically effective amount" refers to an amount of a therapeutic molecule (e.g., a therapeutic antibody or antigen-binding polypeptide described herein) which confers a therapeutic effect on a treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic molecule or composition effective to treat, ameliorate, or prevent a particular condition or disease, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount can be administered in a dosing regimen that may comprise multiple unit doses. For any particular therapeutic molecule, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific therapeutic molecule employed; the duration of the treatment; and like factors as is well known in the medical arts.

Treatment: As used herein, the term "treatment" (also "treat" or "treating") refers to any administration of a therapeutic molecule (e.g., a therapeutic antibody or antigen-binding polypeptide described herein) that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Treatment regimen: Those skilled in the art will appreciate that the term "treatment regimen" can be used to refer to a single dose of or a set, schedule, or series of two or more unit doses administered individually to a subject, e.g., separately administered to a subject, e.g., over a period of time. In some embodiments, a given molecule has a recommended treatment regimen, which may involve one or more doses. In some embodiments, a treatment regimen includes a plurality of doses separated in time from other doses. In some embodiments, individual doses are separated from one another by a time period of the same length; or by time periods of at least two different lengths. In some embodiments, all doses within a treatment regimen are of the same unit dose amount. In some embodiments, different doses within a treatment regimen are of different amounts.

Vector: As used herein, the term "vector" refers to a recipient nucleic acid molecule modified to include or incorporate a provided nucleic acid sequence. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION

Figure 1:
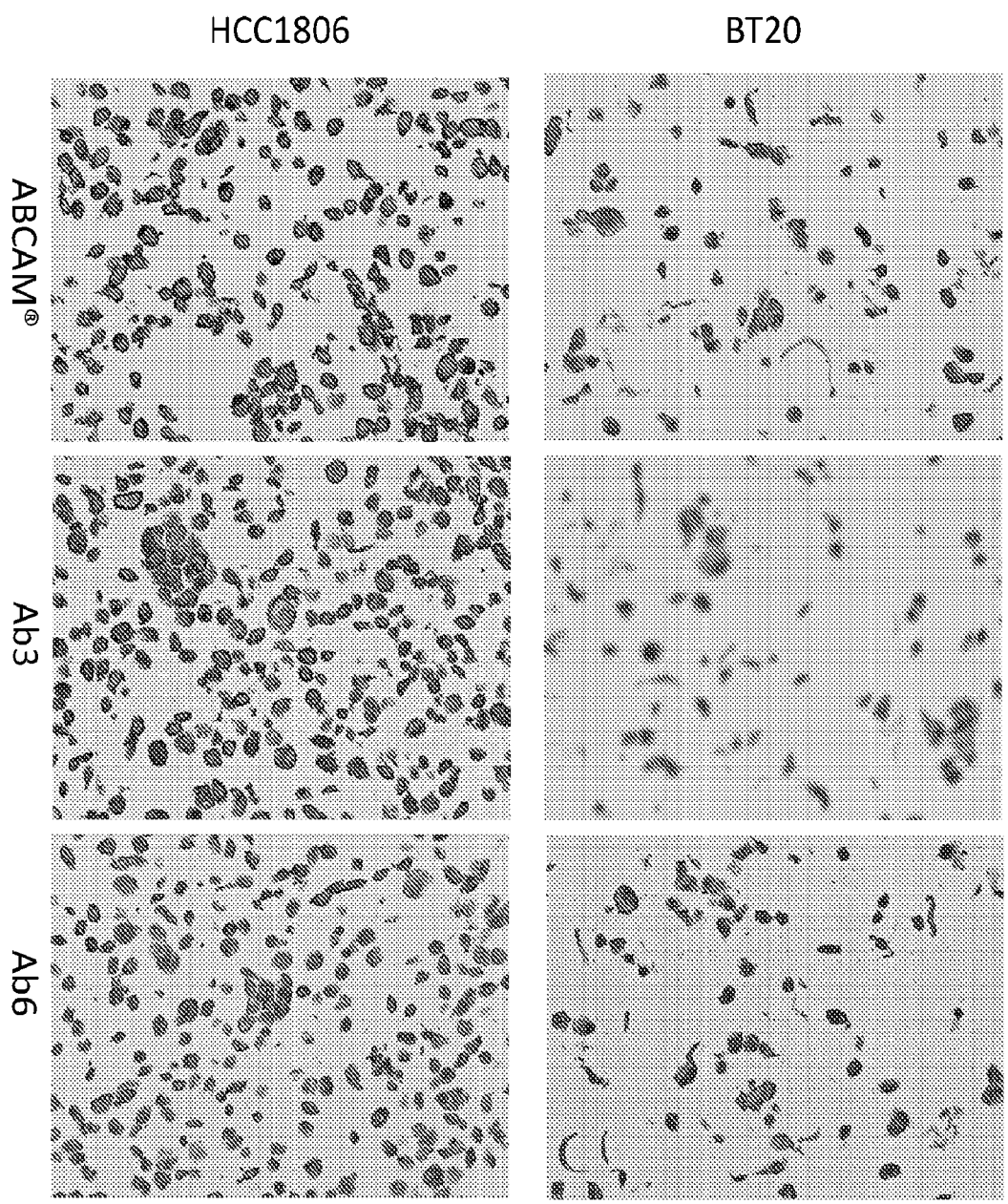
FIG. 1 is a set of immunohistochemistry (IHC) images showing formalin-fixed paraffin-embedded (FFPE) human tumor cell lines (HCC1806 and BT20), each having been prepared and blocked using standard protocols and then incubated with ABCAM® EPR2759(2)/ab109215 or supernatant of a hybridoma expressing an indicated mouse monocolonal antibody (Ab3 or Ab6).

The present invention provides, among other things, an antibody or antigen-binding polypeptide that binds or is capable of binding CD166, compositions including the same, and uses thereof. In certain embodiments, an anti-CD166 antibody or antigen-binding polypeptide of the present invention binds or is capable of binding all or a portion of an intracellular domain ("ICD") of CD166. An antibody or antigen-binding polypeptide of the present invention that binds or is capable of binding all or a portion of an intracellular domain of CD166 can be referred to as an "anti-CD166 ICD antibody or antigen-binding polypeptide." Portions thereof can be referred to accordingly, e.g., an anti-CD166 ICD CDR. The present invention also includes, among other things, a nucleic acid molecule encoding an antibody or antigen-binding polypeptide that binds or is capable of binding CD166.

In various embodiments, an anti-CD166 antibody or antigen-binding polypeptide is useful in a method of detecting or treating a condition or disease. A method of detection as disclosed herein can be in vitro, e.g., with a sample derived from a subject, or in vivo. In some instances, an anti-CD166 antibody or antigen-binding polypeptide is useful in a method of detecting or treating cancer. In some instances, an anti-CD166 antibody or antigen-binding polypeptide is useful in a method of detecting or treating a condition or disease characterized by activated lymphocytes or activated monocytes (leukocytes).

Antibodies and Antigen-Binding Polypeptides

An antibody or antigen-binding polypeptide described herein can be an immunoglobulin, heavy chain antibody, light chain antibody, LRR-based antibody, other protein scaffold with antibody-like properties, or other immunological binding moiety known in the art, including, e.g., a four-chain immunoglobulin, imunoadhesin, diabody, dsFv, diabody, triabody, tetrabody, minibody, maxibody, TandAb, single chain antibody, heavy chain antibody, single domain heavy chain antibody, particular HCDR, particular LCDR, DVD, BiTe, scFv, scAb, Fab, Fab', $Fab_2$, $Fab_3$, $F(ab')_2$, Fd, Fd', Fv or the like, or any combination thereof. The subunit structures and three-dimensional configurations of different classes of antibodies and antigen-binding polypeptides are known in the art.

An antibody can be an immunoglobulin molecule of four polypeptide chains, e.g., two heavy (H) chains and two light (L) chains. Likewise, an antigen-binding polypeptide can be or include one or more of a heavy chain, light chain, heavy chain variable domain, light chain variable domain, or any of one or more portions thereof as described herein or otherwise known in the art. A heavy chain can include a heavy chain variable domain and a heavy chain constant domain. A heavy chain constant domain can include CH1, hinge, CH2, CH3, and in some instances CH4 regions. A light chain can include a light chain variable domain and a light chain constant domain. A light chain constant domain can include a CL. A heavy chain variable domain of a heavy chain and a light chain variable domain of a light chain can typically be further subdivided into regions of variability, termed complementarity determining regions (CDRs), interspersed with regions that are more conserved, termed framework regions (FR). Such heavy chain and light chain variable domains can each include three CDRs and four framework regions, arranged from amino-terminus to carboxyl-terminus in the following order: FR1, CDR1, FR2, CDR2, FR3, CDR3, FR4, one or more of which can have a sequence as described herein. Certain heavy chain regions can be designated as HFR1, HCDR1, HFR2, HCDR2, HFR3, HCDR3, HFR4. Certain light chain regions can be designated as LFR1, LCDR1, LFR2, LCDR2, LFR3, LCDR3, LFR4.

Certain systems have been established in the art for defining CDR boundaries (e.g., the Kabat system and the Chothia system). Those of skill in the art will be aware that selection of a CDR identifying system (e.g., the Kabat system or Chothia system) will impact the amino acid sequence of identified CDRs (and accordingly the sequences of CDR-encoding nucleic acids). Thus, the skilled artisan will appreciate that while the present disclosure may identify CDRs according to a particular system, the present disclosure encompasses those CDRs as may be identified by any alternative system.

Anti-CD166 ICD Heavy Chain Complementary Determining Regions

In some embodiments, an anti-CD166 ICD antibody or antigen-binding polypeptide described herein can include one or more of an anti-CD166 ICD HCDR1, an anti-CD166 ICD HCDR2, and/or an anti-CD166 ICD HCDR3.

An anti-CD166 ICD HCDR1 of an anti-CD166 ICD antibody or antigen-binding polypeptide can have a sequence according to SEQ ID NO: 3 or SEQ ID NO: 23.

In particular instances, an anti-CD166 ICD HCDR1 of an anti-CD166 ICD antibody or antigen-binding polypeptide can have a sequence that, upon alignment with a sequence according to SEQ ID NO: 3 or a sequence according to SEQ ID NO: 23 (each of which is a sequence of 5 amino acids), is the same as the sequence according to SEQ ID NO: 3 or SEQ ID NO: 23 at 5 of 5, 4 of 5, or 3 of 5 amino acid positions.

In particular instances, an anti-CD166 ICD HCDR1 of an anti-CD166 ICD antibody or antigen-binding polypeptide can have a sequence that, upon alignment with a sequence according to SEQ ID NO: 3 or a sequence according to SEQ ID NO: 23, differs from the sequence according to SEQ ID NO: 3 or SEQ ID NO: 23 at 1 or 2, amino acid positions.

An anti-CD166 ICD HCDR2 of an anti-CD166 ICD antibody or antigen-binding polypeptide can have a sequence according to SEQ ID NO: 4, SEQ ID NO: 24, SEQ ID NO: 43, and/or SEQ ID NO: 44.

In particular instances, an anti-CD166 ICD HCDR2 of an anti-CD166 ICD antibody or antigen-binding polypeptide can have a sequence that, upon alignment with a sequence according to SEQ ID NO: 4, a sequence according to SEQ ID NO: 24, a sequence according to SEQ ID NO: 43, or a sequence according to SEQ ID NO: 44 (each of which is a sequence of 17 amino acids), is the same as the sequence according to SEQ ID NO: 4, SEQ ID NO: 24, SEQ ID NO: 43, or SEQ ID NO: 44 at 17 of 17, 16 of 17, 15 of 17, 14 of 17, 13 of 17, or 12 of 17 amino acid positions.

In particular instances, an anti-CD166 ICD HCDR2 of an anti-CD166 ICD antibody or antigen-binding polypeptide can have a sequence that, upon alignment with a sequence according to SEQ ID NO: 4, a sequence according to SEQ ID NO: 24, a sequence according to SEQ ID NO: 43, or a sequence according to SEQ ID NO: 44, differs from the sequence according to SEQ ID NO: 4, SEQ ID NO: 24, SEQ ID NO: 43, or SEQ ID NO: 44 at 1, 2, 3, 4, or 5 amino acid positions.

An anti-CD166 ICD HCDR3 of an anti-CD166 ICD antibody or antigen-binding polypeptide can have a sequence according to SEQ ID NO: 5 or SEQ ID NO: 25.

In particular instances, an anti-CD166 ICD HCDR3 of an anti-CD166 ICD antibody or antigen-binding polypeptide can have a sequence that, upon alignment with a sequence according to SEQ ID NO: 5 or a sequence according to SEQ ID NO: 25 (each of which is a sequence of 6 amino acids), is the same as a sequence according to SEQ ID NO: 5 or SEQ ID NO: 25 at 6 of 6, 5 of 6, or 4 of 6 amino acid positions.

In particular instances, an anti-CD166 ICD HCDR3 of an anti-CD166 ICD antibody or antigen-binding polypeptide can have a sequence that, upon alignment with a sequence according to SEQ ID NO: 5 or a sequence according to SEQ ID NO: 25, differs from the sequence according to SEQ ID NO: 5 or SEQ ID NO: 25 at 1 or 2 amino acid positions.

In various embodiments, an amino acid position can differ in that an amino acid corresponding to a particular position is substituted or deleted. In various embodiments, an amino acid position can differ in that an amino acid is added or inserted.

As will be understood by those of skill in the art, any anti-CD166 ICD HCDR sequence can be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or binding molecule of any format as disclosed herein or otherwise known in the art.

Anti-CD166 ICD Heavy Chain Variable Domains

In some embodiments, an anti-CD166 ICD antibody or antigen-binding polypeptide described herein can include an anti-CD166 ICD heavy chain variable domain.

Anti-CD166 ICD heavy chain variable domains of the present invention can include one of, any two of, or all of an anti-CD166 ICD HCDR1, an anti-CD166 ICD HCDR2, and/or an anti-CD166 ICD HCDR3. Those of skill in the art will appreciate that, in various instances, an anti-CD166 ICD heavy chain variable domain can be identified, characterized, distinguished, or defined by the presence of a CDR or set of CDRs, optionally selected from one of, any two of, or all of an anti-CD166 ICD HCDR1, an anti-CD166 ICD HCDR2, and/or an anti-CD166 ICD HCDR3. In various embodiments, an anti-CD166 ICD heavy chain variable domain includes an anti-CD166 ICD HCDR1. In various embodiments, an anti-CD166 ICD heavy chain variable domain includes an anti-CD166 ICD HCDR2. In various embodiments, an anti-CD166 ICD heavy chain variable domain includes an anti-CD166 ICD HCDR3. In various embodiments, an anti-CD166 ICD heavy chain variable domain includes an anti-CD166 ICD HCDR1 and an anti-CD166 ICD HCDR2. In various embodiments, an anti-CD166 ICD heavy chain variable domain includes an anti-CD166 ICD HCDR1 and an anti-CD166 ICD HCDR3. In various embodiments, an anti-CD166 ICD heavy chain variable domain includes an anti-CD166 ICD HCDR2 and an anti-CD166 ICD HCDR3. In various embodiments, an anti-CD166 ICD heavy chain variable domain includes an anti-CD166 ICD HCDR1, an anti-CD166 ICD HCDR2, and an anti-CD166 ICD HCDR3.

In some embodiments, an anti-CD166 ICD antibody or antigen-binding polypeptide described herein can include an anti-CD166 ICD heavy chain variable domain according SEQ ID NO: 2, SEQ ID NO: 22, and/or SEQ ID NO: 41.

In particular instances, an anti-CD166 ICD heavy chain variable domain of an anti-CD166 ICD antibody or antigen-binding polypeptide can have a sequence at least 75% identical to a sequence according to SEQ ID NO: 2, a sequence according to SEQ ID NO: 22, or a sequence according to SEQ ID NO: 41, e.g., at least 75%, at least 80%, at least 80%, at least 90%, at least 95%, at least 96%, at least 97%, at least 98%, or at least 99% identical to a sequence according to SEQ ID NO: 2, a sequence according to SEQ ID NO: 22, or a sequence according to SEQ ID NO: 41.

In particular instances, an anti-CD166 ICD heavy chain variable domain of an anti-CD166 ICD antibody or antigen-binding polypeptide can have a sequence that, upon alignment with a sequence according to SEQ ID NO: 2, a sequence according to SEQ ID NO: 22, or a sequence according to SEQ ID NO: 41 (each of which is a sequence of 115 amino acids), is the same as the sequence according to SEQ ID NO: 2, SEQ ID NO: 22, or SEQ ID NO: 41 at 115 of 115 to at least 90 of 115 amino acid positions (e.g., at least 90, 95, 100, 105, 106, 107, 108, 109, 110, 111, 112, 113, or 114 of 115 amino acid positions).

In particular instances, an anti-CD166 ICD heavy chain variable domain of an anti-CD166 ICD antibody or antigen-binding polypeptide can have a sequence that, upon alignment with a sequence according to SEQ ID NO: 2, a sequence according to SEQ ID NO: 22, or a sequence according to SEQ ID NO: 41, differs from the sequence according to SEQ ID NO: 2, SEQ ID NO: 22, or SEQ ID NO: 41 at no more than 25 amino acid positions (e.g., no more than 1, 2, 3, 4, 5, 6, 7, 8, 9, 10, 11, 12, 13, 14, 15, 16, 17, 18, 19, 20, or 25 amino acid positions).

Anti-CD166 ICD Heavy Chains

In some embodiments, an anti-CD166 ICD antibody or antigen-binding polypeptide described herein can include an anti-CD166 ICD heavy chain.

Anti-CD166 ICD heavy chain of the present invention can include any anti-CD166 ICD heavy chain variable domain disclosed herein.

In various embodiments, an anti-CD166 ICD heavy chain constant domain can be of any class (or subclass). In various embodiments, a heavy chain constant domain can include, without limitation, an amino acid sequence of any of one or more of an IgG, IgM, IgA, IgD, or IgE, including, without limitation, subclasses such as IgG1, IgG2, IgG3, IgG4, IgA1, and IgA2. In various instances, a constant domain can include a mixture of two or more classes (or subclasses) of immunoglobulin heavy chain constant domain. For instance, an antibody or antigen-binding polypeptide can include a first portion of a constant domain that has a sequence of an immunoglobulin constant domain selected from an IgG, IgM, IgA, IgD, or IgE class constant domain and a second portion of a constant domain that has a sequence of an immunoglobulin constant domain different from the first and selected from an IgG, IgM, IgA, IgD, or IgE class constant domain. In some instances, a constant domain can include a mixture of two or more subclasses of a particular class of constant domain, e.g., a first portion of a constant domain can include a sequence of an immunoglobulin constant domain selected from an IgG1, IgG2, IgG3, or IgG4 subclass constant domain and a second portion of a constant domain can include a sequence of an immunoglobulin constant domain different from the first and selected from an IgG1, IgG2, IgG3, or IgG4 subclass constant domain. In some instances, an anti-CD166 ICD antibody or antigen-binding polypeptide includes an Fc region or Fc fragment. A heavy chain can include a constant domain present in a reference heavy chain such as a heavy chain according to SEQ ID NO: 1, SEQ ID NO: 21, and/or SEQ ID NO: 67.

In some embodiments, an anti-CD166 ICD antibody or antigen-binding polypeptide described herein can include an anti-CD166 ICD heavy chain according SEQ ID NO: 1, SEQ ID NO: 21, and/or SEQ ID NO: 67.

In particular instances, an anti-CD166 ICD heavy chain of an anti-CD166 ICD antibody or antigen-binding polypeptide can have a sequence at least 75% identical to a sequence according to SEQ ID NO: 1, a sequence according to SEQ ID NO: 21, or a sequence according to SEQ ID NO: 67, e.g., at least 75%, at least 80%, at least 80%, at least 90%, at least 95%, at least 96%, at least 97%, at least 98%, or at least 99% identical to a sequence according to SEQ ID NO: 1, a sequence according to SEQ ID NO: 21, or a sequence according to SEQ ID NO: 67.

In particular instances, an anti-CD166 ICD heavy chain of an anti-CD166 ICD antibody or antigen-binding polypeptide can have a sequence that, upon alignment with a sequence according to SEQ ID NO: 1, a sequence according to SEQ ID NO: 21, or a sequence according to SEQ ID NO: 67 (each of which is a sequence of 439 amino acids), is the same as the sequence according to SEQ ID NO: 1, SEQ ID NO: 21, or SEQ ID NO: 67 at 439 of 439 to at least 350 of 439 amino acid positions (e.g., at least 360, 370, 380, 390, 400, 410, 420, 425, 430, 431, 432, 433, 434, 435, 436, 437, or 438 or 439 amino acid positions).

In particular instances, an anti-CD166 ICD heavy chain of an anti-CD166 ICD antibody or antigen-binding polypeptide can have a sequence that, upon alignment with a sequence according to SEQ ID NO: 1, a sequence according to SEQ ID NO: 21, or a sequence according to SEQ ID NO: 67, differs from the sequence according to SEQ ID NO: 1, SEQ ID NO: 21, or SEQ ID NO: 67 at no more than 80 amino acid positions (e.g., no more than 1, 2, 3, 4, 5, 6, 7, 8, 9, 10, 11, 12, 13, 14, 15, 16, 17, 18, 19, 20, 30, 40, 50 70 or 80 amino acid positions).

Anti-CD166 ICD Light Chain Complementary Determining Regions

In some embodiments, an anti-CD166 ICD antibody or antigen-binding polypeptide described herein can include one or more of an anti-CD166 ICD LCDR1, an anti-CD166 ICD LCDR2, and/or an anti-CD166 ICD LCDR3.

An anti-CD166 ICD LCDR1 of an anti-CD166 ICD antibody or antigen-binding polypeptide can have a sequence according to SEQ ID NO: 13 or SEQ ID NO: 33.

In particular instances, an anti-CD166 ICD LCDR1 of an anti-CD166 ICD antibody or antigen-binding polypeptide can have a sequence that, upon alignment with a sequence according to SEQ ID NO: 13 or a sequence according to SEQ ID NO: 33 (each of which is a sequence of 16 amino acids), is the same as the sequence according to SEQ ID NO: 13 or SEQ ID NO: 33 at 16 of 16, 15 of 16, 14 of 16, 13 of 16, or 12 of 16 amino acid positions.

In particular instances, an anti-CD166 ICD LCDR1 of an anti-CD166 ICD antibody or antigen-binding polypeptide can have a sequence that, upon alignment with a sequence according to SEQ ID NO: 13 or a sequence according to SEQ ID NO: 33, differs from the sequence according to SEQ ID NO: 13 or SEQ ID NO: 33 at 1, 2, 3, or 4 amino acid positions.

An anti-CD166 ICD LCDR2 of an anti-CD166 ICD antibody or antigen-binding polypeptide can have a sequence according to SEQ ID NO: 14 or SEQ ID NO: 34.

In particular instances, an anti-CD166 ICD LCDR2 of an anti-CD166 ICD antibody or antigen-binding polypeptide can have a sequence that, upon alignment with a sequence according to SEQ ID NO: 14 or a sequence according to SEQ ID NO: 34 (each of which is a sequence of 7 amino acids), is the same as the sequence according to SEQ ID NO: 14 or SEQ ID NO: 34 at 7 of 7, 6 of 7, or 5 of 7 amino acid positions.

In particular instances, an anti-CD166 ICD LCDR2 of an anti-CD166 ICD antibody or antigen-binding polypeptide can have a sequence that, upon alignment with a sequence according to SEQ ID NO: 14 or a sequence according to SEQ ID NO: 34, differs from the sequence according to SEQ ID NO: 14 or SEQ ID NO: 34 at 1 or 2 amino acid positions.

An anti-CD166 ICD LCDR3 of an anti-CD166 ICD antibody or antigen-binding polypeptide can have a sequence according to SEQ ID NO: 15, SEQ ID NO: 35, and/or SEQ ID NO: 45.

In particular instances, an anti-CD166 ICD LCDR3 of an anti-CD166 ICD antibody or antigen-binding polypeptide can have a sequence that, upon alignment with a sequence according to SEQ ID NO: 15, a sequence according to SEQ ID NO: 35, or a sequence according to SEQ ID NO: 45 (each of which is a sequence of 9 amino acids), is the same as a sequence according to SEQ ID NO: 15, SEQ ID NO: 35, or SEQ ID NO: 45 at 9 of 9, 8 of 9, or 7 of 9 amino acid positions.

In particular instances, an anti-CD166 ICD LCDR3 of an anti-CD166 ICD antibody or antigen-binding polypeptide can have a sequence that, upon alignment with a sequence according to SEQ ID NO: 15, a sequence according to SEQ ID NO: 35, or a sequence according to SEQ ID NO: 45, differs from the sequence according to SEQ ID NO: 15, SEQ ID NO: 35, or SEQ ID NO: 45 at 1 or 2 amino acid positions.

As will be understood by those of skill in the art, any anti-CD166 ICD LCDR sequence can be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or binding molecule of any format as disclosed herein or otherwise known in the art.

Anti-CD166 ICD Light Chain Variable Domains

In some embodiments, an anti-CD166 ICD antibody or antigen-binding polypeptide described herein can include an anti-CD166 ICD light chain variable domain.

Anti-CD166 ICD light chain variable domains of the present invention can include one of, any two of, or all of an anti-CD166 ICD LCDR1, an anti-CD166 ICD LCDR2, and/or an anti-CD166 ICD LCDR3. Those of skill in the art will appreciate that, in various instances, an anti-CD166 ICD light chain variable domain can be identified, characterized, distinguished, or defined by the presence of a CDR or set of CDRs, optionally selected from one of, any two of, or all of an anti-CD166 ICD LCDR1, an anti-CD166 ICD LCDR2, and/or an anti-CD166 ICD LCDR3. In various embodiments, an anti-CD166 ICD light chain variable domain includes an anti-CD166 ICD LCDR1. In various embodiments, an anti-CD166 ICD light chain variable domain includes an anti-CD166 ICD LCDR2. In various embodiments, an anti-CD166 ICD light chain variable domain includes an anti-CD166 ICD LCDR3. In various embodiments, an anti-CD166 ICD light chain variable domain includes an anti-CD166 ICD LCDR1 and an anti-CD166 ICD LCDR2. In various embodiments, an anti-CD166 ICD light chain variable domain includes an anti-CD166 ICD LCDR1 and an anti-CD166 ICD LCDR3. In various embodiments, an anti-CD166 ICD light chain variable domain includes an anti-CD166 ICD LCDR2 and an anti-CD166 ICD LCDR3. In various embodiments, an anti-CD166 ICD light chain variable domain includes an anti-CD166 ICD LCDR1, an anti-CD166 ICD LCDR2, and an anti-CD166 ICD LCDR3.

In some embodiments, an anti-CD166 ICD antibody or antigen-binding polypeptide described herein can include an anti-CD166 ICD light chain variable domain according SEQ ID NO: 12, SEQ ID NO: 32, and/or SEQ ID NO: 42.

In particular instances, an anti-CD166 ICD light chain variable domain of an anti-CD166 ICD antibody or antigen-binding polypeptide can have a sequence at least 75% identical to a sequence according to SEQ ID NO: 12, a sequence according to SEQ ID NO: 32, or a sequence according to SEQ ID NO: 42, e.g., at least 75%, at least 80%, at least 80%, at least 90%, at least 95%, at least 96%, at least 97%, at least 98%, or at least 99% identical to a sequence according to SEQ ID NO: 12, a sequence according to SEQ ID NO: 32, or a sequence according to SEQ ID NO: 42.

In particular instances, an anti-CD166 ICD light chain variable domain of an anti-CD166 ICD antibody or antigen-binding polypeptide can have a sequence that, upon alignment with a sequence according to SEQ ID NO: 12, a sequence according to SEQ ID NO: 32, or a sequence according to SEQ ID NO: 42 (each of which is a sequence of 112 amino acids), is the same as a sequence according to SEQ ID NO: 12, a sequence according to SEQ ID NO: 32, or a sequence according to SEQ ID NO: 42 at 112 of 112 to at least 85 of 112 amino acid positions (e.g., at least 85, 90, 95, 100, 105, 106, 107, 108, 109, 110, 111, or 112 of 112 amino acid positions).

In particular instances, an anti-CD166 ICD light chain variable domain of an anti-CD166 ICD antibody or antigen-binding polypeptide can have a sequence that, upon alignment with a sequence according to SEQ ID NO: 12, a sequence according to SEQ ID NO: 32, or a sequence according to SEQ ID NO: 42, differs from the sequence according to SEQ ID NO: 12, SEQ ID NO: 32, or SEQ ID NO: 42 at no more than 25 amino acid positions (e.g., no more than 1, 2, 3, 4, 5, 6, 7, 8, 9, 10, 11, 12, 13, 14, 15, 16, 17, 18, 19, 20, or 25 amino acid positions).

Anti-CD166 ICD Light Chains

In some embodiments, an anti-CD166 ICD antibody or antigen-binding polypeptide described herein can include an anti-CD166 ICD light chain.

Anti-CD166 ICD light chain of the present invention can include any anti-CD166 ICD light chain variable domain disclosed herein.

In some embodiments, an anti-CD166 ICD antibody or antigen-binding polypeptide includes an anti-CD166 ICD light chain that includes any light chain constant domain, e.g., a light chain constant domain known to those of skill in the art. As those of skill in the art will be aware, a light chain constant domain can be a kappa light chain constant domain or a lambda light chain constant domain. In certain embodiments, a constant domain of a light chain as disclosed herein is a kappa light chain constant domain. In certain embodiments, a constant domain of a light chain as disclosed herein is a lambda light chain constant domain. A light chain can include a constant domain present in a reference light chain such as a light chain according to SEQ ID NO: 11, SEQ ID NO: 31, and/or SEQ ID NO: 68.

In some embodiments, an anti-CD166 ICD antibody or antigen-binding polypeptide described herein can include an anti-CD166 ICD light chain according SEQ ID NO: 11, SEQ ID NO: 31, and/or SEQ ID NO: 68.

In particular instances, an anti-CD166 ICD light chain of an anti-CD166 ICD antibody or antigen-binding polypeptide can have a sequence at least 75% identical to a sequence according to SEQ ID NO: 11, a sequence according to SEQ ID NO: 31, or a sequence according to SEQ ID NO: 68, e.g., at least 75%, at least 80%, at least 80%, at least 90%, at least 95%, at least 96%, at least 97%, at least 98%, or at least 99% identical to a sequence according to SEQ ID NO: 11, a sequence according to SEQ ID NO: 31, or a sequence according to SEQ ID NO: 68.

In particular instances, an anti-CD166 ICD light chain of an anti-CD166 ICD antibody or antigen-binding polypeptide can have a sequence that, upon alignment with a sequence according to SEQ ID NO: 11, a sequence according to SEQ ID NO: 31, or a sequence according to SEQ ID NO: 68 (each of which is a sequence of 219 amino acids), is the same as the sequence according to SEQ ID NO: 11, SEQ ID NO: 31, or SEQ ID NO: 68 at 219 of 219 to at least 175 of 219 amino acid positions (e.g., at least 175, 180, 185, 190, 195, 200, 205, 210, 211, 212, 213, 214, 215, 216, 217, 218, or 219 of 219 amino acid positions).

In particular instances, an anti-CD166 ICD light chain of an anti-CD166 ICD antibody or antigen-binding polypeptide can have a sequence that, upon alignment with a sequence according to SEQ ID NO: 11, a sequence according to SEQ ID NO: 31, or a sequence according to SEQ ID NO: 68, differs from a sequence according to SEQ ID NO: 11, a sequence according to SEQ ID NO: 31, or a sequence according to SEQ ID NO: 68 at no more than 40 amino acid positions (e.g., no more than 1, 2, 3, 4, 5, 6, 7, 8, 9, 10, 11, 12, 13, 14, 15, 16, 17, 18, 19, 20, 30, or 40 amino acid positions).

Anti-CD166 ICD Antibodies or Antigen-Binding Polypeptides

In various embodiments, an anti-CD166 ICD antibody or antigen-binding polypeptide can include an anti-CD166 ICD heavy chain, an anti-CD166 ICD heavy chain variable domain, an anti-CD166 ICD HCDR1, an anti-CD166 ICD HCDR2, and/or an anti-CD166 ICD HCDR3 as disclosed herein. An anti-CD166 ICD antibody or antigen-binding polypeptide can include one or more of an anti-CD166 ICD heavy chain, an anti-CD166 ICD heavy chain variable domain, an anti-CD166 ICD HCDR1, an anti-CD166 ICD HCDR2, and/or an anti-CD166 ICD HCDR3 as disclosed herein in any combination.

In various embodiments, an anti-CD166 ICD antibody or antigen-binding polypeptide can include an anti-CD166 ICD light chain, an anti-CD166 ICD light chain variable domain, an anti-CD166 ICD LCDR1, an anti-CD166 ICD LCDR2, and/or an anti-CD166 ICD LCDR3 as disclosed herein. An anti-CD166 ICD antibody or antigen-binding polypeptide can include one or more of an anti-CD166 ICD light chain, an anti-CD166 ICD light chain variable domain, an anti-CD166 ICD LCDR1, an anti-CD166 ICD LCDR2, and/or an anti-CD166 ICD LCDR3 as disclosed herein in any combination.

In various embodiments, an anti-CD166 ICD antibody or antigen-binding polypeptide can include one or more, or all, of an anti-CD166 ICD heavy chain, an anti-CD166 ICD heavy chain variable domain, an anti-CD166 ICD HCDR1, an anti-CD166 ICD HCDR2, and/or an anti-CD166 ICD HCDR3 as disclosed herein, together with one or more, or all, of an anti-CD166 ICD light chain, an anti-CD166 ICD light chain variable domain, an anti-CD166 ICD LCDR1, an anti-CD166 ICD LCDR2, and/or an anti-CD166 ICD LCDR3 as disclosed herein.

In certain embodiments, an anti-CD166 ICD antibody or antigen-binding polypeptide can include an anti-CD166 ICD heavy chain variable domain and an anti-CD166 ICD light chain variable domain.

In certain embodiments, an anti-CD166 ICD antibody or antigen-binding polypeptide can include an anti-CD166 ICD heavy chain and an anti-CD166 ICD light chain.

In certain embodiments, anti-CD166 ICD antibodies and antigen-binding can include one or two anti-CD166 ICD HCDR1 regions, one or two anti-CD166 ICD HCDR2 regions, and/or one or two anti-CD166 ICD HCDR3 regions. In certain embodiments, an anti-CD166 ICD antibody or antigen-binding polypeptide can include one or more of: two anti-CD166 ICD HCDR1 regions, anti-CD166 ICD HCDR2 regions, or anti-CD166 ICD HCDR3 regions, which two regions are same or different.

In certain embodiments, anti-CD166 ICD antibodies and antigen-binding can include one or two anti-CD166 ICD LCDR1 regions, one or two anti-CD166 ICD LCDR2 regions, and/or one or two anti-CD166 ICD LCDR3 regions. In certain embodiments, an anti-CD166 ICD antibody or antigen-binding polypeptide can include one or more of: two anti-CD166 ICD LCDR1 regions, anti-CD166 ICD LCDR2 regions, or anti-CD166 ICD LCDR3 regions, which two regions are same or different.

In certain embodiments, anti-CD166 ICD antibodies and antigen-binding can include one or two heavy chain variable domains and one or two light chain variable domains. In certain embodiments, an anti-CD166 ICD antibody or antigen-binding polypeptide can include a first anti-CD166 ICD heavy chain variable domain, a second anti-CD166 ICD heavy chain variable domain that is same as or different from the first anti-CD166 ICD heavy chain variable domain, and an anti-CD166 ICD light chain variable domain. In certain embodiments, an anti-CD166 ICD antibody or antigen-binding polypeptide can include a first anti-CD166 ICD light chain variable domain, a second anti-CD166 ICD light chain variable domain that is same as or different from the first anti-CD166 ICD light chain variable domain, and an anti-CD166 ICD heavy chain variable domain. In certain embodiments, an anti-CD166 ICD antibody or antigen-binding polypeptide can include a first anti-CD166 ICD heavy chain variable domain, a second anti-CD166 ICD heavy chain variable domain that is same as or different from the first anti-CD166 ICD heavy chain variable domain, a first anti-CD166 ICD light chain variable domain, and a second anti-CD166 ICD light chain variable domain that is same as or different from the first anti-CD166 ICD light chain variable domain.

In certain embodiments, anti-CD166 ICD antibodies and antigen-binding can include one or two heavy chains and one or two light chains. In certain embodiments, an anti-CD166 ICD antibody or antigen-binding polypeptide can include a first anti-CD166 ICD heavy chain, a second anti-CD166 ICD heavy chain that is same as or different from the first anti-CD166 ICD heavy chain, and an anti-CD166 ICD light chain. In certain embodiments, an anti-CD166 ICD antibody or antigen-binding polypeptide can include a first anti-CD166 ICD light chain, a second anti-CD166 ICD light chain that is same as or different from the first anti-CD166 ICD light chain, and an anti-CD166 ICD heavy chain. In certain embodiments, an anti-CD166 ICD antibody or antigen-binding polypeptide can include a first anti-CD166 ICD heavy chain, a second anti-CD166 ICD heavy chain that is same as or different from the first anti-CD166 ICD heavy chain, a first anti-CD166 ICD light chain, and a second anti-CD166 ICD light chain that is same as or different from the first anti-CD166 ICD light chain.

In certain particular embodiments, an anti-CD166 ICD antibody or antigen-binding polypeptide of the present invention includes at least one anti-CD166 ICD heavy chain according to SEQ ID NO: 1 and at least one anti-CD166 ICD light chain according to SEQ ID NO: 11. In certain particular embodiments, an anti-CD166 ICD antibody or antigen-binding polypeptide of the present invention includes two anti-CD166 ICD heavy chains according to SEQ ID NO: 1 and two anti-CD166 ICD light chains according to SEQ ID NO: 11.

In certain particular embodiments, an anti-CD166 ICD antibody or antigen-binding polypeptide of the present invention includes at least one anti-CD166 ICD heavy chain variable domain according to SEQ ID NO: 2 and at least one anti-CD166 ICD light chain variable domain according to SEQ ID NO: 12. In certain particular embodiments, an anti-CD166 ICD antibody or antigen-binding polypeptide of the present invention includes two anti-CD166 ICD heavy chain variable domains according to SEQ ID NO: 2 and two anti-CD166 ICD light chain variable domains according to SEQ ID NO: 12.

In certain particular embodiments, an anti-CD166 ICD antibody or antigen-binding polypeptide of the present invention includes one or more or all of (a) an anti-CD166 ICD HCDR1 according to SEQ ID NO: 3; (b) an anti-CD166 ICD HCDR2 according to SEQ ID NO: 4; and/or (c) an anti-CD166 ICD HCDR3 according to SEQ ID NO: 5; and one or more or all of (a) an anti-CD166 ICD LCDR1 according to SEQ ID NO: 13; (b) an anti-CD166 ICD LCDR2 according to SEQ ID NO: 14; and/or (c) an anti-CD166 ICD LCDR3 according to SEQ ID NO: 15.

In certain particular embodiments, an anti-CD166 ICD antibody or antigen-binding polypeptide of the present invention includes one or more or all of (a) two anti-CD166 ICD HCDR1 regions according to SEQ ID NO: 3; (b) two anti-CD166 ICD HCDR2 regions according to SEQ ID NO: 4; and/or (c) two anti-CD166 ICD HCDR3 regions according to SEQ ID NO: 5; and one or more or all of (a) two anti-CD166 ICD LCDR1 regions according to SEQ ID NO: 13; (b) two anti-CD166 ICD LCDR2 regions according to SEQ ID NO: 14; and/or (c) two anti-CD166 ICD LCDR3 regions according to SEQ ID NO: 15.

In certain particular embodiments, an anti-CD166 ICD antibody or antigen-binding polypeptide of the present invention includes at least one anti-CD166 ICD HCDR1 according to SEQ ID NO: 3; at least one anti-CD166 ICD LCDR1 according to SEQ ID NO: 13; at least one anti-CD166 ICD HCDR2 according to SEQ ID NO: 4; at least one anti-CD166 ICD LCDR2 according to SEQ ID NO: 14; at least one anti-CD166 ICD HCDR3 according to SEQ ID NO: 5; and at least one anti-CD166 ICD LCDR3 according to SEQ ID NO: 15.

In certain particular embodiments, an anti-CD166 ICD antibody or antigen-binding polypeptide of the present invention includes two anti-CD166 ICD HCDR1 regions according to SEQ ID NO: 3; two anti-CD166 ICD LCDR1 regions according to SEQ ID NO: 13; two anti-CD166 ICD HCDR2 regions according to SEQ ID NO: 4; two anti-CD166 ICD LCDR2 regions according to SEQ ID NO: 14; two anti-CD166 ICD HCDR3 regions according to SEQ ID NO: 5; and two anti-CD166 ICD LCDR3 regions according to SEQ ID NO: 15.

In certain particular embodiments, an anti-CD166 ICD antibody or antigen-binding polypeptide of the present invention includes one or more or all of (a) an anti-CD166 ICD HCDR1 according to SEQ ID NO: 23; (b) an anti-CD166 ICD HCDR2 according to SEQ ID NO: 24; and/or (c) an anti-CD166 ICD HCDR3 according to SEQ ID NO: 25; and one or more or all of (a) an anti-CD166 ICD LCDR1 according to SEQ ID NO: 33; (b) an anti-CD166 ICD LCDR2 according to SEQ ID NO: 34; and/or (c) an anti-CD166 ICD LCDR3 according to SEQ ID NO: 35.

In certain particular embodiments, an anti-CD166 ICD antibody or antigen-binding polypeptide of the present invention includes one or more or all of (a) two anti-CD166 ICD HCDR1 regions according to SEQ ID NO: 23; (b) two anti-CD166 ICD HCDR2 regions according to SEQ ID NO: 24; and/or (c) two anti-CD166 ICD HCDR3 regions according to SEQ ID NO: 25; and one or more or all of (a) two anti-CD166 ICD LCDR1 regions according to SEQ ID NO: 33; (b) two anti-CD166 ICD LCDR2 regions according to SEQ ID NO: 34; and/or (c) two anti-CD166 ICD LCDR3 regions according to SEQ ID NO: 35.

In certain particular embodiments, an anti-CD166 ICD antibody or antigen-binding polypeptide of the present invention includes at least one anti-CD166 ICD HCDR1 according to SEQ ID NO: 23; at least one anti-CD166 ICD LCDR1 according to SEQ ID NO: 33; at least one anti-CD166 ICD HCDR2 according to SEQ ID NO: 24; at least one anti-CD166 ICD LCDR2 according to SEQ ID NO: 34; at least one anti-CD166 ICD HCDR3 according to SEQ ID NO: 25; and at least one anti-CD166 ICD LCDR3 according to SEQ ID NO: 35.

In certain particular embodiments, an anti-CD166 ICD antibody or antigen-binding polypeptide of the present invention includes two anti-CD166 ICD HCDR1 regions according to SEQ ID NO: 23; two anti-CD166 ICD LCDR1 regions according to SEQ ID NO: 33; two anti-CD166 ICD HCDR2 regions according to SEQ ID NO: 24; two anti-CD166 ICD LCDR2 regions according to SEQ ID NO: 34; two anti-CD166 ICD HCDR3 regions according to SEQ ID NO: 25; and two anti-CD166 ICD LCDR3 regions according to SEQ ID NO: 35.

In certain particular embodiments, an anti-CD166 ICD antibody or antigen-binding polypeptide of the present invention includes at least one anti-CD166 ICD heavy chain according to SEQ ID NO: 21 and at least one anti-CD166 ICD light chain according to SEQ ID NO: 31. In certain particular embodiments, an anti-CD166 ICD antibody or antigen-binding polypeptide of the present invention includes two anti-CD166 ICD heavy chains according to SEQ ID NO: 21 and two anti-CD166 ICD light chains according to SEQ ID NO: 31.

In certain particular embodiments, an anti-CD166 ICD antibody or antigen-binding polypeptide of the present invention includes at least one anti-CD166 ICD heavy chain variable domain according to SEQ ID NO: 22 and at least one anti-CD166 ICD light chain variable domain according to SEQ ID NO: 32. In certain particular embodiments, an anti-CD166 ICD antibody or antigen-binding polypeptide of the present invention includes two anti-CD166 ICD heavy chain variable domains according to SEQ ID NO: 22 and two anti-CD166 ICD light chain variable domains according to SEQ ID NO: 32.

It is to be understood that, where present, one or more framework regions of an anti-CD166 ICD antibody or antigen-binding polypeptide can be any framework region disclosed herein or known in the art. As those of skill in the art will be aware, framework regions are typically not determinative of antigen-binding. Exemplary heavy chain framework regions of the present invention include, without limitation, those present in SEQ ID NO: 1, SEQ ID NO: 21, and/or SEQ ID NO: 67. Exemplary light chain framework regions of the present invention include, without limitation, those present in SEQ ID NO: 11, SEQ ID NO: 31, and/or SEQ ID NO: 68.

In various instances, an anti-CD166 ICD antibody or antigen-binding polypeptide is a homodimeric monoclonal antibody. In various instances, an antibody or antigen-binding polypeptide disclosed herein is a heterodimeric antibody or antigen-binding polypeptide. In various instances, an anti-CD166 ICD antibody or antigen-binding polypeptide is a human, non-human primate, mouse, rat, rabbit, hamster, goat, chicken guinea pig, horse, or sheep antibody or antigen-binding. In various instances, an anti-CD166 ICD antibody or antigen-binding polypeptide is derived from a human, non-human primate, mouse, rat, rabbit, hamster, goat, chicken guinea pig, horse, or sheep antibody or antigen-binding polypeptide. In various instances, an anti-CD166 ICD antibody or antigen-binding polypeptide includes one or more features, e.g., amino acid sequence features, characteristic of a human, non-human primate, mouse, rat, rabbit, hamster, goat, chicken guinea pig, horse, or sheep antibody or antigen-binding. In various instances, an anti-CD166 ICD antibody or antigen-binding polypeptide is a human, humanized, primatized, or chimeric.

In various instances, an antibody or antigen-binding polypeptide (e.g., an anti-CD166 ICD antibody or antigen-binding polypeptide) is or includes, e.g., a four-chain immunoglobulin, imunoadhesin, diabody, dsFv, diabody, triabody, tetrabody, minibody, maxibody, TandAb, single chain antibody, heavy chain antibody, single domain heavy chain antibody, particular HCDR, particular LCDR, DVD, BiTe, scFv, scAb, Fab, Fab', Fab$_2$, Fab$_3$, F(ab')$_2$, Fd, Fd', Fv or the like, or any combination thereof. In various instances, an anti-CD166 ICD antibody or antigen-binding polypeptide is a fusion antibody or antigen-binding polypeptide or a conjugated anti-CD166 ICD antibody or antigen-binding polypeptide, e.g., a molecule including an antibody or antigen-binding polypeptide and an agent, such as an agent that is a detectable moiety or therapeutic agent.

Antibodies or fragments can be produced by any method known in the art for synthesizing antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324;

WO 98/46645). Chimeric antibodies can be produced using methods described in, e.g., Morrison, 1985, Science 229: 1202, and humanized antibodies by methods described in, e.g., U.S. Pat. No. 6,180,370.

Nucleotide Sequences

The present disclosure includes nucleotide sequences encoding all or a portion of an anti-CD166 ICD antibody or antigen-binding polypeptide as disclosed herein. The present disclosure includes nucleotide sequences encoding all or a portion of an anti-CD166 ICD HCDR1, an anti-CD166 ICD HCDR2, an anti-CD166 ICD HCDR3, an anti-CD166 ICD LCDR1, an anti-CD166 ICD LCDR2, an anti-CD166 ICD LCDR3, an anti-CD166 ICD light chain variable domain, an anti-CD166 ICD heavy chain variable domain, an anti-CD166 ICD heavy chain, and/or an anti-CD166 ICD light chain disclosed herein.

Those of skill in the art will be aware of codons that differ in nucleobase sequence but encode a same amino acid. Those of skill in the art will be aware of codons that differ in nucleobase sequence but encode a same amino acid in the context of a biological system, such as a mammalian biological system, bacterial biological system, fungal biological system, or in vitro system. Accordingly, for at least this reason, the present disclosure includes any of a plurality of coding sequences that, in accordance with a codon code of a biological system, encodes all or a portion of an anti-CD166 ICD antibody or antigen-binding polypeptide as disclosed herein.

The present disclosure provides, among other things, a nucleic acid sequence that is or includes a nucleic acid sequence according to SEQ ID NO: 6, the sequence of which SEQ ID NO. encodes an anti-CD166 ICD heavy chain according to SEQ ID NO: 1.

The present disclosure provides, among other things, a nucleic acid sequence that is or includes a nucleic acid sequence according to SEQ ID NO: 7, the sequence of which SEQ ID NO. encodes an anti-CD166 ICD heavy chain variable domain according to SEQ ID NO: 2.

The present disclosure provides, among other things, a nucleic acid sequence that is or includes a nucleic acid sequence according to SEQ ID NO: 69, the sequence of which SEQ ID NO. encodes an anti-CD166 ICD heavy chain variable domain according to SEQ ID NO: 2.

The present disclosure provides, among other things, a nucleic acid sequence that is or includes a nucleic acid sequence according to SEQ ID NO: 8, the sequence of which SEQ ID NO. encodes an anti-CD166 ICD HCDR1 according to SEQ ID NO: 3.

The present disclosure provides, among other things, a nucleic acid sequence that is or includes a nucleic acid sequence according to SEQ ID NO: 9, the sequence of which SEQ ID NO. encodes an anti-CD166 ICD HCDR2 according to SEQ ID NO: 4.

The present disclosure provides, among other things, a nucleic acid sequence that is or includes a nucleic acid sequence according to SEQ ID NO: 10, the sequence of which SEQ ID NO. encodes an anti-CD166 ICD HCDR3 according to SEQ ID NO: 5.

The present disclosure provides, among other things, a nucleic acid sequence that is or includes a nucleic acid sequence according to SEQ ID NO: 26, the sequence of which SEQ ID NO. encodes an anti-CD166 ICD heavy chain according to SEQ ID NO: 21.

The present disclosure provides, among other things, a nucleic acid sequence that is or includes a nucleic acid sequence according to SEQ ID NO: 27, the sequence of which SEQ ID NO. encodes an anti-CD166 ICD heavy chain variable domain according to SEQ ID NO: 22.

The present disclosure provides, among other things, a nucleic acid sequence that is or includes a nucleic acid sequence according to SEQ ID NO: 71, the sequence of which SEQ ID NO. encodes an anti-CD166 ICD heavy chain variable domain according to SEQ ID NO: 22.

The present disclosure provides, among other things, a nucleic acid sequence that is or includes a nucleic acid sequence according to SEQ ID NO: 28, the sequence of which SEQ ID NO. encodes an anti-CD166 ICD HCDR1 according to SEQ ID NO: 23.

The present disclosure provides, among other things, a nucleic acid sequence that is or includes a nucleic acid sequence according to SEQ ID NO: 29, the sequence of which SEQ ID NO. encodes an anti-CD166 ICD HCDR2 according to SEQ ID NO: 24.

The present disclosure provides, among other things, a nucleic acid sequence that is or includes a nucleic acid sequence according to SEQ ID NO: 30, the sequence of which SEQ ID NO. encodes an anti-CD166 ICD HCDR3 according to SEQ ID NO: 25.

The present disclosure provides, among other things, a nucleic acid sequence according to SEQ ID NO: 16, the sequence of which SEQ ID NO. encodes an anti-CD166 ICD light chain according to SEQ ID NO: 11.

The present disclosure provides, among other things, a nucleic acid sequence according to SEQ ID NO: 17, the sequence of which SEQ ID NO. encodes an anti-CD166 ICD light chain variable domain according to SEQ ID NO: 12.

The present disclosure provides, among other things, a nucleic acid sequence according to SEQ ID NO: 70, the sequence of which SEQ ID NO. encodes an anti-CD166 ICD light chain variable domain according to SEQ ID NO: 12.

The present disclosure provides, among other things, a nucleic acid sequence according to SEQ ID NO: 18, the sequence of which SEQ ID NO. encodes an anti-CD166 ICD LCDR1 according to SEQ ID NO: 13.

The present disclosure provides, among other things, a nucleic acid sequence according to SEQ ID NO: 19, the sequence of which SEQ ID NO. encodes an anti-CD166 ICD LCDR2 according to SEQ ID NO: 14.

The present disclosure provides, among other things, a nucleic acid sequence according to SEQ ID NO: 20, the sequence of which SEQ ID NO. encodes an anti-CD166 ICD LCDR3 according to SEQ ID NO: 15.

The present disclosure provides, among other things, a nucleic acid sequence that is or includes a nucleic acid sequence according to SEQ ID NO: 36, the sequence of which SEQ ID NO. encodes an anti-CD166 ICD light chain according to SEQ ID NO: 31.

The present disclosure provides, among other things, a nucleic acid sequence that is or includes a nucleic acid sequence according to SEQ ID NO: 37, the sequence of which SEQ ID NO. encodes an anti-CD166 ICD light chain variable domain according to SEQ ID NO: 32.

The present disclosure provides, among other things, a nucleic acid sequence that is or includes a nucleic acid sequence according to SEQ ID NO: 72, the sequence of which SEQ ID NO. encodes an anti-CD166 ICD light chain variable domain according to SEQ ID NO: 32.

The present disclosure provides, among other things, a nucleic acid sequence that is or includes a nucleic acid sequence according to SEQ ID NO: 38, the sequence of which SEQ ID NO. encodes an anti-CD166 ICD LCDR1 according to SEQ ID NO: 33.

The present disclosure provides, among other things, a nucleic acid sequence that is or includes a nucleic acid sequence according to SEQ ID NO: 39, the sequence of which SEQ ID NO. encodes an anti-CD166 ICD LCDR2 according to SEQ ID NO: 34.

The present disclosure provides, among other things, a nucleic acid sequence that is or includes a nucleic acid sequence according to SEQ ID NO: 40, the sequence of which SEQ ID NO. encodes an anti-CD166 ICD LCDR3 according to SEQ ID NO: 35.

In various instances, a nucleotide sequence disclosed herein can be or be present in a vector or plasmid. In various instances, a vector or plasmid can be present in a cell In various instances, a nucleotide sequence disclosed herein can be present in the genome of a cell. In various instances, a nucleotide sequence disclosed herein can be present in the genome of a mammalian cell, bacterial cell, or fungal cell. In various instances, a nucleotide sequence disclosed herein can be present in the genome of a cell for production of an antibody, e.g. a mammalian cell for production of a an antibody.

Detectable Moieties

In various embodiments of the present invention, an anti-CD166 ICD antibody or antigen-binding polypeptide of the present invention is associated with a detectable moiety. In various instances, an anti-CD166 ICD antibody or antigen-binding polypeptide as disclosed herein can be covalently or non-covalently associated with a detectable moiety. In various instances, an anti-CD166 ICD antibody or antigen-binding polypeptide as disclosed herein can be directly or indirectly associated with a detectable moiety. In various instances, an anti-CD166 ICD antibody or antigen-binding polypeptide as disclosed herein can be associated with a detectable moiety via a linker. In various instances, an anti-CD166 ICD antibody or antigen-binding polypeptide as disclosed herein can be fused or conjugated with a detectable moiety. In various instances, an anti-CD166 ICD antibody or antigen-binding polypeptide as disclosed herein is associated with a detectable moiety via a polypeptide terminus of the anti-CD166 ICD antibody or antigen-binding polypeptide. In various instances, an anti-CD166 ICD antibody or antigen-binding polypeptide as disclosed herein is associated with a detectable moiety via a non-terminal residue of the anti-CD166 ICD antibody or antigen-binding polypeptide. In various instances, an anti-CD166 ICD antibody or antigen-binding polypeptide as disclosed herein is associated with a detectable moiety via incorporation of the detectable moiety into the molecular structure of the anti-CD166 ICD antibody or antigen-binding polypeptide. In various instances, an anti-CD166 ICD antibody or antigen-binding polypeptide as disclosed herein can be associated with a plurality of same or different detectable moieties via any mechanism disclosed herein or otherwise known in the art, which same or different detectable moieties can be associated with the anti-CD166 ICD antibody or antigen-binding polypeptide via same or different mechanisms of association as disclosed herein or otherwise known in the art.

Detectable moieties of the present invention include, without limitation, a moiety that produces, is capable of producing, or is capable of contributing to production of a signal detectable by any means known in the art. In particular instances, a detectable moiety produces, is capable of producing, or is capable of contributing to production of a signal detectable by, without limitation, visual means, spectroscopic means, photochemical means, biochemical means, immunochemical means, electromagnetic means, radiochemical means, chemical means, fluorescence, chemifluoresence, electrochemilumenscence, or chemiluminescence. In certain embodiments, a detectable moiety is a fluorescent moiety, radioactive moiety, paramagnetic moiety, chemiluminescent moiety, bioluminescent moiety, colorimetic label, polypeptide, enzyme, and/or ligand.

Detectable moieties include, without limitation, green fluorescent protein (GFP), red fluorescent protein (RFP), rhodamine, rhodamine-derived detectable moieties, fluorescein, fluorescein-derived detectable moieties, naphthalene, naphthalene-derived detectable moieties, coumarin, coumarin-derived detectable moieties, phycobiliproteins and derivatives such as phycoerythrin and phycocyanin, luciferase, beta-galactosidase, chromophores, phenolphthalein, malachite green, nitroaromatics such as nitrophenyl, diazo dyes, dabsyl (4-dimethylaminoazobenzene-4'-sulfonyl), His tag, and biotin-binding moieties such as streptavidin or avidin. A detectable moiety can be a radioisotope or radiolabel (e.g. $^{3}$H, $^{14}$C, $^{32}$P, $^{35}$S, $^{125}$I, zirconium-89 (89Zr), iodine-124 (124I), iodine-131 (131I), iodine-125 (125I), bismuth-212 (212Bi), bismuth-213 (213Bi), astatine-221 (221At), copper-67 (67Cu), copper-64 (64Cu), rhenium-186 (186Re), rhenium-188 (188Re), phosphorus-32 (32P), samarium-153 (153 Sm), lutetium-177 (177Lu), technetium-99m (99mTc), gallium-67 (67Ga), indium-111 (111In), or thallium-201 (201Tl), or a radiolabeled molecule. A detectable moiety may be a small molecule, a fluorescent dye, or a compound that may be detected by x-rays or electromagnetic radiation. A detectable moiety can be a catalytic substrate of an enzyme, wherein activity of enzyme with substrate produces a detectable signal. Enzyme detectable moieties of the present invention include, without limitation, peroxidase, alkaline phosphatase (AP), glucose oxidase, or β-galactosidase.

Those of skill in the art will appreciate that an anti-CD166 ICD antibody or antigen-binding polypeptide of the present invention is detectable, e.g., by a secondary antibody in a method of immunohistochemistry.

Therapeutic Moieties

In various embodiments of the present invention, an anti-CD166 ICD antibody or antigen-binding polypeptide of the present invention is associated with a therapeutic moiety. In various instances, an anti-CD166 ICD antibody or antigen-binding polypeptide as disclosed herein can be covalently or non-covalently associated with a therapeutic moiety. In various instances, an anti-CD166 ICD antibody or antigen-binding polypeptide as disclosed herein can be directly or indirectly associated with a therapeutic moiety. In various instances, an anti-CD166 ICD antibody or antigen-binding polypeptide as disclosed herein can be associated with a therapeutic moiety via a linker. In various instances, an anti-CD166 ICD antibody or antigen-binding polypeptide as disclosed herein can be fused or conjugated with a therapeutic moiety. In various instances, an anti-CD166 ICD antibody or antigen-binding polypeptide as disclosed herein is associated with a therapeutic moiety via a polypeptide terminus of the anti-CD166 ICD antibody or antigen-binding polypeptide. In various instances, an anti-CD166 ICD antibody or antigen-binding polypeptide as disclosed herein is associated with a therapeutic moiety via a non-terminal residue of the anti-CD166 ICD antibody or antigen-binding polypeptide. In various instances, an anti-CD166 ICD antibody or antigen-binding polypeptide as disclosed herein is associated with a therapeutic moiety via incorporation of the therapeutic moiety into the molecular structure of the anti-CD166 ICD antibody or antigen-binding polypeptide. In various instances, an anti-CD166 ICD antibody or antigen-binding polypeptide as disclosed herein can be associated with a plurality of same or different therapeutic moieties via any mechanism disclosed herein or otherwise known in the art, which same or different therapeutic moieties can be associated with the anti-CD166 ICD antibody or antigen-binding polypeptide via same or different mechanisms of association as disclosed herein or otherwise known in the art.

Therapeutic moieties of the present invention include drugs, e.g., a drug for treatment of a condition or disease. Therapeutic moieties of the present invention include, without limitation, a cytotoxic moiety, chemotherapeutic moiety, toxin, or radionuclide.

In various embodiments, a chemotherapeutic agent includes pro-apoptotic, cytostatic and/or cytotoxic agents, for example specifically including agents utilized and/or recommended for use in treating one or more diseases, disorders or conditions associated with undesirable cell proliferation. In certain embodiments, chemotherapeutic agents are useful in the treatment of cancer. In some embodiments, a chemotherapeutic agent may be or include one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, all-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent can be or include one or more of farnesyl-thiosalicylic acid (FTS), 4-(4-Chloro-2-methylphenoxy)-N-hydroxybutanamide (CMH), estradiol (E2), tetramethoxystilbene (TMS), 6-tocatrienol, salinomycin, or curcumin Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

In various embodiments, a chemotherapeutic agent includes pro-apoptotic, cytostatic and/or cytotoxic agents, for example specifically including agents utilized and/or recommended for use in treating one or more diseases, disorders or conditions associated with undesirable cell proliferation. In certain embodiments, chemotherapeutic agents are useful in the treatment of cancer. In some embodiments, a chemotherapeutic agent may be or include one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, all-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent can be or include one or more of farnesyl-thiosalicylic acid (FTS), 4-(4-Chloro-2-methylphenoxy)-N-hydroxybutanamide (CMH), estradiol (E2), tetramethoxystilbene (TMS), 6-tocatrienol, salinomycin, or curcumin Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

Epitopes and Binding

An anti-CD166 ICD antibody or antigen-binding polypeptide of the present invention can bind an epitope that is or includes amino acids of the intracellular domain of CD166. In various embodiments, the CD166 is a mammalian CD166. In various embodiments, the CD166 is a mouse or rat CD166. In various embodiments, the CD166 is a primate CD166. In various embodiments, the CD166 is a human CD166.

In certain embodiments, an anti-CD166 ICD antibody or antigen-binding polypeptide of the present invention can bind an epitope that is or includes an amino acid sequence present in the intracellular domain of CD166 (SEQ ID NO: 62). In certain instances, an anti-CD166 ICD antibody or antigen-binding polypeptide disclosed herein binds a CD166 ICD epitope present in a portion of SEQ ID NO: 62 that is or includes, e.g., 2, 3, 4, 5, 6, 7, 8, 9, 10, 11, or 12, amino acids selected from within the sequence of SEQ ID NO: 62. In certain embodiments, an epitope of an anti-CD166 ICD antibody or antigen-binding polypeptide disclosed herein is SEQ ID NO: 63 or a portion thereof (e.g., a portion including 2, 3, 4, 5 6, 7, 8, 9, 10, 11, or 12 amino acids selected from within the sequence of SEQ ID NO: 63). In particular embodiments, an epitope of an anti-CD166 ICD antibody or antigen-binding polypeptide disclosed herein is SEQ ID NO: 64 or a portion thereof (e.g., a portion including 2, 3, 4, 5 6, 7, 8, 9, 10, 11, or 12 amino acids selected from within the sequence of SEQ ID NO: 64). In certain embodiments, an epitope of an anti-CD166 ICD antibody or antigen-binding polypeptide disclosed herein is SEQ ID NO: 65 or a portion thereof (e.g., a portion including 2, 3, 4, 5 6, 7, 8, 9, 10, 11, or 12 amino acids selected from within the sequence of SEQ ID NO: 65). In particular embodiments, an epitope of an anti-CD166 ICD antibody or antigen-binding polypeptide disclosed herein is SEQ ID NO: 66 or a portion thereof (e.g., 2, 3, 4, 5 6, 7, 8, 9, 10, 11, or 12 amino acids selected from within the sequence of SEQ ID NO: 66).

In various embodiments, an anti-CD166 ICD antibody or antigen-binding polypeptide disclosed herein is any antibody or antigen-binding polypeptide having a CD166 epitope that is or includes SEQ ID NO: 62 or a portion thereof (e.g., 1, 2, 3, 4, 5, 6, 7, 8, 9, 10, 11, or 12 amino acids of SEQ ID NO: 62).

In various embodiments, an anti-CD166 ICD antibody or antigen-binding polypeptide disclosed herein is any antibody or antigen-binding polypeptide having a CD166 epitope that is or includes SEQ ID NO: 63 or a portion thereof (e.g., 1, 2, 3, 4, 5, 6, 7, 8, 9, 10, 11, or 12 amino acids of SEQ ID NO: 63).

In various embodiments, an anti-CD166 ICD antibody or antigen-binding polypeptide disclosed herein is any antibody or antigen-binding polypeptide having a CD166 epitope that is or includes SEQ ID NO: 64 or a portion thereof (e.g., 1, 2, 3, 4, 5, 6, 7, 8, 9, 10, 11, or 12 amino acids of SEQ ID NO: 64).

In various embodiments, an anti-CD166 ICD antibody or antigen-binding polypeptide disclosed herein is any antibody or antigen-binding polypeptide having a CD166 epitope that is or includes SEQ ID NO: 65 or a portion thereof (e.g., 1, 2, 3, 4, 5, 6, 7, 8, 9, 10, 11, or 12 amino acids of SEQ ID NO: 65).

In various embodiments, an anti-CD166 ICD antibody or antigen-binding polypeptide disclosed herein is any antibody or antigen-binding polypeptide having a CD166 epitope that is or includes SEQ ID NO: 66 or a portion thereof (e.g., 1, 2, 3, 4, 5, 6, 7, 8, 9, 10, 11, or 12 amino acids of SEQ ID NO: 66).

Amino acids of an epitope can be contiguous, non-contiguous, or a combination thereof.

In various embodiments, an epitope includes a plurality of contiguous amino acids of a CD166 ICD. In various embodiments, an epitope includes a plurality of contiguous amino acids of SEQ ID NO: 62, SEQ ID NO: 63, SEQ ID NO: 64, SEQ ID NO: 65, and/or SEQ ID NO:66. In various embodiments, an epitope includes a plurality of non-contiguous amino acids of SEQ ID NO: 62, SEQ ID NO: 63, SEQ ID NO: 64, SEQ ID NO: 65, and/or SEQ ID NO:66. In various embodiments, an epitope includes a plurality of contiguous amino acids of SEQ ID NO: 62, SEQ ID NO: 63, SEQ ID NO: 64, SEQ ID NO: 65, and/or SEQ ID NO:66 and a plurality of non-contiguous amino acids of SEQ ID NO: 62, SEQ ID NO: 63, SEQ ID NO: 64, SEQ ID NO: 65, and/or SEQ ID NO:66.

In various embodiments, an anti-CD166 ICD antibody or antigen-binding polypeptide disclosed herein binds SEQ ID NO: 62. In various embodiments, an anti-CD166 ICD antibody or antigen-binding polypeptide disclosed herein binds SEQ ID NO: 63. In various embodiments, an anti-CD166 ICD antibody or antigen-binding polypeptide disclosed herein binds SEQ ID NO: 64. In various embodiments, an anti-CD166 ICD antibody or antigen-binding polypeptide disclosed herein binds SEQ ID NO: 65. In various embodiments, an anti-CD166 ICD antibody or antigen-binding polypeptide disclosed herein binds SEQ ID NO: 66.

In various embodiments, an anti-CD166 ICD antibody or antigen-binding polypeptide disclosed herein is any antibody or antigen-binding polypeptide that binds SEQ ID NO: 62. In various embodiments, an anti-CD166 ICD antibody or antigen-binding polypeptide disclosed herein is any antibody or antigen-binding polypeptide that binds SEQ ID NO: 63. In various embodiments, an anti-CD166 ICD antibody or antigen-binding polypeptide disclosed herein is any antibody or antigen-binding polypeptide that binds SEQ ID NO: 64. In various embodiments, an anti-CD166 ICD antibody or antigen-binding polypeptide disclosed herein is any antibody or antigen-binding polypeptide that binds SEQ ID NO: 65. In various embodiments, an anti-CD166 ICD antibody or antigen-binding polypeptide disclosed herein is any antibody or antigen-binding polypeptide that binds SEQ ID NO: 66.

In various embodiments, an anti-CD166 ICD antibody or antigen-binding polypeptide disclosed herein is any antibody or antigen-binding polypeptide having a CD166 epitope that is the same as a CD166 epitope of an anti-CD166 ICD antibody or antigen-binding polypeptide having a sequence described herein.

In various embodiments, an anti-CD166 ICD antibody or antigen-binding polypeptide disclosed herein is any antibody or antigen-binding polypeptide that competes with an anti-CD166 ICD antibody or antigen-binding polypeptide having a sequence described herein for binding of CD166 or an epitope thereof (a "competing antibody"). A provided antibody or antigen-binding polypeptide and an anti-CD166 ICD antibody or antigen-binding polypeptide having a sequence described herein can be understood to compete if binding of a provided antibody or antigen-binding polypeptide to an antigen molecule blocks, inhibits, interferes with, or otherwise reduces binding of an anti-CD166 ICD antibody or antigen-binding polypeptide having a sequence described herein to the same antigen molecule, according to any measure, assay, or method of prediction known in the art. In certain such instances, a provided antibody or antigen-binding polypeptide and an anti-CD166 ICD antibody or antigen-binding polypeptide having a sequence described herein can be understood to compete if binding of a provided antibody or antigen-binding polypeptide to an antigen molecule blocks, inhibits, interferes with, or otherwise reduces binding of an anti-CD166 ICD antibody or antigen-binding polypeptide having a sequence described herein to the same antigen molecule by steric inhibition, occupation of an epitope or binding site of an anti-CD166 ICD antibody or antigen-binding polypeptide having a sequence described herein by the provided antibody or antigen-binding polypeptide, or occlusion of an anti-CD166 ICD antibody or antigen-binding polypeptide having a sequence described herein from an epitope or binding site by the provided antibody or antigen-binding polypeptide. In various embodiments, an antibody or antigen-binding polypeptide disclosed herein binds a CD166 epitope that is identical to and/or overlapping with the epitope of an anti-CD166 ICD antibody or antigen-binding polypeptide having a sequence described herein. In various embodiments, an antigen or epitope for which a provided antibody and an anti-CD166 ICD antibody or antigen-binding polypeptide having a sequence described herein compete can be any of a complete CD166 protein, a portion of a CD166 protein, an isolated CD166 protein, an isolated portion of a CD166 protein, or a complete or portion of a CD166 protein present in a cell, tissue, organ, sample or subject. In various embodiments, an antigen or epitope for which a provided antibody and an anti-CD166 ICD antibody or antigen-binding polypeptide having a sequence described herein compete can be present in a cell, present in a cell membrane, or removed from a cell membrane. In various embodiments, an antigen or epitope for which a provided antibody and an anti-CD166 ICD antibody or antigen-binding polypeptide having a sequence described herein compete can be present in an organism. In various embodiments, an antigen or epitope for which a provided antibody and an anti-CD166 ICD antibody or antigen-binding polypeptide having a sequence described herein compete can be a CD166 protein or portion thereof produced by a cell, tissue, organ, or organism. In various embodiments, an antigen or epitope for which a provided antibody and an anti-CD166 ICD antibody or antigen-binding polypeptide having a sequence described herein compete can be a synthetic CD166 protein or a portion thereof. In various embodiments, an antigen or epitope for which a provided antibody and an anti-CD166 ICD antibody or antigen-binding polypeptide having a sequence described herein compete can be an ICD portion of CD166. In various embodiments, an antigen or epitope for which a provided antibody and an anti-CD166 ICD antibody or antigen-binding polypeptide having a sequence described herein compete can be a portion of CD166 according to SEQ ID NO: 62, SEQ ID NO: 63, SEQ ID NO: 64, SEQ ID NO: 65, or SEQ ID NO: 66.

In various embodiments, an anti-CD166 ICD antibody or antigen-binding polypeptide disclosed herein binds a CD166 ICD epitope disclosed herein with a $K_D$ of less than 100 nM, less than 75 nM, less than 50 nM, less than 40 nM, less than 30 nM, less than 20 nM, less than 10 nM, less than 5 nM, less than 1 nM, less than 900 pM, less than 800 pM, less than 700 pM, less than 600 pM, less than 500 pM, less than 400 pM, less than 300 pM, less than 200 pM, less than 100 pM, or less than 50 pM. In various embodiments, an anti-CD166 ICD antibody or antigen-binding polypeptide disclosed herein binds a CD166 ICD epitope disclosed herein with a $K_D$ of greater than 5 pM, greater than 10 pM, greater than 25 pM, greater than 50 pM, greater than 100 pM, greater than 200 pM, greater than 300 pM, greater than 400 pM, greater than 500 pM, greater than 600 pM, greater than 700 pM, greater than 800 pM, greater than 900 pM, greater than 1 nM, greater than 5 nM, or greater than 10 nM. In various embodiments, an anti-CD166 ICD antibody or antigen-binding polypeptide disclosed herein binds a CD166 ICD epitope disclosed herein with a $K_D$ of 100 nM to 10 pM, 50 nM to 10 pM, 50 nM to 100 pM, 50 nM to 500 pM, 50 nM to 1 nM, 25 nM to 10 pM, 25 nM to 100 pM, 25 nM to 500 pM, 25 nM to 1 nM, 10 nM to 10 pM, 10 nM to 100 pM, 10 nM to 500 pM, or 10 nM to 1 nM.

Binding properties of an antibody or antigen-binding polypeptide described herein can be measured by techniques known in the art, including, without limitation, any of the following: BIACORE analysis, Enzyme Linked Immunosorbent Assay (ELISA), x-ray crystallography, sequence analysis and scanning mutagenesis. Binding interaction of an antibody or antigen-binding polypeptide can be analyzed using surface plasmon resonance (SPR). SPR or Biomolecular Interaction Analysis (BIA) can detect bio-specific interactions in real time, without labeling any of the interactants.

Applications

The present invention includes various applications related to CD166 and/or to an anti-CD166 ICD antibody or antigen-binding polypeptide disclosed herein. In certain embodiments, an anti-CD166 ICD antibody or antigen-binding polypeptide disclosed herein is used in analysis of a CD166 concentration, amount, level, expression profile, or localization in a cell, tissue, organ, sample, or subject. In various embodiments an analysis is a diagnostic analysis. In various embodiments an analysis is monitoring the progress of a condition or disease, or a treatment thereof.

In certain embodiments, an anti-CD166 ICD antibody or antigen-binding polypeptide disclosed herein is used in detecting or diagnosing a condition or disease. In certain instances, the use of an anti-CD166 ICD antibody or antigen-binding polypeptide in detecting or diagnosing a condition or disease includes determining whether a cell, tissue, organ, sample, or subject includes or included CD166 in a concentration, amount, level, expression profile, or localization indicative of a condition or disease. Detection of a condition or disease can include a determination that a cell, tissue, organ, sample, or subject includes or included CD166 in a concentration, amount, level, expression profile, or localization indicative of a condition or disease. In various instances, determination that a cell, tissue, organ, or sample includes or included CD166 in a concentration, amount, level, expression profile, or localization indicative of a condition or disease includes comparison of a CD166 concentration, amount, level, expression profile, or localization to that of a reference. A cell, tissue, organ, sample, or subject can be diagnosed as having, as affected by, or as representative of a condition or disease if a cell, tissue, organ, sample, or subject is determined to include or to have included CD166 in a concentration, amount, level, expression profile, or localization indicative of a condition or disease. It is to be understood that a determination that a cell, tissue, organ, or sample includes or included CD166 in a concentration, amount, level, expression profile, or localization indicative of a condition or disease can be, in some instances, sufficient for or equivalent to detection or diagnosis of a condition or disease in a subject from which a cell, tissue, organ, or sample was derived.

In certain embodiments, an anti-CD166 ICD antibody or antigen-binding polypeptide disclosed herein is used as a factor (e.g., one of two or more factors, e.g., a constellation of factors) considered in detection or diagnosis of a condition or disease. In certain instances, detection or diagnosis of a condition or disease can include hierarchical, joint, combined, weighted, integrated, Boolean, objective, subjective, or other means of cumulatively considering or analyzing two or more factors, at least one of which can be a concentration, amount, level, expression profile, or localization of CD166. Thus, in certain instances, detection or diagnosis of a condition or disease by cumulative consideration or analysis of a plurality of factors, can include use of an anti-CD166 ICD antibody or antigen-binding polypeptide in determining whether a cell, tissue, organ, sample, or subject includes or included CD166 in a concentration, amount, level, expression profile, or localization contributes to detection or diagnosis. In various instances, determination that a cell, tissue, organ, or sample includes or included CD166 in a concentration, amount, level, expression profile, or localization indicative of a condition or disease includes comparison of a CD166 concentration, amount, level, expression profile, or localization to that of a reference.

In certain embodiments, an anti-CD166 ICD antibody or antigen-binding polypeptide disclosed herein is used in determining the likelihood or risk that a subject has or will have a condition or disease. In certain instances, the use of an anti-CD166 ICD antibody or antigen-binding polypeptide in determining the likelihood or risk that a subject has or will have a condition or disease includes determining whether a cell, tissue, organ, sample, or subject includes or included CD166 in a concentration, amount, level, expression profile, or localization indicative of a condition or disease. Determining the likelihood or risk that a subject has or will have a condition or disease can include a determination that a cell, tissue, organ, sample, or subject includes or included CD166 in a concentration, amount, level, expression profile, or localization indicative of a likelihood or risk of a present or future condition or disease. In various instances, determination that a cell, tissue, organ, or sample includes or included CD166 in a concentration, amount, level, expression profile, or localization indicative of a likelihood or risk of a present or future condition or disease includes comparison of a CD166 concentration, amount, level, expression profile, or localization to that of a reference. It is to be understood that a determination that a cell, tissue, organ, or sample includes or included CD166 in a concentration, amount, level, expression profile, or localization indicative of a likelihood or risk of a present or future condition or disease can be, in some instances, sufficient for or equivalent to detection or diagnosis of a condition or disease in a subject from which a cell, tissue, organ, or sample was derived.

In certain embodiments, an anti-CD166 ICD antibody or antigen-binding polypeptide disclosed herein is used as a factor considered in determining the likelihood or risk that a subject has or will have a condition or disease. In certain instances, determining the likelihood or risk that a subject has or will have a condition or disease can include hierarchical, joint, combined, weighted, integrated, Boolean, objective, subjective, or other means of cumulatively considering or analyzing two or more factors, at least one of which can be a concentration, amount, level, expression profile, or localization of CD166. Thus, in certain instances determining the likelihood or risk that a subject has or will have a condition or disease includes cumulative consideration or analysis of a plurality of factors, which plurality of factors include use of an anti-CD166 ICD antibody or antigen-binding polypeptide in determining CD166 concentration, amount, level, expression profile, or localization in a cell, tissue, organ, sample, or subject. In various instances, determination that a cell, tissue, organ, or sample includes or included CD166 in a concentration, amount, level, expression profile, or localization indicative of a likelihood or risk that a subject has or will have a condition or disease includes comparison of a CD166 concentration, amount, level, expression profile, or localization to that of a reference.

In certain embodiments, an anti-CD166 ICD antibody or antigen-binding polypeptide disclosed herein is used in determining whether or not to administer a treatment regimen for treatment of a condition or disease. If a subject is determined to have or be at risk of a condition or disease based, in full or in part, on a determined concentration, amount, level, expression profile, or localization of CD166, or a change therein, a treatment regimen for the condition or disease can be initiated. If a subject is determined not to have or be at risk of a condition or disease based, in full or in part, on a determined concentration, amount, level, expression profile, or localization of CD166, or a change therein, a treatment regimen for the condition or disease will, in certain instances, not be initiated.

In certain embodiments, an anti-CD166 ICD antibody or antigen-binding polypeptide disclosed herein is used in selecting or identifying a subject for treatment via a treatment regimen, and/or for selecting or identifying a subject that should not receive treatment via a treatment regimen. In certain embodiments, an anti-CD166 ICD antibody or antigen-binding polypeptide disclosed herein is used in an analysis that precedes or is a prerequisite to prescription or administration of a treatment regimen to a subject. In various embodiments, a subject is selected or identified for treatment if the subject is determined to have a concentration, amount, level, expression profile, or localization of CD166, or a change therein, indicative that the subject has or is at risk of a condition or disease. In various embodiments, a subject is selected or identified for treatment if the subject is determined to have or be at risk of a condition or disease based, in full or in part, on a concentration, amount, level, expression profile, or localization of CD166, or a change therein.

In certain embodiments, an anti-CD166 ICD antibody or antigen-binding polypeptide disclosed herein is used in identifying CD166 as a biomarker. In certain instances, a cell, tissue, organ, sample, or subject is provided, which cell, tissue, organ, sample, or subject is known, diagnosed, or expected to have, represent, or be at risk of a condition or disease, or is derived from a subject known, diagnosed, or expected to have, represent, or be at risk of a condition or disease. The present invention can include determining a concentration, amount, level, expression profile, or localization of CD166 in a test cell, tissue, organ, sample, or subject and comparing the determined CD166 concentration, amount, level, expression profile, or localization to that of a reference. In various instances, it may be determined that a test cell, tissue, organ, sample, or subject includes a different (e.g., significantly different) CD166 concentration, amount, level, expression profile, or localization than does a reference, whereby CD166 is a biomarker of a relevant condition or disease. In various instances, it may be determined that a test cell, tissue, organ, sample, or subject does not include a different (e.g., significantly different) CD166 concentration, amount, level, expression profile, or localization than does a reference, whereby CD166 is not a biomarker of a relevant condition or disease.

In certain embodiments, an anti-CD166 ICD antibody or antigen-binding polypeptide disclosed herein is used in monitoring a condition or disease. As used herein, monitoring a condition or disease can include identifying a change in activity, severity, stage, character, or other feature over a period of time. Monitoring can include a measurement at a plurality of time points, including, without limitation, a first time point and a second time point. In some instances, a first time point is prior to initiation of a treatment regimen. In some instances, a first time point is after initiation of a treatment regimen. In some instances, a second time point is during a treatment regimen. In some instances, a second time point is after completion of a treatment regimen. In some instances, there is no change in treatment or absence thereof between a first time point and a second time point. As used herein, a measurement at a time point of a monitoring scheme can include determining a concentration, amount, level, expression profile, or localization of CD166 in a cell, tissue, organ, sample, or subject. In various embodiments, the determination of a concentration, amount, level, expression profile, or localization of CD166 in a cell, tissue, organ, sample, or subject includes use of an anti-CD166 ICD antibody or antigen-binding polypeptide disclosed herein. In various instances, a determined concentration, amount, level, expression profile, or localization of CD166 is compared to that of a reference. In certain instances, a reference is a determination from an earlier time point. In certain instances, a reference is a determination from a later time point.

In certain embodiments, an anti-CD166 ICD antibody or antigen-binding polypeptide disclosed herein is used in monitoring a treatment, e.g., success or failure of a treatment. As used herein, monitoring a treatment can include identifying a change in activity, severity, stage, character, or other feature over a period of time. Monitoring can include a measurement at a plurality of time points, including, without limitation, a first time point and a second time point. In some instances, a first time point is prior to initiation of a treatment regimen. In some instances, a first time point is after initiation of a treatment regimen. In some instances, a second time point is during a treatment regimen. In some instances, a second time point is after completion of a treatment regimen. In some instances, there is no change in treatment between a first time point and a second time point. In some instances, there is a change in treatment between a first time point and a second time point. As used herein, a measurement at a time point of a monitoring scheme can include determining a concentration, amount, level, expression profile, or localization of CD166 in a cell, tissue, organ, sample, or subject. In various embodiments, the determination of a concentration, amount, level, expression profile, or localization of CD166 in a cell, tissue, organ, sample, or subject includes use of an anti-CD166 ICD antibody or antigen-binding polypeptide disclosed herein. In various instances, a determined concentration, amount, level, expression profile, or localization of CD166 is compared to that of a reference. In certain instances, a reference is a determination from an earlier time point. In certain instances, a reference is a determination from a later time point.

In certain embodiments, an anti-CD166 ICD antibody or antigen-binding polypeptide disclosed herein is used in determining whether or not to change a treatment regimen for treatment of a condition or disease. In certain instances if monitoring of a subject receiving treatment indicates that a current treatment regimen has not resulted in effective treatment of a condition or disease, the current treatment regimen may be revised, e.g., to a different or more stringent regimen than the current regiment. In certain instances if monitoring of a subject receiving treatment indicates that a current treatment regimen has not resulted improvement, or substantial improvement, in a condition or disease, the current treatment regimen may be revised, e.g., to a different or more stringent regimen than the current regiment. In certain instances if monitoring of a subject receiving treatment indicates that a current treatment regimen has resulted in effective treatment of a condition or disease, the current treatment regimen may be revised, e.g., to a different or less stringent regimen than the current regiment. In certain instances if monitoring of a subject receiving treatment indicates that a current treatment regimen has resulted in improvement, e.g., substantial improvement, in a condition or disease, the current treatment regimen may be revised, e.g., to a different or less stringent regimen than the current regiment. It is to be understood that a change in treatment regimen is ultimately determined by a medical practitioner or other individual administering or directing administration of a treatment regimen.

In certain embodiments, the present invention includes a service wherein a method, technique, or analysis described herein is performed upon a provided sample.

A reference can be any comparable cell, tissue, organ, sample, or subject, which cell, tissue, organ, sample, or subject is (a) is known, diagnosed, or expected to have, represent, or be at risk of a condition or disease, or (b) is known, diagnosed, or expected not to have, represent, or be at risk of a condition or disease. A reference can also be any standard, accepted, selected, set, experimentally determined, arbitrarily determined, systematically determined, or relative value for a concentration, amount, level, expression profile, or localization of CD166 in a cell, tissue, organ, sample, or subject. In particular instances, a reference is a sample of a same cell type, tissue type, sample type, or subject having same or similar characteristics for one or more relevant medical parameters. In particular instances, a reference is a sample of a same cell type, tissue type, sample type, or subject having same or similar characteristics for one or more relevant medical parameters, which reference is known to be healthy in that the subject is not known, diagnosed, or expected to have a particular condition or disease. A reference can be derived from a same subject as a test cell, tissue, organ, or sample. A reference can be a healthy tissue from a same subject as a test cell, tissue, organ, or sample. A reference can be from a same subject at a different time point, e.g., an earlier time point or a later time point. In some instances, a reference time point is prior to initiation of a treatment regimen and a test time point is after initiation of a treatment regimen. In some instances, a reference time point is prior to initiation of a treatment regimen and a test time point is during or after completion of a treatment regimen.

Various embodiments enclosed herein include measuring or determining a CD166 concentration, amount, level, expression profile, or localization in a cell, tissue, organ, sample, or subject using an anti-CD166 ICD antibody or antigen-binding polypeptide disclosed herein. In various embodiments, measuring or determining a CD166 concentration, amount, level, expression profile, or localization in a cell, tissue, organ, sample, or subject includes a step of contacting the cell, tissue, organ, sample, or subject with an anti-CD166 ICD antibody or antigen-binding polypeptide disclosed herein. In various embodiments, measuring or determining a CD166 concentration, amount, level, expression profile, or localization in a cell, tissue, organ, sample, or subject includes a step of permitting an anti-CD166 ICD antibody or antigen-binding polypeptide disclosed herein to bind CD166 of a cell, tissue, organ, sample, or subject exposed to the anti-CD166 ICD antibody or antigen-binding polypeptide disclosed herein. In certain embodiments, the present invention includes incubating the cell, tissue, organ, sample, or subject with an anti-CD166 ICD antibody or antigen-binding polypeptide in a manner sufficient to permit binding of the anti-CD166 ICD antibody or antigen-binding polypeptide with CD166 of a cell, tissue, organ, sample, or subject. In certain embodiments, the present invention includes a step of removing unbound anti-CD166 ICD antibody or antigen-binding polypeptide, e.g., by washing a cell, tissue, organ, sample, or subject exposed to the anti-CD166 ICD antibody or antigen-binding polypeptide. In certain embodiments, the present invention includes a step of determining the presence, absence, concentration, amount, level, expression profile, or localization of CD166 in a cell, tissue, organ, sample, or subject.

In certain embodiments including a step of determining the presence, absence, concentration, amount, level, expression profile, or localization of CD166 in a cell, tissue, organ, sample, or subject, an anti-CD166 ICD antibody or antigen-binding polypeptide is not associated with a detectable moiety. In certain instances, detection of CD166 includes a step of labeling CD166 bound by an anti-CD166 ICD antibody or antigen-binding polypeptide as described herein by providing a secondary antibody. In particular instances, a secondary antibody is an antibody that binds anti-CD166 ICD antibody or antigen-binding polypeptide. Accordingly, in certain embodiments, detecting CD166 includes contacting a cell, tissue, organ, sample, or subject exposed to or bound by anti-CD166 ICD antibody or antigen-binding polypeptide (or at least contacting CD166-bound anti-CD166 ICD antibody or antigen-binding polypeptide) with a secondary antibody. Certain embodiments further include a step of permitting a secondary antibody to bind anti-CD166 ICD antibody or antigen-binding polypeptide. In certain embodiments, the present invention includes incubating a cell, tissue, organ, sample, or subject with a secondary antibody in a manner sufficient to permit binding of the secondary antibody with anti-CD166 ICD antibody or antigen-binding polypeptide. In certain embodiments, the present invention includes a step of removing unbound secondary antibody, e.g., by washing a cell, tissue, organ, sample, or subject exposed to the secondary antibody. In certain instances, a secondary antibody is an antibody that binds anti-CD166 ICD antibody or antigen-binding polypeptide, which secondary antibody is associated with a detectable moiety. Those of skill in the art will be familiar with methods that are appropriate for use in detection of a present detectable moiety.

In certain embodiments including a step of determining the presence, absence, concentration, amount, level, expression profile, or localization of CD166 in a cell, tissue, organ, sample, or subject, an anti-CD166 ICD antibody or antigen-binding polypeptide is associated with a detectable moiety that is bound by a secondary antibody. In certain instances, detection of CD166 includes a step of labeling CD166 bound by an anti-CD166 ICD antibody or antigen-binding polypeptide as described herein by providing a secondary antibody. In particular instances, a secondary antibody is an antibody that binds anti-CD166 ICD antibody or antigen-binding polypeptide. Accordingly, in certain embodiments, detecting CD166 includes contacting a cell, tissue, organ, sample, or subject exposed to or bound by anti-CD166 ICD antibody or antigen-binding polypeptide (or at least contacting CD166-bound anti-CD166 ICD antibody or antigen-binding polypeptide) with a secondary antibody. Certain embodiments further include a step of permitting a secondary antibody to bind anti-CD166 ICD antibody or antigen-binding polypeptide. In certain embodiments, the present invention includes incubating a cell, tissue, organ, sample, or subject with a secondary antibody in a manner sufficient to permit binding of the secondary antibody with anti-CD166 ICD antibody or antigen-binding polypeptide. In certain embodiments, the present invention includes a step of removing unbound secondary antibody, e.g., by washing a cell, tissue, organ, sample, or subject exposed to the secondary antibody. In certain instances, a secondary antibody is an antibody that binds anti-CD166 ICD antibody or antigen-binding polypeptide, which secondary antibody is associated with a detectable moiety. Those of skill in the art will be familiar with methods that are appropriate for use in detection of a present detectable moiety of a secondary antibody.

In certain embodiments including a step of determining the presence, absence, concentration, amount, level, expression profile, or localization of CD166 in a cell, tissue, organ, sample, or subject, an anti-CD166 ICD antibody or antigen-binding polypeptide is associated with a detectable moiety, wherein anti-CD166 ICD antibody or antigen-binding polypeptide bound with CD166 is detected without use of a secondary antibody. In certain embodiments, a detectable moiety associated (e.g., directly associated) with an anti-CD166 ICD antibody or antigen-binding polypeptide is detected. Those of skill in the art will be familiar with methods that are appropriate for use in detection of a present detectable moiety of a secondary antibody.

In various embodiments, a cell, tissue, organ, sample, or subject is contacted with a blocking or quenching agent to reduce, minimize, or eliminate non-specific binding of anti-CD166 ICD antibody or antigen-binding polypeptide to the cell, tissue, organ, sample, or subject prior to contacting the cell, tissue, organ, sample, or subject with anti-CD166 ICD antibody or antigen-binding polypeptide.

Without limitation, means of detecting a detectable moiety can include, without limitation, immunohistochemistry, electropherography, Western blot analysis, immunoprecipitation analysis, and/or microscopy. Those of skill in the art will be familiar with methods that are appropriate for use in detection of a present detectable moiety of a secondary antibody.

A condition or disease of the present disclosure can be, without limitation, a condition or disease associated with a level, concentration, amount, level, expression profile, or localization of CD166 in a cell, tissue, organ, sample, or subject. In some embodiments, a level, concentration, amount, level, expression profile, or localization of CD166 in a cell, tissue, organ, sample, or subject can differ from a concentration, amount, level, expression profile, or localization of CD166 in a reference. In certain instances, a condition or disease of the present disclosure can be, without limitation, cancer (e.g., a tumor, e.g., a tumor that expresses CD166). In certain instances, a condition or disease of the present disclosure can be, without limitation, a condition or disease characterized by activated lymphocytes or activated monocytes (leukocytes) (e.g., that express CD166).

In particular embodiments, a condition or disease of the present disclosure can be a cancer selected from prostate cancer, squamous cell skin cancer, breast cancer, ovarian cancer, lung adenocarcinoma, small cell lung cancer, non-small cell lung cancer, small cell cancer of the esophagus, clear cell kidney cancer, cancer of the small intestine, adenocarcinoma of the colon, papillary thyroid cancer, endometrial cancer, rectal cancer, squamous cell lung cancer, laryngeal cancer, pancreatic cancer, squamous cell cervical cancer, squamous cell esophageal cancer, liver cancer, cancer of the gastric cardia, stomach cancer, cancer of the abdominal cavity, transitional cell cancer of the bladder, melanoma, breast cancer, endometrial cancer, cholangiocarcinoma, and castration-resistant prostate cancer.

In particular embodiments, a condition or disease of the present disclosure can be the presence of activated lymphocytes and/or activated monocytes (leukocytes). In particular embodiments, a condition or disease of the present disclosure can be the presence of elevated activated lymphocytes and/or activated monocytes (leukocytes), e.g., as compared to a reference.

In particular embodiments, a condition or disease of the present disclosure can be an inflammatory condition characterized by activated lymphocytes or activated monocytes (leukocytes). In particular embodiments, a condition or disease of the present disclosure can be a condition or disease characterized by activated lymphocytes or activated monocytes (leukocytes) selected from, without limitation, cancer, rheumatoid arthritis, halo nevus, myelodysplastic syndrome, lupus, Type 1 diabetes, periodontitis, sickle cell anemia, inflammatory bowel disease, and Behcet's Disease.

A sample of the present disclosure can be any material having been obtained or derived from a source of interest, such as a subject. In some embodiments, a source of interest is or includes biological tissue or fluid. In some embodiments, a biological tissue or fluid may be or include amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humor, vomit, and/or combinations or component(s) thereof. In some embodiments, a biological fluid may be or include an intracellular fluid, an extracellular fluid, an intravascular fluid (blood plasma), an interstitial fluid, a lymphatic fluid, and/or a transcellular fluid. In some embodiments, a biological fluid may be or include a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample is or includes cells obtained from a subject. In some embodiments, a sample is a "primary sample" obtained directly from a source of interest by any appropriate means. In some embodiments, a sample is a preparation obtained by processing (e.g., by removing one or more components of and/or by adding one or more agents to) a primary sample. Such a "processed sample" may comprise, for example cells, nucleic acids, or proteins extracted, obtained, or derived from a primary sample.

In particular instances, a sample can be a cell or tissue, such as a tumor or cancer cell or a tumor or cancer tissue. In certain instances, a sample can include cells of a tumor or cancer cell line, tumor or cancer cells obtained or derived from a subject. In various embodiments, a sample can be or include cells or tissue that are present in a medium, fixed, formalin-fixed, and/or paraffin embedded. In various embodiments, cancer cells can include cells of cell line selected from H292, HCC1806, MDA-MB-231, BXPC3, HT29, and BT20. In various embodiments, cancer cells can include non-small cell lung cancer cells, breast cancer cells, ovarian cancer cells, endometrial cancer cells, cholangiocarcinoma cells, head and neck cancer cells, or castration-resistant prostate cancer cells, or cells of any tumor or cancer disclosed herein. In various embodiment, a cell, tissue, or sample can be of a cancer or tumor selected from prostate cancer, squamous cell skin cancer, breast cancer, ovarian cancer, lung adenocarcinoma, small cell lung cancer, non-small cell lung cancer, small cell cancer of the esophagus, clear cell kidney cancer, cancer of the small intestine, adenocarcinoma of the colon, papillary thyroid cancer, endometrial cancer, rectal cancer, squamous cell lung cancer, laryngeal cancer, pancreatic cancer, squamous cell cervical cancer, squamous cell esophageal cancer, liver cancer, cancer of the gastric cardia, stomach cancer, cancer of the abdominal cavity, transitional cell cancer of the bladder, melanoma, breast cancer, endometrial cancer, cholangiocarcinoma, and castration-resistant prostate cancer.

A treatment regimen of the present invention can include, without limitation, administration to a subject of a cancer therapeutic (such as a chemotherapeutic agent) and/or an anti-CD166 antibody or antigen-binding polypeptide (such as an anti-CD166 antibody or antigen-binding polypeptide that is not an anti-CD166 ICD antibody or antigen-binding polypeptide).

In various embodiments, a chemotherapeutic agent includes pro-apoptotic, cytostatic and/or cytotoxic agents, for example specifically including agents utilized and/or recommended for use in treating one or more diseases, disorders or conditions associated with undesirable cell proliferation. In certain embodiments, chemotherapeutic agents are useful in the treatment of cancer. In some embodiments, a chemotherapeutic agent may be or include one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, all-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent can be or include one or more of farnesyl-thiosalicylic acid (FTS), 4-(4-Chloro-2-methylphenoxy)-N-hydroxybutanamide (CMH), estradiol (E2), tetramethoxystilbene (TMS), 6-tocatrienol, salinomycin, or curcumin Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

In various embodiments, an anti-CD166 antibody or antigen-binding polypeptide (such as an anti-CD166 antibody or antigen-binding polypeptide that is not an anti-CD166 ICD antibody or antigen-binding polypeptide) is a therapeutic antibody or antigen-binding polypeptide comprising a heavy chain according to SEQ ID NO: 46 and/or a light chain according to SEQ ID NO: 52. In particular instances, a therapeutic antibody or antigen-binding polypeptide is an antibody or antigen-binding polypeptide comprising a heavy chain variable domain according to SEQ ID NO: 48 or SEQ ID NO: 49, and/or a light chain variable domain according to SEQ ID NO: 53, SEQ ID NO: 54, SEQ ID NO: 55, or SEQ ID NO: 56. In particular instances, a therapeutic antibody or antigen-binding polypeptide is an antibody or antigen-binding polypeptide comprising one or more of (a) an HCDR1 according to SEQ ID NO: 49; (b) an HCDR2 according to SEQ ID NO: 50; (c) an HCDR3 according to SEQ ID NO: 51; (d) a LCDR1 according to SEQ ID NO: 57; (e) an LCDR1 according to SEQ ID NO: 58; (f) an LCDR2 according to SEQ ID NO: 59; (g) an LCDR2 according to SEQ ID NO: 60; and/or (h) a LCDR3 according to SEQ ID NO: 61.

In particular instances, a therapeutic antibody or antigen-binding polypeptide is an antibody or antigen-binding polypeptide comprising a heavy chain according to SEQ ID NO: 46 and a light chain according to SEQ ID NO: 52. In particular instances, a therapeutic antibody or antigen-binding polypeptide is an antibody or antigen-binding polypeptide comprising a first heavy chain according to SEQ ID NO: 46, a second heavy chain according to SEQ ID NO: 46, a first light chain according to SEQ ID NO: 52, and second light chain according to SEQ ID NO: 52.

In particular instances, a therapeutic antibody or antigen-binding polypeptide is an antibody or antigen-binding polypeptide comprising a heavy chain variable domain according to SEQ ID NO: 48 or SEQ ID NO: 49, and a light chain variable domain according to SEQ ID NO: 53, SEQ ID NO: 54, SEQ ID NO: 55, or SEQ ID NO: 56. In particular instances, a therapeutic antibody or antigen-binding polypeptide is an antibody or antigen-binding polypeptide comprising a first heavy chain variable domain according to SEQ ID NO: 48 or SEQ ID NO: 49, a second heavy chain variable domain according to SEQ ID NO: 48 or SEQ ID NO: 49, a first light chain variable domain according to SEQ ID NO: 53, SEQ ID NO: 54, SEQ ID NO: 55, or SEQ ID NO: 56, and a second light chain variable domain according to SEQ ID NO: 53, SEQ ID NO: 54, SEQ ID NO: 55, or SEQ ID NO: 56.

In particular instances, a therapeutic antibody or antigen-binding polypeptide is an antibody or antigen-binding polypeptide comprising (a) an HCDR1 according to SEQ ID NO: 49; (b) an HCDR2 according to SEQ ID NO: 50; (c) an HCDR3 according to SEQ ID NO: 51; (d) an LCDR1 according to SEQ ID NO: 57 or SEQ ID NO: 58; (e) an LCDR2 according to SEQ ID NO: 59 or SEQ ID NO: 60; and (f) an LCDR3 according to SEQ ID NO: 61. In particular instances, a therapeutic antibody or antigen-binding polypeptide is an antibody or antigen-binding polypeptide comprising (a) a first HCDR1 according to SEQ ID NO: 49; (b) a first HCDR2 according to SEQ ID NO: 50; (c) a first HCDR3 according to SEQ ID NO: 51; (d) a first LCDR1 according to SEQ ID NO: 57 or SEQ ID NO: 58; (e) a first LCDR2 according to SEQ ID NO: 59 or SEQ ID NO: 60; (f) a first LCDR3 according to SEQ ID NO: 61; (g) a second HCDR1 according to SEQ ID NO: 49; (h) a second HCDR2 according to SEQ ID NO: 50; (i) a second HCDR3 according to SEQ ID NO: 51; (j) a second LCDR1 according to SEQ ID NO: 57 or SEQ ID NO: 58; (k) a second LCDR2 according to SEQ ID NO: 59 or SEQ ID NO: 60; (l) a second LCDR3 according to SEQ ID NO: 61. In some instances a therapeutic antibody can be monoclonal.

In certain instances, a therapeutic antibody or antigen-binding polypeptide is a therapeutic antibody or antigen binding polypeptide that specifically binds to an immune checkpoint protein. In certain instances, a therapeutic antibody or antigen-binding polypeptide is an anti-PD-1 antibody or antigen-binding polypeptide. In certain instances, a therapeutic anti-PD-1 antibody or antigen-binding polypeptide is an activatable antibody or antigen-binding polypeptide. In particular embodiments, a therapeutic anti-PD-1 antibody or antigen-binding polypeptide is an anti-PD-1 antibody or antigen-binding polypeptide (and/or an anti-PD-1 activatable antibody or antigen-binding polypeptide) associated with a therapeutic moiety. In certain instances, a therapeutic antibody or antigen-binding polypeptide is an anti-PD-L1 antibody or antigen-binding polypeptide. In certain instances, a therapeutic anti-PD-L1 antibody or antigen-binding polypeptide is an activatable antibody or antigen-binding polypeptide. In particular embodiments, a therapeutic anti-PD-L1 antibody or antigen-binding polypeptide is an anti-PD-L1 antibody or antigen-binding polypeptide (and/or an anti-PD-L1 activatable antibody or antigen-binding polypeptide) associated with a therapeutic moiety.

In various instances, a therapeutic antibody or antigen-binding polypeptide is activatable. Broadly, an antibody or antigen-binding polypeptide disclosed herein is activatable if the antibody or antigen-binding polypeptide is coupled to a masking moiety (MM) that reduces the ability of the antibody or antigen-binding polypeptide to specifically bind to target epitope when the activatable antibody is in an intact or uncleaved state. In some instances, the MM is coupled via a cleavable moiety (CM) that includes a substrate for a protease, for example, a protease that is active in diseased tissue and/or a protease that is co-localized with the target at a treatment site in a subject. When the activatable antibody or antigen-binding polypeptide is in an "activated" or cleaved state, such as when the CM is cleaved by a protease, the antibody or antigen-binding polypeptide can specifically bind to its target epitope. Activatable antibodies and antigen-binding polypeptides, and methods of producing the same, are described, e.g., in International Publication No. WO 2009/025846 and International Publication No. WO 2010/081173, each of which is incorporated herein by reference in its entirety.

In various embodiments, a masking moiety is a peptide. In various embodiments, an activatable antibody or antigen-binding polypeptide that includes a masking moiety includes an "activation moiety." As used herein, an activation moiety is a moiety that mediates a transition between a non-activated state and activated state of an activatable antibody or antigen-binding polypeptide. As used herein an antibody or antigen-binding polypeptide is "activatable" in that the molecule can exhibit a first "non-activated" level of binding with a target epitope when in a "non-activated" state, and a second greater, "activated" level of binding when the molecule is in an "activated" state. Comparison of binding of an epitope by an activatable antibody or antigen-binding polypeptide in a non-activated state and binding of an epitope by an activated form of an activatable antibody or antigen-binding polypeptide can be made according to any standard of binding described herein or otherwise known in the art. Non-limiting measures of binding include, e.g., a measure according to an immunoabsorbant assay, or any other method of measuring binding as described herein. While it may be the case in certain particular embodiments that an activatable antibody or antigen-binding polypeptide in a non-activated state does not bind, or substantially does not bind, a target epitope, it is to be understood that complete or substantially complete abrogation of binding in a non-activated state is not required. Masking moieties and use thereof are described, e.g., in International Publication No. WO 2009/025846 and International Publication No. WO 2010/081173, each of which is incorporated herein by reference in its entirely.

In various embodiments, an antibody or antigen-binding polypeptide and a masking moiety are joined by a linker. In various embodiments a linker is an activation linker (i.e., a linker that is or includes an activation moiety). In various embodiments, an antibody or antigen-binding polypeptide and a masking moiety are joined by an activation linker that is or includes a cleavable moiety (CM). In certain instances in which an activatable antibody or antigen-binding polypeptide includes a masking moiety joined to an antibody or antigen-binding polypeptide by an activation linker that is or includes a cleavable moiety (a "cleavable linker"), a masking moiety can inhibit ability of an antibody or antigen-binding polypeptide to bind a target epitope when the cleavable linker is in an uncleaved state, which inhibition is relieved if the cleavable linker is cleaved. Accordingly, in certain instances, cleavage of a cleavable moiety relieves inhibition by a masking moiety of ability of an antibody or antigen-binding polypeptide to bind a target epitope. Linkers and use thereof are described, e.g., in International Publication No. WO 2009/025846 and International Publication No. WO 2010/081173, each of which is incorporated herein by reference in its entirety.

In various embodiments, without limitation, a masking moiety can be a moiety that binds a binding moiety of an activatable antibody or antigen-binding polypeptide. In various embodiments, without limitation, a masking moiety can sterically inhibit ability of an antibody or antigen-binding polypeptide to bind a target epitope. In various embodiments, without limitation, a masking moiety can allosterically inhibit ability of an antibody or antigen-binding polypeptide to bind a target epitope.

In certain instances an activation linker is or includes a substrate capable of being specifically cleaved by an enzyme, protease, or peptidase. In certain instances, an activation linker is reducible by a reducing agent. In certain instances, an activation linker is a photo-sensitive substrate, photolysis of which relieves inhibition by a masking moiety of ability of an antibody or antigen-binding polypeptide to bind a target epitope. As used herein cleavage is used interchangeably to denote activation by an enzyme, a reducing agent, or photolysis. It is also contemplated that a cleavable linker and a masking moiety can overlap in amino acid sequence, e.g., such that a cleavable linker is contained within a masking moiety. Cleavable linkers and use thereof are described, e.g., in International Publication No. WO 2009/025846 and International Publication No. WO 2010/081173, each of which is incorporated herein by reference in its entirety.

In various embodiments, an activatable antibody or antigen-binding polypeptide includes an activation moiety that mediates a transition between a non-activated state and activated state of an activatable antibody or antigen-binding polypeptide by undergoing, causing, or contributing to a conformation change in a masking moiety, or other conformational change in an activatable antibody or antigen-binding polypeptide, that relieves inhibition by a masking moiety of ability of an antibody or antigen-binding polypeptide to bind a target epitope. In various embodiments, access of a binding partner to the functional protein is greater in the presence of an enzyme/reducing agent/light capable of activating an activation linker than in the absence of activation and/or of such enzyme/reducing agent/light. Activation moieties and use thereof are described, e.g., in International Publication No. WO 2009/025846 and International Publication No. WO 2010/081173, each of which is incorporated herein by reference in its entirety.

An activation moiety included in an activatable antibody or antigen-binding polypeptide can, in certain embodiments, be selected based on in vivo or in vitro localization (e.g., within or among cells, tissues, organs, or subjects) of a protease for cleavage of the activation moiety and/or activation of the activatable antibody or antigen-binding polypeptide. For example, proteases expressed in certain tissues (e.g., cancerous tissues) include, without limitation, matrix metalloprotease (MMP), ADAM 17, BMP-1, a cysteine protease (e.g., cathepsin), HtrA1, legumain, matriptase (MT-SP1), neutrophil elastase, TMPRSS (e.g., TMPRSS3 or TMPRSS4), thrombin, or u-type plasminogen activator (uPA, also referred to as urokinase). Thus, in particular instances, an activation moiety can be or include a substrate of a protease selected from matrix metalloprotease (MMP), ADAM 17, BMP-1, a cysteine protease (e.g., cathepsin), HtrA1, legumain, matriptase (MT-SP1), neutrophil elastase, TMPRSS (e.g., TMPRSS3 or TMPRSS4), thrombin, or u-type plasminogen activator (uPA, also referred to as urokinase). In various instances, protease consensus target sequences are known in the art.

An activatable antibody or antigen-binding polypeptide can be provided in any of a variety of structural configurations. For instance, it is contemplated that an antibody or antigen-binding polypeptide, masking moiety, and cleavable linker may be provided in that order as read from N-terminus to C-terminus, or as read from C-terminus to N-terminus.

Non-limiting examples of configurations of an activatable antibody or antigen-binding polypeptide include (from N-terminus to C-terminus): (a) [masking moiety]-[linker]-[antibody or antigen-binding polypeptide]; (b) [antibody or antigen-binding polypeptide]-[linker]-[masking moiety]; (c) [masking moiety]-[activation linker]-[antibody or antigen-binding polypeptide]; and/or (d) [antibody or antigen-binding polypeptide]-[activation linker]-[masking moiety]; (e)

[masking moiety]-[antibody or antigen-binding polypeptide]; (f) [antibody or antigen-binding polypeptide]-[masking moiety];

While a masking moiety and a linker are represented in certain provided configurations as distinct components, it is to be understood that an amino acid sequence of a masking moiety and an amino acid sequence of a linker can, in at least some instances, overlap, e.g., such that the sequence of a cleavable linker is completely or partially within an amino acid sequence of a masking moiety. It is also to be understood that configurations provided herein are also contemplated in the orientation of C-terminus to N-terminus. Configurations of activatable antibodies and antigen-binding polypeptides are described, e.g., in International Publication No. WO 2009/025846 and International Publication No. WO 2010/081173, each of which is incorporated herein by reference in its entirety.

A therapeutic antibody or antigen-binding polypeptide (such as, without limitation, an activatable antibody or antigen-binding polypeptide) is associated with a therapeutic moiety.

In various embodiments of the present invention, an therapeutic antibody or antigen-binding polypeptide of the present invention is associated with a therapeutic moiety. In various instances, an therapeutic antibody or antigen-binding polypeptide as disclosed herein can be covalently or non-covalently associated with a therapeutic moiety. In various instances, an therapeutic antibody or antigen-binding polypeptide as disclosed herein can be directly or indirectly associated with a therapeutic moiety. In various instances, an therapeutic antibody or antigen-binding polypeptide as disclosed herein can be associated with a therapeutic moiety via a linker. In various instances, an therapeutic antibody or antigen-binding polypeptide as disclosed herein can be fused or conjugated with a therapeutic moiety. In various instances, an therapeutic antibody or antigen-binding polypeptide as disclosed herein is associated with a therapeutic moiety via a polypeptide terminus of the therapeutic antibody or antigen-binding polypeptide. In various instances, an therapeutic antibody or antigen-binding polypeptide as disclosed herein is associated with a therapeutic moiety via a non-terminal residue of the therapeutic antibody or antigen-binding polypeptide. In various instances, an therapeutic antibody or antigen-binding polypeptide as disclosed herein is associated with a therapeutic moiety via incorporation of the therapeutic moiety into the molecular structure of the therapeutic antibody or antigen-binding polypeptide. In various instances, an therapeutic antibody or antigen-binding polypeptide as disclosed herein can be associated with a plurality of same or different therapeutic moieties via any mechanism disclosed herein or otherwise known in the art, which same or different therapeutic moieties can be associated with the therapeutic antibody or antigen-binding polypeptide via same or different mechanisms of association as disclosed herein or otherwise known in the art.

Therapeutic moieties of the present invention include drugs, e.g., a drug for treatment of a condition nor disease. Therapeutic moieties of the present invention include, without limitation, a cytotoxic moiety, chemotherapeutic agent, toxin, or radionuclide.

In various embodiments, a chemotherapeutic agent includes pro-apoptotic, cytostatic and/or cytotoxic agents, for example specifically including agents utilized and/or recommended for use in treating one or more diseases, disorders or conditions associated with undesirable cell proliferation. In certain embodiments, chemotherapeutic agents are useful in the treatment of cancer. In some embodiments, a chemotherapeutic agent may be or include one or more one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more *vinca* alkaloids, and/or one or more analogs of one or more of the following (i.e., that share a relevant anti-proliferative activity). In some particular embodiments, a chemotherapeutic agent may be or comprise one or more of Actinomycin, all-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIBO15, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments, a chemotherapeutic agent can be or include one or more of farnesyl-thiosalicylic acid (FTS), 4-(4-Chloro-2-methylphenoxy)-N-hydroxybutanamide (CMH), estradiol (E2), tetramethoxystilbene (TMS), 6-tocatrienol, salinomycin, or curcumin Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

The present invention further includes a method of producing an anti-CD166 ICD antibody or antigen-binding polypeptide disclosed herein. A method of producing an anti-CD166 ICD antibody or antigen-binding polypeptide as disclosed herein can include producing a cell including a nucleic acid encoding an anti-CD166 ICD antibody or antigen-binding polypeptide as disclosed herein. The nucleic acid can be, e.g., present in the genome of the cell and/or present in a vector for expression of an antibody or antigen-binding polypeptide. A method of the present invention can further include culturing a cell including a nucleic acid encoding an anti-CD166 ICD antibody or antigen-binding polypeptide as disclosed herein under conditions that permit cell growth and/or cell division, production of an anti-CD166 ICD antibody or antigen-binding polypeptide as disclosed herein, or both. A method of the present invention can further include isolating an anti-CD166 ICD antibody or antigen-binding polypeptide as disclosed herein from a cell culture. Methods of producing nucleic acids, producing cells, culturing cells, and isolating antibodies from culture are known in the art.

Formulation of Anti-CD166 ICD Antibody or Antigen-Binding Polypeptide

In various embodiments, an anti-CD166 ICD antibody or antigen-binding polypeptide described herein can be, or be included in, a pharmaceutical composition. Such a pharmaceutical composition can be useful, e.g., in detection of CD166, diagnosis of a condition associated with CD166, treatment of a condition associated with CD166, identification of antibodies that bind CD166 or a portion thereof (e.g., an intracellular portion thereof or an extracellular portion thereof), or other uses. Compositions including an anti-CD166 ICD antibody or antigen-binding polypeptide can be formulated by methods known to those skilled in the art (e.g., according to techniques and/or formulations described in Remington's Pharmaceutical Sciences, 17th edition, ed. Alfonso R. Gennaro, Mack Publishing Company, Easton, Pa. (1985)).

In various instances, an anti-CD166 ICD antibody or antigen-binding polypeptide composition can be formulated to include an acceptable carrier or excipient, e.g., a carrier or excipient suitable for laboratory use, a carrier or excipient suitable for in vitro use, or a pharmaceutically acceptable carrier or excipient. Examples of carriers include, without limitation, any and all solvents, dispersion media, coatings, antibacterial and antifungal agents, isotonic and absorption delaying agents, and the like that are physiologically compatible. Compositions of the present invention can include a salt, e.g., a pharmaceutically acceptable salt, e.g., an acid addition salt or a base addition salt.

Selection or use of any particular form may depend, in part, on the intended mode application. In various embodiments, an anti-CD166 ICD antibody or antigen-binding polypeptide can be formulated as, or in a manner appropriate to use as, a laboratory reagent or reagent for in vitro use. In various embodiments, an anti-CD166 ICD antibody or antigen-binding polypeptide will be formulated in a liquid form.

In various embodiments, a composition including an antibody as described herein, e.g., a sterile formulation, can be formulated in accordance with conventional practices, e.g., using distilled water as a carrier. Suitable carriers can include, without limitation, physiological saline or an isotonic solution containing glucose and other supplements such as D-sorbitol, D-mannose, D-mannitol, and sodium chloride, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

As disclosed herein, an anti-CD166 ICD antibody or antigen-binding polypeptide composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

In various embodiments, a composition of the present invention can be formulated as a solution, microemulsion, dispersion, liposome, or other ordered structure suitable for stable storage at high concentration. Solutions can be prepared by incorporating a composition described herein in the required amount in an appropriate solvent with one or a combination of ingredients enumerated above, optionally followed by filter sterilization. Generally, dispersions are prepared by incorporating a composition described herein into a sterile vehicle that contains a basic dispersion medium and the required other ingredients from those enumerated above. In the case of powder forms, e.g., sterile powders, methods for preparation include vacuum drying and freeze-drying that yield a powder of a composition described herein plus any additional desired ingredient (e.g., as described herein). In particular instances, proper fluidity of a solution can be maintained, for example, by the use of a coating such as lecithin, by the maintenance of the required particle size in the case of dispersion and by the use of surfactants. A composition described herein can include monostearate salts or gelatin.

An anti-CD166 ICD antibody or antigen-binding polypeptide composition can be formulated by suitably combining the anti-CD166 ICD antibody or antigen-binding polypeptide with one or more vehicles or media, such as sterile water, physiological saline, vegetable oil, emulsifier, suspension agent, surfactant, stabilizer, flavoring excipient, diluent, vehicle, preservative, binder, optionally in a concentration suitable to an intended use. Other items that may be included are a buffer such as a phosphate buffer, or sodium acetate buffer, a stabilizer such as benzyl alcohol or phenol, and an antioxidant.

An anti-CD166 ICD antibody or antigen-binding polypeptide composition can be packaged in a suitable ampule or other suitable packaging, e.g., for laboratory use.

In some embodiments, an anti-CD166 ICD antibody or antigen-binding polypeptide composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

In particular instances, an anti-CD166 ICD antibody or antigen-binding polypeptide composition can be formulated as a solution. In some embodiments, a composition can be formulated, for example, as a buffered solution at a suitable concentration and suitable for storage at 2-8° C. (e.g., 4° C.).

In various embodiments, an anti-CD166 ICD antibody or antigen-binding polypeptide composition as described herein can further included a secondary antibody. A secondary antibody to anti-CD166 ICD antibody or antigen-binding polypeptide can be present in a separate secondary antibody formulation from anti-CD166 ICD antibody or antigen-binding polypeptide, which secondary antibody formulation can be prepared, e.g., according to the manner described herein for an anti-CD166 ICD antibody or antigen-binding polypeptide composition or formulation.

In various embodiments, an anti-CD166 ICD antibody or antigen-binding polypeptide, upon contacting anti-CD166 ICD antibody or antigen-binding polypeptide with CD166 and/or a CD166 epitope of the anti-CD166 ICD antibody or antigen-binding polypeptide, anti-CD166 ICD antibody or antigen-binding polypeptide will bind CD166. The present invention includes compositions in which anti-CD166 ICD antibody or antigen-binding polypeptide is bound with CD166, e.g., via a CD166 epitope of anti-CD166 ICD antibody or antigen-binding polypeptide. In various such instances, CD166 can be mammalian CD166, e.g., primate CD166, e.g., human CD166.

In various embodiments, an anti-CD166 ICD antibody or antigen-binding polypeptide is contacted with a secondary antibody that binds or is capable of binding anti-CD166 ICD antibody or antigen-binding polypeptide. The present invention includes compositions in which anti-CD166 ICD antibody or antigen-binding polypeptide is bound by a secondary antibody. The present invention further includes particular embodiments in which anti-CD166 ICD antibody or antigen-binding polypeptide is bound with CD166, e.g., via a CD166 epitope of anti-CD166 ICD antibody or antigen-binding polypeptide, and anti-CD166 ICD antibody or antigen-binding polypeptide is bound by a secondary antibody.

The present invention includes a nucleic acid encoding anti-CD166 ICD antibody or antigen-binding polypeptide as disclosed herein. Nucleic acid sequences encoding an anti-CD166 ICD antibody or antigen-binding polypeptide are disclosed herein, any of which may be present or included in a composition of the present invention. A nucleic acid molecule of the present invention can be a nucleic acid molecule encoding, alone or among other encoded elements, an anti-CD166 ICD antibody or antigen-binding polypeptide. A nucleic acid molecule of the present invention can be a linear nucleic acid, plasmid, or vector. In certain instances, an anti-CD166 ICD antibody or antigen-binding polypeptide composition is a nucleic acid in solution, such as a linear nucleic acid, plasmid, or vector in solution. Solutions for storage of nucleic acid reagents are known in the art. Numerous plasmids and vectors are known in the art. For example, a vector including a nucleic acid sequence encoding an anti-CD166 ICD antibody or antigen-binding polypeptide can be an expression vector, e.g., a vector for expression of an antibody or antigen-binding polypeptide.

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994). Various techniques are known in the art for construction of an expression vector containing a nucleic acid that encodes an antibody or polypeptide. Known methods can be used to construct expression vectors containing antibody or polypeptide coding sequences together with appropriate transcriptional and translational control signals. These methods include, for example, in vitro recombinant DNA techniques, synthetic techniques, and in vivo genetic recombination. In certain embodiments, an expression vector can be transferred to a host cell by conventional techniques. Cells including an expression vector can be cultured by conventional techniques to produce antibodies or polypeptides.

The present invention includes a cell that includes a nucleic acid molecule encoding an anti-CD166 ICD antibody or antigen-binding polypeptide as disclosed herein. In various embodiments, the cell is a eukaryotic cell, mammalian cell, fungal cell, or bacterial cell. In certain embodiments, a cell is an *E. coli* cell, yeast cell, fly cell, primate cell, or human cell. In various embodiments, a cell is a cell for expression of anti-CD166 ICD antibody or antigen-binding polypeptide. In certain instances, a cell is a cell of a line selected from HEK293T, HEK293E, HEK293F, CHO, CHO DG44, CHO-K1, and NSO. Cells of the present invention can be present in any storage of culture media known in the art. Cells of the present invention can therefore be, e.g., active cells in culture or frozen cells.

Formulation of Therapeutic Agents Used or Included with an Anti-CD166 ICD Antibody or Antigen-Binding Polypeptide In various instances, an anti-CD166 ICD antibody or antigen-binding polypeptide with be provided for use in conjunction with a therapeutic agent. For example, in particular instances, an anti-CD166 ICD antibody or antigen-binding polypeptide is provided for a diagnostic use in conjunction with administration, or optional administration as needed, of a therapeutic agent.

With respect to kits of the present invention including a therapeutic agent, a therapeutic agent can be provided in the form of a pharmaceutical composition. Such a pharmaceutical therapeutic agent composition can be useful, e.g., for the prevention and/or treatment of a condition or disease. Therapeutic agent compositions can be formulated by methods known to those skilled in the art (e.g., as described in Remington's Pharmaceutical Sciences, 17th edition, ed. Alfonso R. Gennaro, Mack Publishing Company, Easton, Pa. (1985)).

A suitable means of administration can be selected based on the condition or disease to be treated and upon the age and condition of a subject. A single dose of therapeutic agent composition can be selected, without limitation, from a range of 0.001 to 1000 mg/kg of body weight. A single dose of therapeutic agent composition can be selected, without limitation, from a range of 0.001 to 100000 mg/kg of body weight. Dose and method of administration can vary depending on the weight, age, condition, and the like of a patient, and can be suitably selected as needed by those skilled in the art.

In various instances, a therapeutic agent composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present invention can include a pharmaceutically acceptable salt, e.g., an acid addition salt or a base addition salt.

In various embodiments, a composition including a therapeutic agent as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

As disclosed herein, a therapeutic agent composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, a therapeutic agent composition can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

A parenteral route of administration can be, for example, administration by injection, transnasal administration, transpulmonary administration, or transcutaneous administration. Administration can be systemic or local by intravenous injection, intramuscular injection, intraperitoneal injection, subcutaneous injection.

In various embodiments, a therapeutic agent composition of the present invention can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

A therapeutic agent composition can be administered parenterally in the form of an injectable formulation comprising a sterile solution or suspension in water or another pharmaceutically acceptable liquid. For example, the therapeutic agent composition can be formulated by suitably combining the therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of therapeutic agent included in the pharmaceutical preparations is such that a suitable dose within the designated range is provided. Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

In some embodiments, a therapeutic agent composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

In particular instances, a therapeutic agent composition can be formulated as a solution. In some embodiments, a composition can be formulated, for example, as a buffered solution at a suitable concentration and suitable for storage at 2-8° C. (e.g., 4° C.).

Compositions including a therapeutic agent as described herein can be formulated in immunoliposome compositions. Such formulations can be prepared by methods known in the art. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art. Dry powder inhaler formulations and suitable systems for administration of the formulations are also known in the art. Pulmonary administration may be oral and/or nasal. Examples of pharmaceutical devices for pulmonary delivery include metered dose inhalers, dry powder inhalers (DPIs), and nebulizers. For example, a composition described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TURBOHALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition described herein can be intrapulmonarily administered by way of a metered dose inhaler. These inhalers rely on a propellant to deliver a discrete dose of a compound to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, therapeutic agent compositions can be formulated for delivery to the eye, e.g., in the form of a pharmaceutically acceptable solution, suspension or ointment. A preparation for use in treating an eye can be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents. A preparation as described herein can be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreal cavity of the eye may be appropriate, in certain embodiments, for administration of a composition as described herein. For example, U.S. Publication No. 2002/0026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a transscleral patch and delivery via contact lenses) for delivery of a therapeutic agent to the eye are described in, e.g., Ambati and Adamis (2002) Prog Retin Eye Res 21(2):145-151; Ranta and Urtti (2006) Adv Drug Delivery Rev 58(11): 1164-1181; Barocas and Balachandran (2008) Expert Opin Drug Delivery 5(1): 1-10(10); Gulsen and Chauhan (2004) Invest Opthalmol Vis Sci 45:2342-2347; Kim et al. (2007) Ophthalmic Res 39:244-254; and PCT publication no. WO 04/073551, the disclosures of which are incorporated herein by reference in their entirety.

In various embodiments, subcutaneous administration can be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with antibody drug for subcutaneous injection.

In some embodiments, a therapeutic agent composition described herein can be therapeutically delivered to a subject by way of local administration. As used herein, "local administration" or "local delivery," can refer to delivery that does not rely upon transport of the therapeutic agent composition or therapeutic agent to its intended target tissue or site via the vascular system. For example, the therapeutic agent composition may be delivered by injection or implantation of the composition or agent or by injection or implantation of a device containing the composition or agent. In certain embodiments, following local administration in the vicinity of a target tissue or site, the composition or agent, or one or more components thereof, may diffuse to an intended target tissue or site that is not the site of administration.

In some embodiments, the compositions provided herein are present in unit dosage form, which unit dosage form can be suitable for self-administration. Such a unit dosage form may be provided within a container, typically, for example, a vial, cartridge, prefilled syringe or disposable pen. A doser such as the doser device described in U.S. Pat. No. 6,302,855, may also be used, for example, with an injection system as described herein.

A suitable dose of a therapeutic agent composition described herein, which dose is capable of treating or preventing a disorder in a subject, can depend on a variety of factors including, e.g., the age, sex, and weight of a subject to be treated, the condition or disease to be treated, and the particular therapeutic agent used. Other factors affecting the dose administered to the subject include, e.g., the type or severity of the condition or disease. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject can also be adjusted based upon the judgment of a medical practitioner.

A therapeutic agent composition described herein can be administered as a fixed dose, or in a milligram per kilogram (mg/kg) dose. While in no way intended to be limiting, exemplary dosages of an antibody therapeutic agent include, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition described herein include, without limitation, 0.1 mg/kg, 0.5 mg/kg, 1.0 mg/kg, 2.0 mg/kg, 4 mg/kg, 8 mg/kg, or 20 mg/kg.

A therapeutic agent solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount can be an amount at which any toxic or detrimental effects of the composition are outweighed by therapeutically beneficial effects.

Kits

The present invention includes a kit including one or more of (a) an anti-CD166 ICD antibody or antigen-binding polypeptide; (b) one or more reagents for use in a technique capable of detecting binding of CD166 by an anti-CD166 ICD antibody or antigen-binding polypeptide; (c) a therapeutic agent; (d) one or more reagents for use in administration of therapeutic antibody or antigen-binding polypeptide (c) instructions for a technique capable of detecting binding of CD166 by an anti-CD166 ICD antibody or antigen-binding polypeptide; and/or (d) instructions for administering a therapeutic antibody or antigen-binding polypeptide to a subject.

In various embodiments, a kit of the present invention can include any anti-CD166 ICD antibody or antigen-binding polypeptide disclosed herein. In particular embodiments, an anti-CD166 ICD antibody or antigen-binding polypeptide is an anti-CD166 ICD antibody or antigen-binding polypeptide associated with a detectable moiety. In particular embodiments, an anti-CD166 ICD antibody or antigen-binding polypeptide is an anti-CD166 ICD antibody or antigen-binding polypeptide associated with a therapeutic moiety.

In various embodiments, a kit of the present invention can include one or more reagents for use in a technique capable of detecting binding of CD166 by an anti-CD166 ICD antibody or antigen-binding polypeptide as disclosed herein or known in the art.

In certain instances, a reagent for use in a technique capable of detecting binding of CD166 by an anti-CD166 ICD antibody or antigen-binding polypeptide is a secondary antibody. In certain non-limiting examples, an anti-CD166 ICD antibody or antigen-binding polypeptide is a human anti-CD166 ICD antibody or antigen-binding polypeptide and the secondary antibody is an anti-human secondary antibody. In certain non-limiting examples, an anti-CD166 ICD antibody or antigen-binding polypeptide is a mouse anti-CD166 ICD antibody or antigen-binding polypeptide and the secondary antibody is an anti-mouse secondary antibody. In certain non-limiting examples, an anti-CD166 ICD antibody or antigen-binding polypeptide is a rabbit anti-CD166 ICD antibody or antigen-binding polypeptide and the secondary antibody is an anti-rabbit secondary antibody. In certain non-limiting examples, an anti-CD166 ICD antibody or antigen-binding polypeptide is a hamster anti-CD166 ICD antibody or antigen-binding polypeptide and the secondary antibody is an anti-hamster secondary antibody. In certain non-limiting examples, an anti-CD166 ICD antibody or antigen-binding polypeptide is a goat anti-CD166 ICD antibody or antigen-binding polypeptide and the secondary antibody is an anti-goat secondary antibody. In certain non-limiting examples, an anti-CD166 ICD antibody or antigen-binding polypeptide is a sheep anti-CD166 ICD antibody or antigen-binding polypeptide and the secondary antibody is an anti-sheep secondary antibody. In certain non-limiting examples, an anti-CD166 ICD antibody or antigen-binding polypeptide is a horse anti-CD166 ICD antibody or antigen-binding polypeptide and the secondary antibody is an anti-horse secondary antibody. In certain non-limiting examples, an anti-CD166 ICD antibody or antigen-binding polypeptide is a guinea pig anti-CD166 ICD antibody or antigen-binding polypeptide and the secondary antibody is an anti-guinea pig secondary antibody. In certain non-limiting examples, an anti-CD166 ICD antibody or antigen-binding polypeptide is a chicken anti-CD166 ICD antibody or antigen-binding polypeptide and the secondary antibody is an anti-chicken secondary antibody.

In certain instances, a reagent for use in a technique capable of detecting binding of CD166 by an anti-CD166 ICD antibody or antigen-binding polypeptide is a nuclei staining reagent. In certain instances, a reagent for use in a technique capable of detecting binding of CD166 by an anti-CD166 ICD antibody or antigen-binding polypeptide is a blocking buffer. In certain instances, a reagent for use in a technique capable of detecting binding of CD166 by an anti-CD166 ICD antibody or antigen-binding polypeptide is a wash buffer. In certain instances, a reagent for use in a technique capable of detecting binding of CD166 by an anti-CD166 ICD antibody or antigen-binding polypeptide is a mounting medium. In various instances in which a detectable moiety is an enzyme, a kit of the present invention can include a substrate of the enzyme as a reagent for use in a technique capable of detecting binding of CD166 by an anti-CD166 ICD antibody or antigen-binding polypeptide. In various instances in which a detectable moiety is an enzyme substrate, a kit of the present invention can include an enzyme that interacts with the substrate as a reagent for use in a technique capable of detecting binding of CD166 by an anti-CD166 ICD antibody or antigen-binding polypeptide.

In various embodiments, a kit of the present invention can include a therapeutic agent, e.g., a therapeutic antibody or antigen-binding polypeptide. In certain instances, a therapeutic antibody or antigen-binding polypeptide is an activatable antibody or antigen-binding polypeptide. In certain instances, a therapeutic antibody or antigen-binding polypeptide is a therapeutic antibody or antigen-binding polypeptide (e.g., an activatable antibody or antigen-binding polypeptide) that is associated with a therapeutic moiety.

In certain instances, a therapeutic antibody or antigen-binding polypeptide is a therapeutic anti-CD166 antibody or antigen-binding polypeptide. In certain instances, a therapeutic anti-CD166 antibody or antigen-binding polypeptide is an activatable antibody or antigen-binding polypeptide. In particular embodiments, a therapeutic anti-CD166 antibody or antigen-binding polypeptide is an anti-CD166 antibody or antigen-binding polypeptide (and/or an anti-CD166 activatable antibody or antigen-binding polypeptide) associated with a therapeutic moiety.

In certain instances, a therapeutic antibody or antigen-binding polypeptide is a therapeutic antibody or antigen binding polypeptide that specifically binds to an immune checkpoint protein. In certain instances, a therapeutic antibody or antigen-binding polypeptide is an anti-PD-1 antibody or antigen-binding polypeptide. In certain instances, a therapeutic anti-PD-1 antibody or antigen-binding polypeptide is an activatable antibody or antigen-binding polypeptide. In particular embodiments, a therapeutic anti-PD-1 antibody or antigen-binding polypeptide is an anti-PD-1 antibody or antigen-binding polypeptide (and/or an anti-PD-1 activatable antibody or antigen-binding polypeptide) associated with a therapeutic moiety. In certain instances, a therapeutic antibody or antigen-binding polypeptide is an anti-PD-L1 antibody or antigen-binding polypeptide. In certain instances, a therapeutic anti-PD-L1 antibody or antigen-binding polypeptide is an activatable antibody or antigen-binding polypeptide. In particular embodiments, a therapeutic anti-PD-L1 antibody or antigen-binding polypeptide is an anti-PD-L1 antibody or antigen-binding polypeptide (and/or an anti-PD-L1 activatable antibody or antigen-binding polypeptide) associated with a therapeutic moiety.

EXAMPLES

The following Examples demonstrate, among other things, identification, sequences, and application of certain anti-CD166 ICD antibodies or antigen-binding polypeptides as disclosed herein.

Example 1: Generation and Characterization of Anti-Human CD166 Antibodies

Studies provided herein were designed to generate certain anti-human CD166 (hCD166) mouse monoclonal antibodies of the present disclosure. Anti-hCD166 antibodies presented herein were generated against human CD166 in mice. Those of ordinary skill in the art appreciate the difficulty in raising anti-hCD166 antibodies in mice.

The anti-hCD166 mouse monoclonal antibodies of the present disclosure were obtained using mouse hybridoma technology. Two peptides derived from the C-terminal intracellular domain of human CD166 were conjugated to keyhole limpet hemocyanin (KLH) using maleimide chemistry. The two peptides corresponded to amino acid residues 550 to 569 (YMKKSKTASKHVNKDLGNME; "Peptide A"; SEQ ID NO: 64) and amino acid resides 565 to 583 (LGNMEENKKLEENNHKTEA; "Peptide B"; SEQ ID NO: 66) of human CD166. Each peptide also included an additional N-terminal cysteine residue to allow maleimide conjugation. In a first round, five mice were each immunized with both peptides. Three additional mice were later immunized in a second round with reduced amounts of the peptide antigens.

Of the five mice immunized in the first round, one mouse (Mouse #1) was assayed by a tailbleed screen to determine its antibody titer to both of the target peptides. Titer was determined by ELISA (100 ng/well of peptide A or B with 0.9 mg/mL BSA). The results of the first tailbleed of Mouse #1 are shown below in Table 1.

TABLE 1

ELISA of Mouse #1 First Tailbleed

| Sample (Dilution) | Peptide A $A_{620}$ | Peptide B $A_{620}$ |
|---|---|---|
| Mouse #1 serum (1:1,000) | 1.367 | 2.961 |
| Mouse #1 serum (1:3,000) | 0.541 | 2.687 |
| Mouse #1 serum (1:10,000) | 0.151 | 1.410 |
| Mouse #1 serum (1:30,000) | 0.103 | 0.597 |
| Mouse #1 serum (1:100,000) | 0.062 | 0.169 |
| Negative control* | 0.062 | 0.056 |

*Negative control = naïve serum (1:1,000) in 1% milk/PBS

Of the three mice immunized in the second round, two mice (Mice #2 and #3) were assayed by a tailbleed screen to determine antibody titer to each of the target peptides (SEQ ID NO: 64 and SEQ ID NO: 66). Titer was determined by ELISA (200 ng/well of peptides A or B with 0.9 mg/mL BSA). The results of the first tailbleed of the two mice are shown below in Table 2.

TABLE 2

ELISA of Mice #2 and #3 First Tailbleed

| Sample (Dilution) | Peptide A $A_{620}$ | Peptide B $A_{620}$ |
|---|---|---|
| Mouse #2 serum (1:1,000) | 2.956 | 2.585 |
| Mouse #2 serum (1:3,000) | 3.051 | 2.690 |
| Mouse #2 serum (1:10,000) | 2.112 | 2.838 |
| Mouse #2 serum (1:30,000) | 0.608 | 2.957 |
| Mouse #3 serum (1:100,000) | 0.324 | 2.688 |
| Negative control* | 0.137 | 0.058 |
| Positive control** | 3.191 | 3.121 |
| Mouse #3 serum (1:1,000) | 2.959 | 2.880 |
| Mouse #3 serum (1:3,000) | 2.527 | 2.901 |
| Mouse #3 serum (1:10,000) | 1.004 | 2.319 |
| Mouse #3 serum (1:30,000) | 0.332 | 0.867 |
| Mouse #3 serum (1:100,000) | 0.138 | 0.351 |
| Negative control* | 0.079 | 0.062 |
| Positive control** | 3.273 | 3.020 |

*Negative control = naïve serum (1:1,000) in 1% milk/PBS
**Positive control = mouse #1 first tailbleed serum (1:1,000) in 1% milk/PBS Mouse #1 was boosted with reduced dosage of peptide A and B to raise the titer of the antibody. A second tailbleed assay was performed on Mouse #1 to determine its antibody titer against both of the target peptides. Titer was determined by ELISA (100 ng/well of peptides A or B with 0.9 mg/mL BSA). The results of the second tailbleed of Mouse #1 are shown below in Table 3.

TABLE 3

ELISA of Mouse #1 Second Tailbleed

| Sample (Dilution) | Peptide A $A_{620}$ | Peptide B $A_{620}$ |
|---|---|---|
| Mouse #1 serum (1:1,000) | 3.142 | 2.970 |
| Mouse #1 serum (1:3,000) | 1.905 | 2.998 |
| Mouse #1 serum (1:10,000) | 0.584 | 2.194 |
| Mouse #1 serum (1:30,000) | 0.223 | 0.962 |

TABLE 3-continued

ELISA of Mouse #1 Second Tailbleed

| Sample (Dilution) | Peptide A $A_{620}$ | Peptide B $A_{620}$ |
|---|---|---|
| Mouse #1 serum (1:100,000) | 0.098 | 0.311 |
| Negative control* | 0.063 | 0.056 |
| Positive control** | 3.087 | 2.952 |

*Negative control = naïve serum (1:1,000) in 3% milk/PBS
**Positive control = mouse #1 first tailbleed serum (1:1,000) in 3% milk/PBS B cells from each of Mouse #2 and Mouse #3 were fused in a combined manner to generate hybridomas in accordance with methods known in the art. Hybridomas were cloned and ~1100 clone supernatants were screened against the each of the human CD166-derived peptides using a Direct EIA format using a goat anti-IgG gamma chain-specific secondary antibody coupled to horseradish peroxidase (HRP) (Millipore, Cat. No. AP503P. Following the initial screen, 136 clones were selected for a further confirmatory screen, of which forty (40) were selected for expansion. The expanded clones were assayed for mouse IgG levels using anti-mouse sensors in an Octet RED96 system (Pall ForteBio) and ELISA (200 ng/well of peptides A or B with 0.9 mg/mL BSA). Candidates included Ab1 (also referred to herein as "Example anti-CD166 ICD antibody 1"), Ab2 (also referred to herein as "Example anti-CD166 ICD antibody 2"), Ab3, Ab4, Ab5, Ab6, Ab7, and Ab8. Five candidates (Ab1, Ab2, Ab3, Ab4, and Ab5) shown below in Table 4 were selected.

TABLE 4

ELISA and IgG expression of Expanded Hybridoma Clone Supernatents

| Sample | Peptide A $A_{620}$ | Peptide B $A_{620}$ | IgG (pg/mL) |
|---|---|---|---|
| Ab1 | 0.162 | 3.234 | 24.2 |
| Ab2 | 0.067 | 3.025 | 39.2 |
| Ab3 | 3.205 | 0.059 | 13.6 |
| Ab4 | 0.057 | 3.068 | 38.2 |
| Ab5 | 0.071 | 2.971 | 53.7 |
| Negative control* | 0.063 | 0.056 | N/A |
| Positive control** | 3.087 | 2.952 | N/A |
| IgG control (25 µg/mL) | N/A | N/A | 25.5 |

*Negative control = growth medium (1:1,000) in 1% milk/PBS
**Positive control = mouse #1 cardiac serum (1:1,000) in 1% milk/PBS Two of the candidate antibodies were sequenced. Representative sequences are as follows:

Ab2 Light Chain; Amino Acid sequence (N-C): SEQ ID NO: 32

Ab2 Light Chain; Nucleotide sequence (5'-3'): SEQ ID NO: 37

Ab2 Light Chain; Nucleotide sequence (5'-3'): SEQ ID NO: 72

Ab2 Heavy Chain; Amino Acid sequence (N-C): SEQ ID NO: 22

Ab2 Heavy Chain; Nucleotide sequence (5'-3'): SEQ ID NO: 27

Ab2 Heavy Chain; Nucleotide sequence (5'-3'): SEQ ID NO: 71

Ab1 Light Chain; Amino Acid sequence (N-C): SEQ ID NO: 12

Ab1 Light Chain; Nucleotide sequence (5'-3'): SEQ ID NO: 17

Ab1 Light Chain; Nucleotide sequence (5'-3'): SEQ ID NO: 70

Ab1 Heavy Chain; Amino Acid sequence (N-C): SEQ ID NO: 2

Ab1 Heavy Chain; Nucleotide sequence (5'-3'): SEQ ID NO: 7

Ab1 Heavy Chain; Nucleotide sequence (5'-3'): SEQ ID NO: 69

Example 2: Screening of Anti-hCD166 Hybridoma Supernatents to Tumor Cell Lines

This Example shows that hybridoma supernatents with anti-hCD166 mouse monoclonal antibodies of the present disclosure can detect human CD166 in human tumor cell lines using immunohistochemical (IHC) staining.

As shown in the exemplary IHC images of FIGS. 1-4, formalin-fixed paraffin-embedded (FFPE) human tumor cell lines (triple-negative breast cancer-derived cell line HCC1806 and breast ductal carcinoma-derived cell line BT-20) were prepared and blocked using standard protocols, and then incubated with the indicated hybridoma supernatents (Ab3, Ab6, Ab2, Ab1, Ab5, Ab7, Ab4, or Ab8 of the present disclosure) at 10 μg/mL IgG for 60 minutes are room temperature. As a control, FFPE samples were also incubated with ABCAM® EPR2759(2)/ab109215 anti-hCD166 rabbit monoclonal antibody at 5 μg/mL. Detection of bound primary antibody was performed by subsequent incubation with biotinylated-conjugated anti-mouse IgG antibody (for the hybridoma supernatents) or biotinylated-conjugated anti-rabbit IgG antibody (for the ABCAM® antibody), followed by addition of avidin-horseradish peroxidase (HRP) (Vectastain Elite ABC HRP Kit, Vector Laboratories) to form the avidin-biotin-HRP complex, followed by addition of a 3,3'-diaminobenzidine substrate (DAB Plus, Dako). Tissues were counterstained with Hematoxylin (Fisher Scientific).

Figure 2:
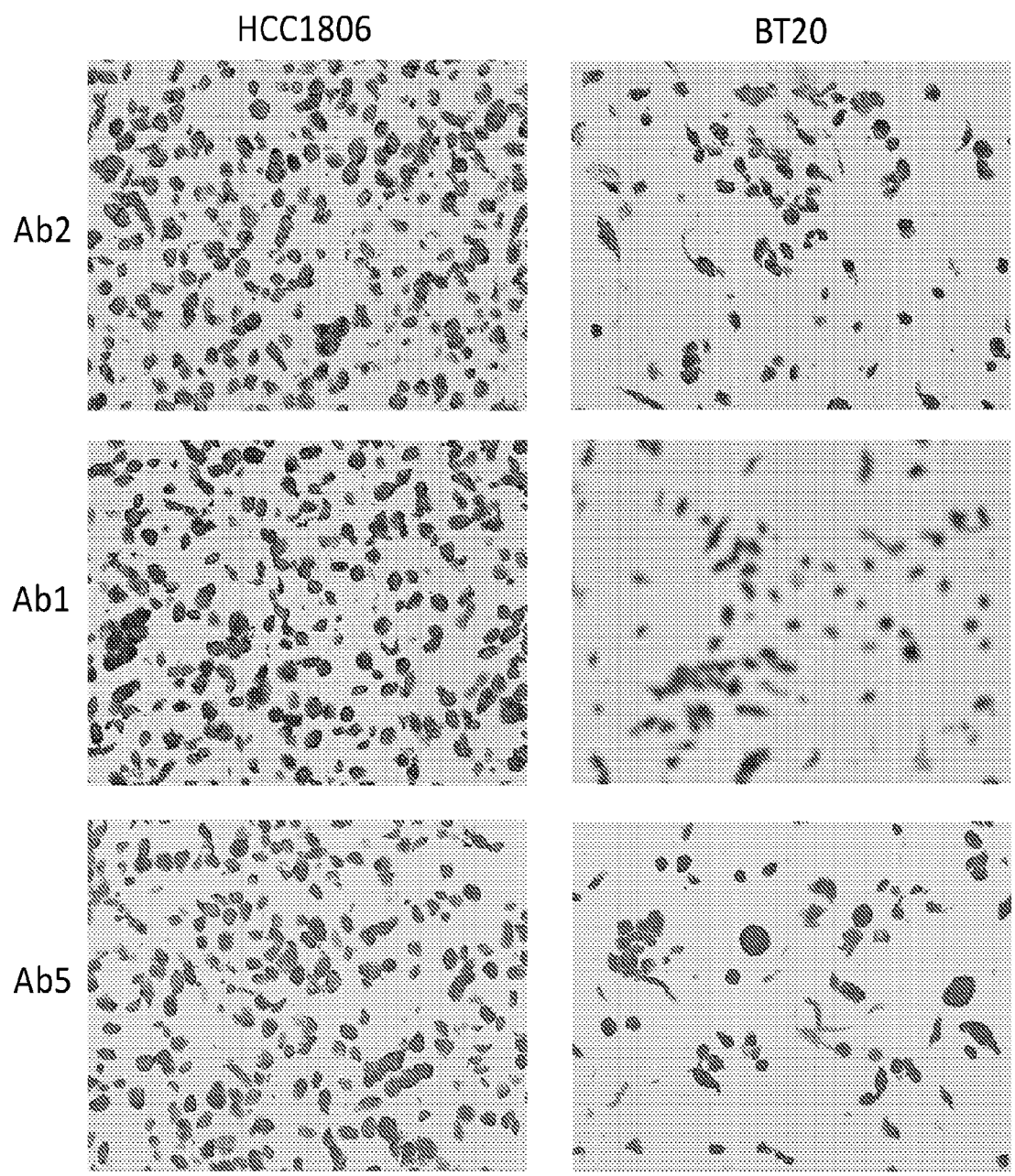
FIG. 2 is a set of IHC images showing formalin-fixed paraffin-embedded (FFPE) human tumor cell lines (HCC1806 and BT20), each having been prepared and blocked using standard protocols and then incubated with supernatant of a hybridoma expressing an indicated mouse monocolonal antibody (Ab2, Ab1, or Ab5).
Figure 3:
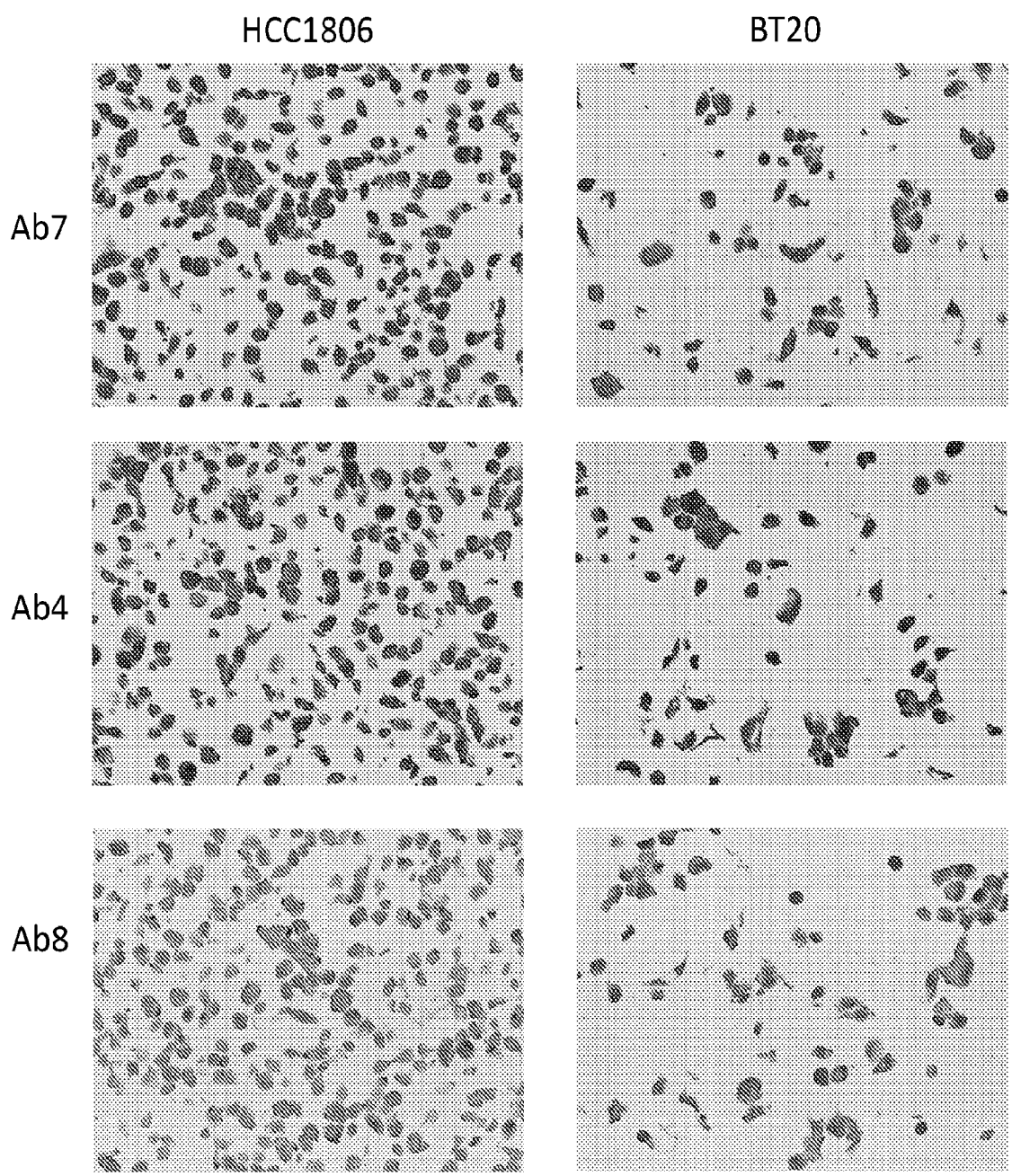
FIG. 3 is a set of IHC images showing formalin-fixed paraffin-embedded (FFPE) human tumor cell lines (HCC1806 and BT20), each having been prepared and blocked using standard protocols and then incubated with supernatant of a hybridoma expressing an indicated mouse monocolonal antibody (Ab7, Ab4, or Ab8).
Figure 4:
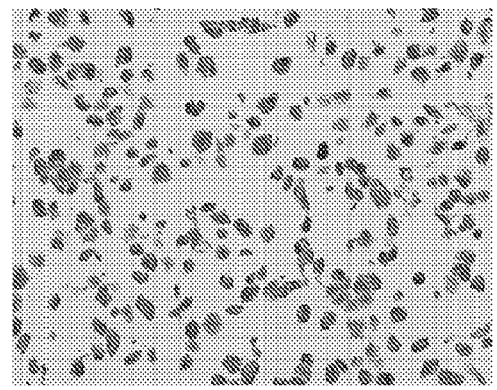
FIG. 4 is a set of IHC images showing formalin-fixed paraffin-embedded (FFPE) human tumor cell lines (HCC1806 and BT20), each having been prepared and blocked using standard protocols and then incubated with media (no primary).
Figure 4:
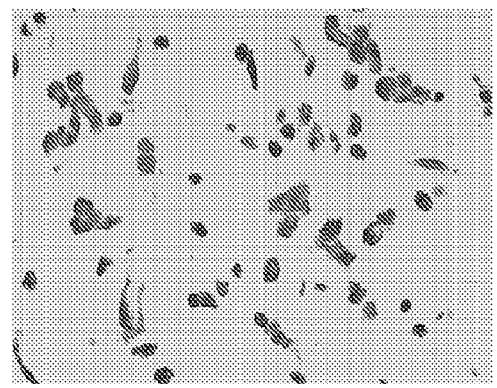
Figure 5:
FIG. 5 is a set of IHC images showing formalin-fixed paraffin-embedded (FFPE) samples of human prostate tissue, having been prepared and blocked using standard protocols and then incubated with 5 µg/mL anti-hCD166 mouse monoclonal antibodies purified from hybridoma supernatants (Ab2 or Ab1) of the present disclosure or ABCAM® EPR2759(2)/ab109215.
Figure 5:
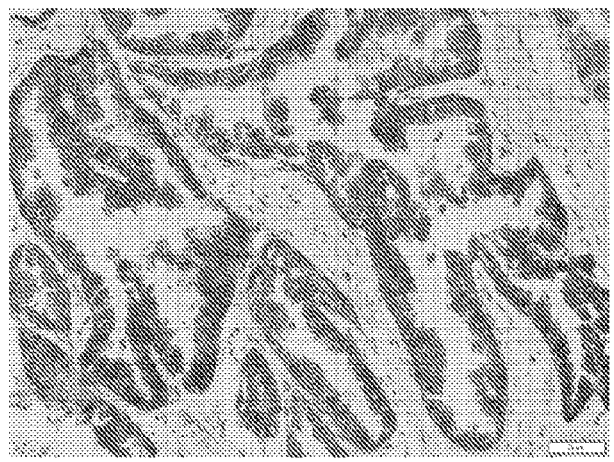
Figure 5:
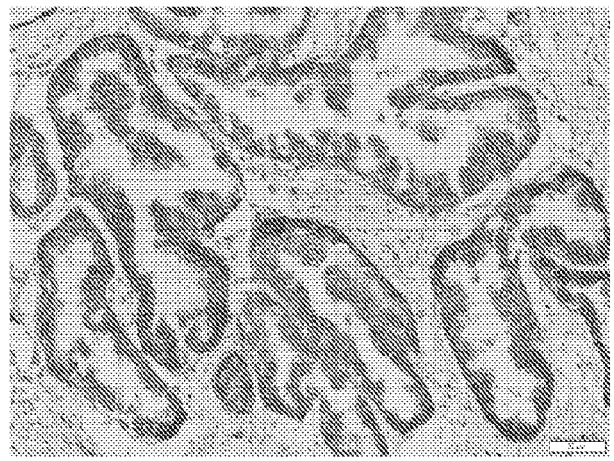
Figure 6:
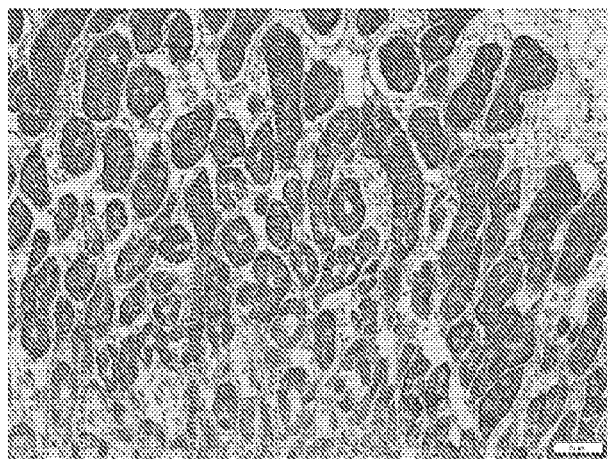
FIG. 6 is a set of IHC images showing formalin-fixed paraffin-embedded (FFPE) samples of human stomach tissue, having been prepared and blocked using standard protocols and then incubated with 5 µg/mL anti-hCD166 mouse monoclonal antibodies purified from hybridoma supernatants (Ab2 or Ab1) of the present disclosure or ABCAM® EPR2759(2)/ab109215.
Figure 6:
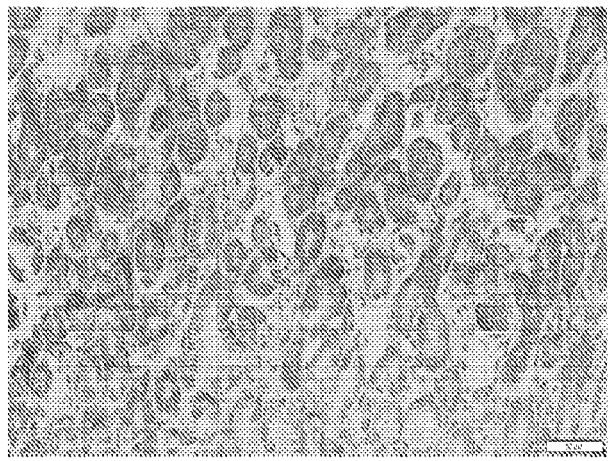
Figure 6:
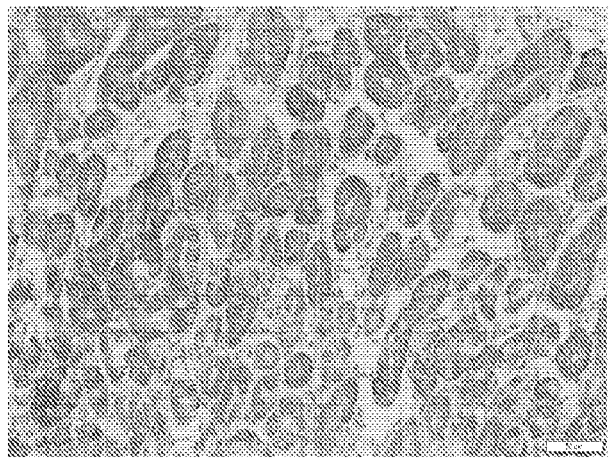
Figure 7:
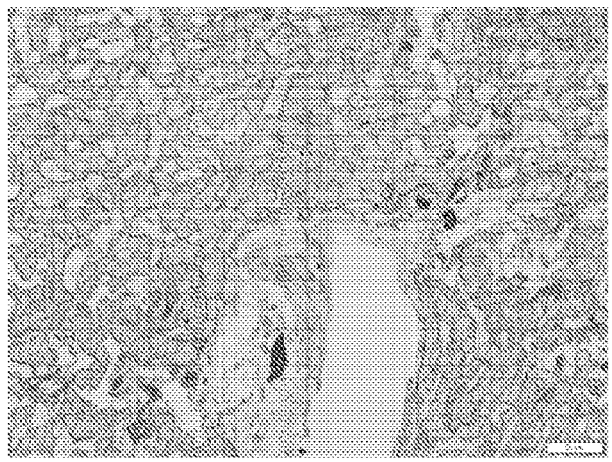
FIG. 7 is a set of IHC images showing formalin-fixed paraffin-embedded (FFPE) samples of human liver tissue, having been prepared and blocked using standard protocols and then incubated with 5 µg/mL anti-hCD166 mouse monoclonal antibodies purified from hybridoma supernatants (Ab2 or Ab1) of the present disclosure or ABCAM® EPR2759(2)/ab109215.
Figure 7:
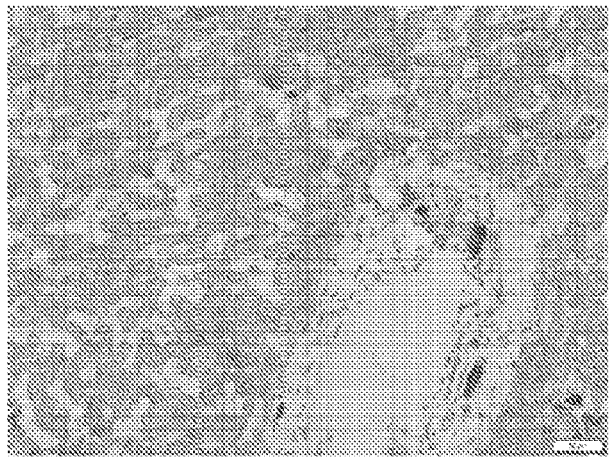
Figure 7:
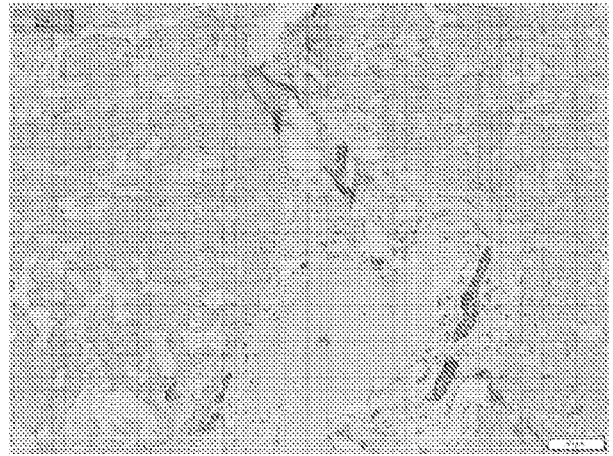
Figure 8:
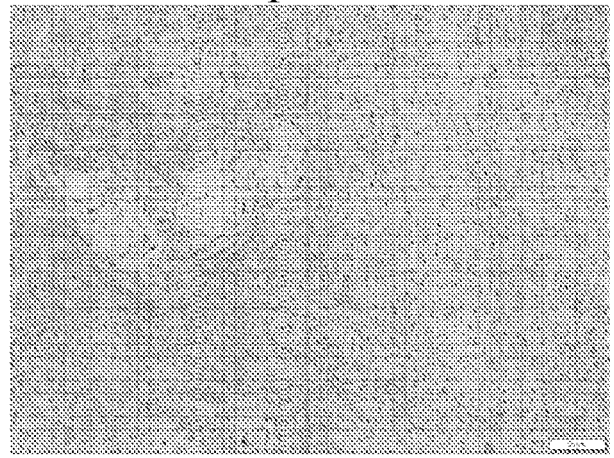
FIG. 8 is a set of IHC images showing formalin-fixed paraffin-embedded (FFPE) samples of human spleen tissue, having been prepared and blocked using standard protocols and then incubated with 5 µg/mL anti-hCD166 mouse monoclonal antibodies purified from hybridoma supernatants (Ab2 or Ab1) of the present disclosure or ABCAM® EPR2759(2)/ab109215.
Figure 8:
Figure 8:
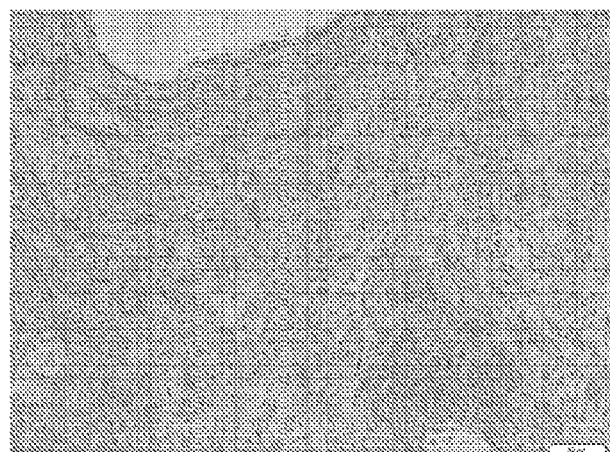
Figure 9:
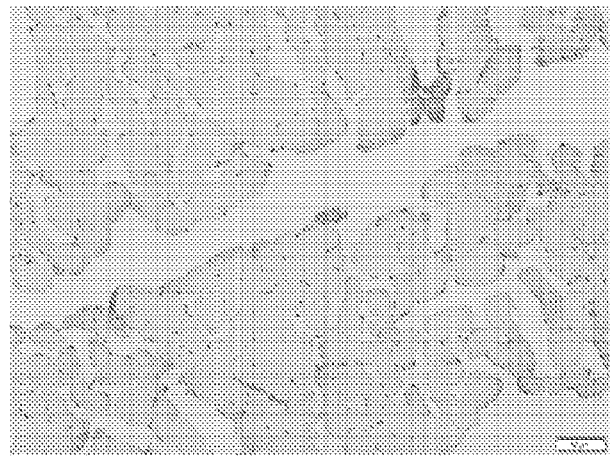
FIG. 9 is a set of IHC images showing formalin-fixed paraffin-embedded (FFPE) samples of human skeletal muscle tissue, having been prepared and blocked using standard protocols and then incubated with 5 µg/mL antihCD166 mouse monoclonal antibodies purified from hybridoma supernatants (Ab2 or Ab1) of the present disclosure or ABCAM® EPR2759(2)/ab109215.
Figure 9:
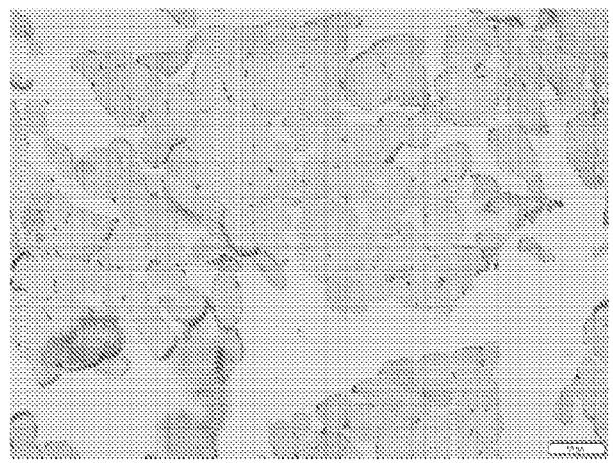
Figure 9:
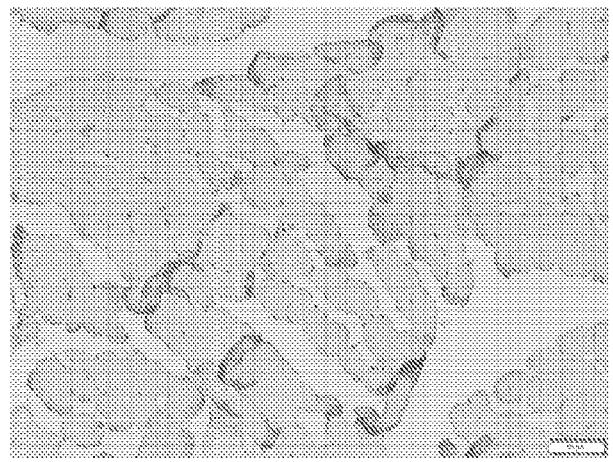
Figure 10:
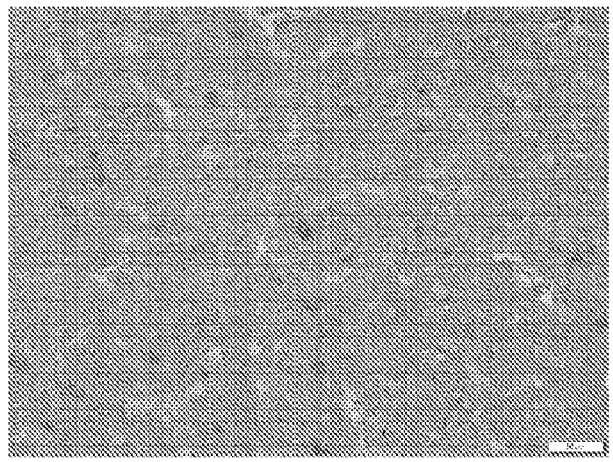
FIG. 10 is a set of IHC images showing formalin-fixed paraffin-embedded (FFPE) samples of human brain tissue, having been prepared and blocked using standard protocols and then incubated with 5 µg/mL anti-hCD166 mouse monoclonal antibodies purified from hybridoma supernatants (Ab2 or Ab1) of the present disclosure or ABCAM® EPR2759(2)/ab109215.
Figure 10:
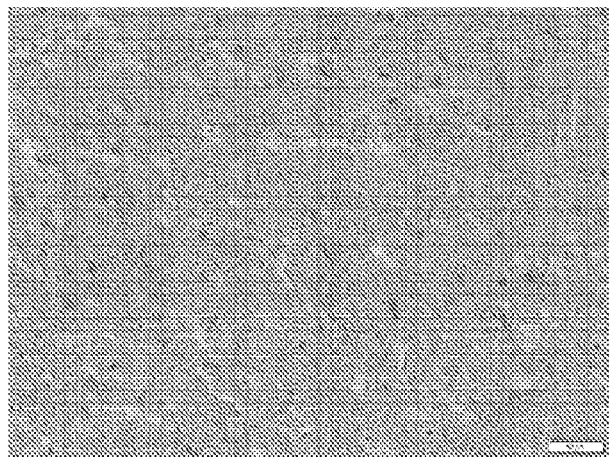
Figure 10:
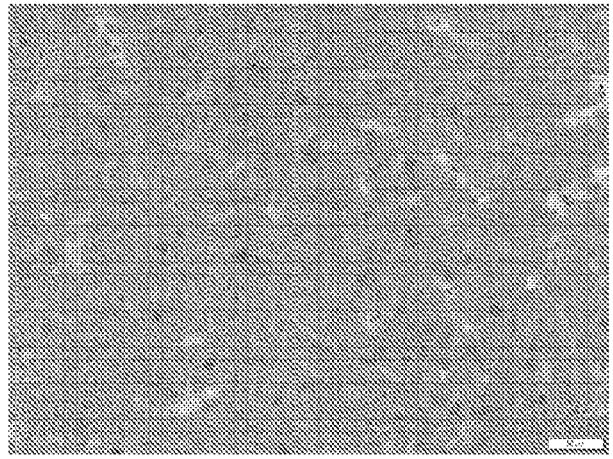

All of the hybridoma supernatents shown in FIGS. 1-3 demonstrated staining of the HCC1806 cell lines, which are known to express human CD166, at a signal intensity at least comparable to that of the ABCAM® EPR2759(2)/ab109215 rabbit monoclonal antibody. The hybridoma supernatents did not significantly stain BT-20, also in a manner comparable to lack of signal observed with the ABCAM® EPR2759(2)/ab109215 antibody.

Example 3: Binding of Anti-hCD166 Antibodies to Normal Human Tissues

This Example shows that anti-hCD166 mouse monoclonal antibodies of the present disclosure can detect human CD166 in a variety of normal human tissues using immunohistochemical (IHC) staining.

As shown in the exemplary IHC images of FIGS. 5-10, formalin-fixed paraffin-embedded human tissue samples (FFPE) were prepared and blocked using standard protocols, and then incubated with 5 μg/mL anti-hCD166 mouse monoclonal antibodies purified from hybridoma supernatants (clones Ab2 or Ab1) of the present disclosure or a commercially-available anti-hCD166 rabbit monoclonal antibody (ABCAM® EPR2759(2)/ab109215). Detection of anti-hCD166 mouse monoclonal antibodies of the present disclosure was performed by subsequent incubation with 5 μg/mL biotinylated-conjugated anti-mouse IgG antibody (biotin-SP-conjugated AffinityPure donkey anti-mouse IgG H+L chain, Jackson Immunoresearch), followed by addition of avidin-horseradish peroxidase (HRP) (Vectastain Elite ABC HRP Kit, Vector Laboratories) to form the avidin-biotin-HRP complex, followed by addition of a 3,3'-diaminobenzidine substrate (DAB Plus, Dako). Tissues were counterstained with hematoxylin (Fisher Scientific).

The purified anti-hCD166 mouse monoclonal antibodies (clones Ab2 or Ab1) of the present disclosure shown in FIGS. 5-10 demonstrated staining of the human tissues in a distribution that is similar to that of the ABCAM® EPR2759(2)/ab109215 anti-CD166 rabbit monoclonal antibody.

Example 4: Binding of Anti-hCD166 Antibodies to Normal Human Tissues

This Example shows that an anti-hCD166 mouse monoclonal antibody of the present disclosure can detect human CD166 in a normal human tissue using immunohistochemical (IHC) staining at a lower concentration than a commercially-available anti-hCD166 antibody.

Figure 11:
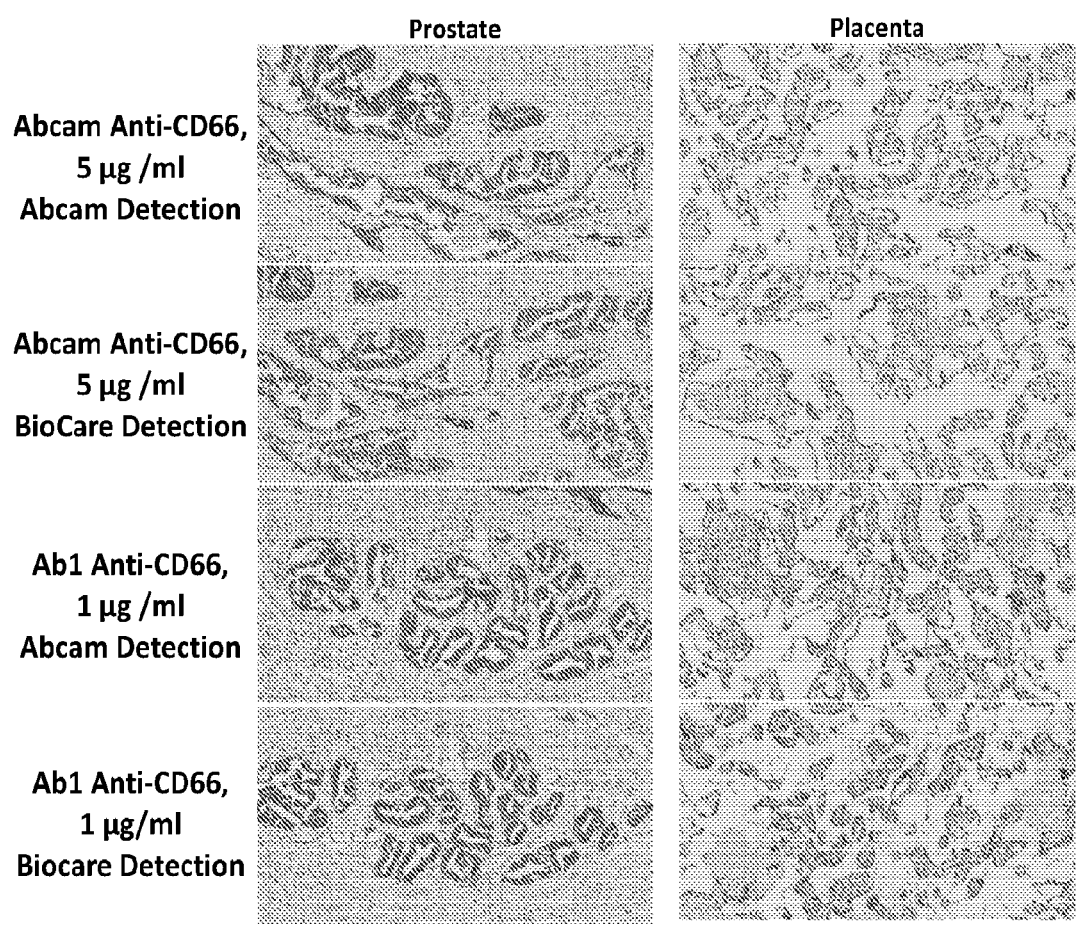
FIG. 11 is a set of IHC images showing formalin-fixed paraffin-embedded human tissue (hCD166 positive human prostate tissue or hCD166 negative human placenta tissue), having been prepared and blocked using standard protocols and then incubated with either 1 µg/mL purified recombinant Ab1 anti-hCD166 mouse monoclonal antibody of the present disclosure or 5 µg/mL commercially-available anti-hCD166 rabbit monoclonal antibody (ABCAM® EPR2759(2)/ab109215).

As shown in the exemplary IHC images of FIG. 11, formalin-fixed paraffin-embedded human prostate tissue (hCD166 positive) or placenta tissue (hCD166 negative) were prepared and blocked using standard protocols, and then incubated with either 1 μg/mL purified recombinant Ab1 anti-hCD166 mouse monoclonal antibody of the present disclosure or 5 μg/mL commercially-available anti-hCD166 rabbit monoclonal antibody (ABCAM® EPR2759(2)/ab109215). Detection of recombinant Ab1 anti-hCD166 mouse monoclonal antibody or ABCAM® antibody was performed by subsequent incubation with biotinylated-conjugated anti-mouse or anti-rabbit IgG antibody followed by addition of avidin-horseradish peroxidase (HRP) to form the avidin-biotin-HRP complex, followed by addition of a 3,3'-diaminobenzidine substrate, using either the EXPOSE Mouse and Rabbit Specific HRP/DAB IHC kit (ABCAM® Cat. No. ab80436) or the Intellipath FLX Universal HRP Detection Kit (Biocare Medical SKU IPK5011G80; "Biocare"). The tissues were counterstained with hematoxylin (Fisher Scientific).

FIG. 11 shows that human CD166 was readily detected with a lower (1 μg/mL) concentration of the recombinant Ab1 anti-hCD166 mouse monoclonal antibody of the present disclosure as compared to a higher (5 μg/mL) concentration of the ABCAM® EPR2759(2)/ab109215 anti-hCD166 rabbit antibody.

Example 5: Detection of Human CD166 in Cell Lysates by Anti-hCD166 Antibodies

This Example shows that anti-hCD166 mouse monoclonal antibodies of the present disclosure can detect human CD166 in lysates derived from human tumor cell lines.

Figure 12:
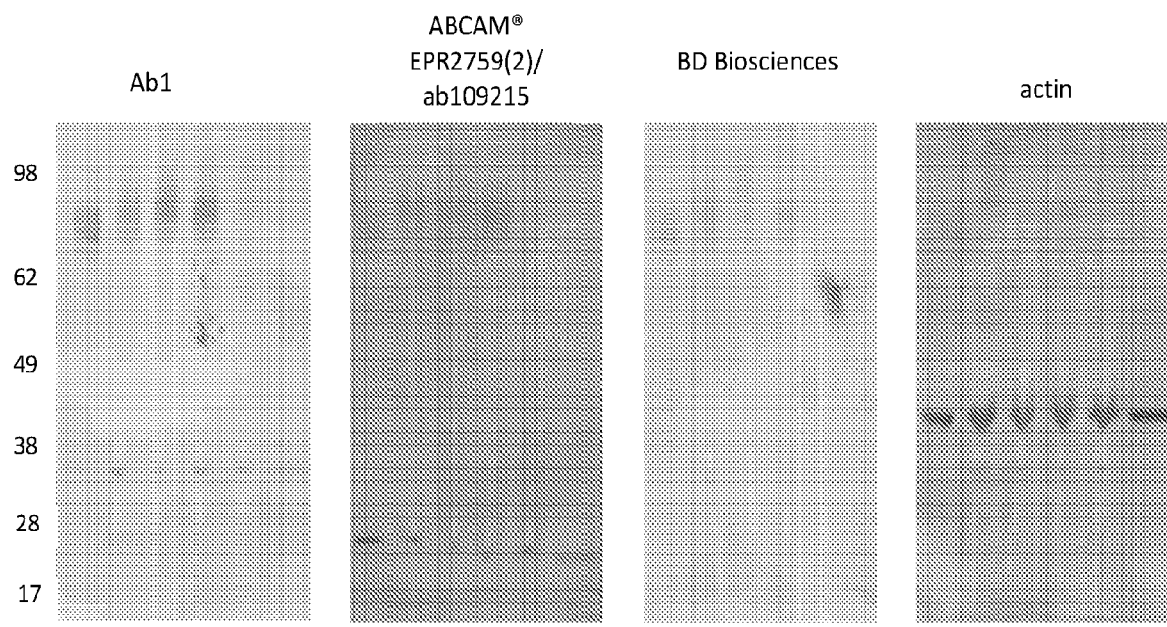
FIG. 12 is a set of Western blot images showing cell lysates isolated from the indicated human tumor cell lines, analyzed using either Ab1 anti-hCD166 mouse monoclonal antibody disclosed herein, ABCAM® EPR2759(2)/ab109215 anti-hCD166 rabbit monoclonal antibody, BD Biosciences 3A6 anti-hCD166 mouse monoclonal antibody (cat. No. 559263), or an anti-actin antibody control. Each Western blot image shows six lanes, respectively representing the following cell lines: H292, HCC1806, MDA-MB-231, BXPC3, HT29, and BT20.

As shown in the exemplary Western blot images of FIG. 12, cell lysates isolated from the indicated human tumor cell lines were analyzed using Western blot analysis using either the Ab1 anti-hCD166 mouse monoclonal antibody purified from hybridoma supernatants of the present disclosure, ABCAM® EPR2759(2)/ab109215 anti-hCD166 rabbit monoclonal antibody, BD Biosciences 3A6 anti-hCD166 mouse monoclonal antibody (cat. No. 559263), or an anti-actin antibody control.

FIG. 12 shows that human CD166 was readily detected in human cell lysates by the Ab1 anti-hCD166 monoclonal antibody of the present disclosure.

Example 6: CD166 Expression in Multiple Metastatic Cancer Samples

This Example shows that CD166 is expressed in a large number and variety of patient-derived metastatic tumors by immunohistochemical (IHC) staining using an anti-CD166 antibody.

Figure 13:
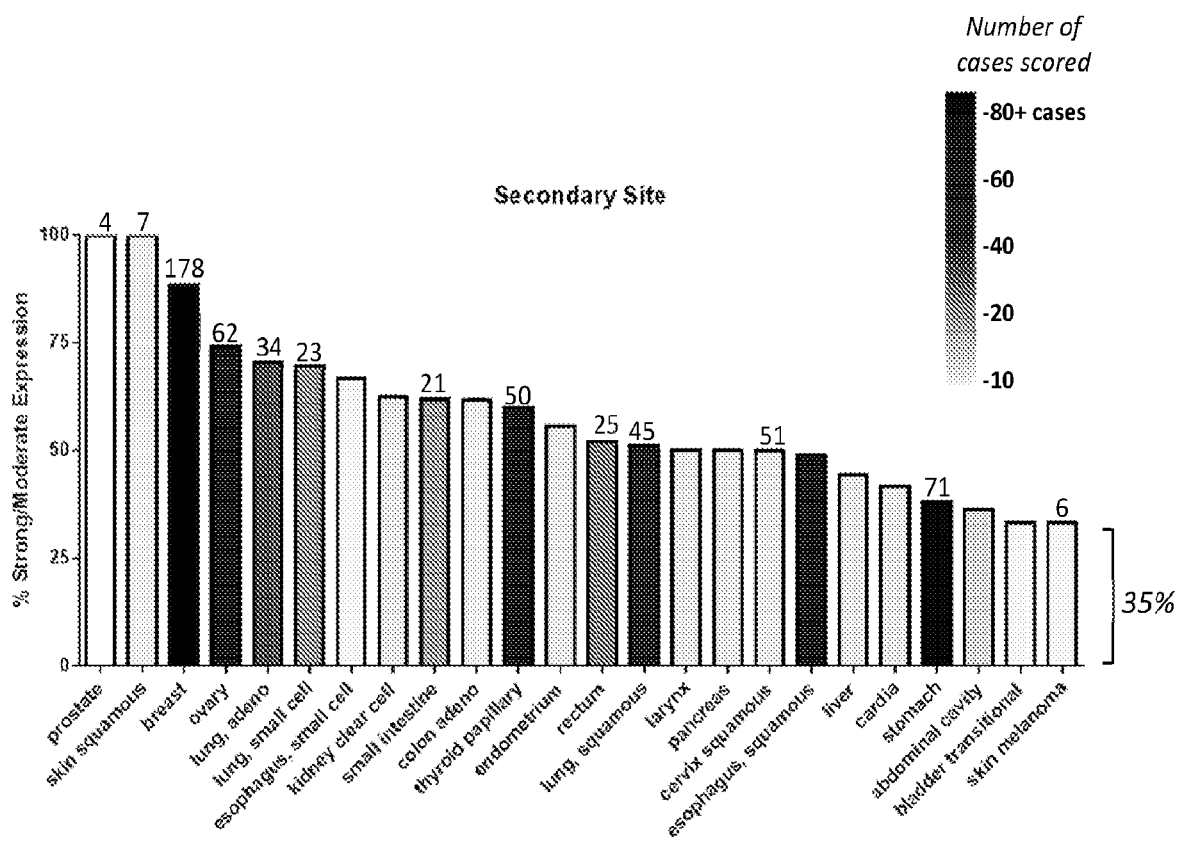
FIG. 13 is a graph showing results of IHC staining on multiple patient-derived tumor tissue microarrays (TMAs) with ABCAM® EPR2759(2)/ab109215.

FIG. 13 shows that human CD166 is moderately or highly expressed in a large number and variety of patient-derived metastatic tumor samples, using IHC staining with a commercially-purchased anti-CD166 antibody (ABCAM® EPR2759(2)/ab109215) on multiple patient-derived tumor tissue microarrays (TMA). FIG. 13 shows a summary of the level of IHC staining of CD166 of the TMAs shows that a large number of cores derived from multiple patient-derived metastatic samples showed a strong CD166 signal.

FIG. 13 shows that CD166 levels in a large number and variety of patient-derived metastatic tumor samples can be assayed using anti-hCD166 mouse monoclonal antibodies of the present disclosure.

SEQUENCES

It is to be understood than an "X" in a below amino acid sequence represents an amino acid position that can include any single amino acid. It is to be understood than an "X" in a below amino acid sequence represents, in certain embodiments, an amino acid position that can include an aspartic acid (D) residue or an asparagine (E) residue. It is to be understood than an "X" in a below nucleic acid sequence represents a nucleic acid position that can include any single nucleic acid.

SEQ ID NO: 1
Example anti-CD166 ICD antibody sequence 1:
Heavy Chain Amino Acid Sequence (IgG1)

EVQLQQSGAELVKPGASVKLSCTASGFNIKDYYMHWVKQRTEQGLEWIGKI
DPENGETKYAPKFQGKATITADTSSSTAYLQLSSLTSEDTAVYYCAREGFM
DYWGQGASVTVSSAKTTPPPSVYPLAPGSAAQTNSMVTLGCLVKGYFPEPVT
VTWNSGSLSSGVHTFPAVLQSDLYTLSSSVTVPSSTWPSQTVTCNVAHPAS
STKVDKKIVPRDCGCKPCICTVPEVSSVFIFPPKPKDVLTITLTPKVTCVV
VDISKDDPEVQFSWFVDDVEVHTAQTQPREEQFNSTFRSVSELPIMHQDWL
NGKEFKCRVNSAAFPAPIEKTISKTKGRPKAPQVYTIPPPKEQMAKDKVSL
TCMITDFFPEDITVEWQWNGQPAENYKNTQPIMDTDGSYFVYSKLNVQKSN
WEAGNTFTCSVLHEGLHNHHTEKSLSHSPGK

SEQ ID NO: 2
Example anti-CD166 ICD antibody sequence 1:
Heavy Chain Variable Domain Amino Acid Sequence EVQLQQSGAELVKPGASVKLSCTASGFNIKDYYMHWVKQRTEQGLEWIGKI
DPENGETKYAPKFQGKATITADTSSSTAYLQLSSLTSEDTAVYYCAREGFM
DYWGQGASVTVSS SEQ ID NO: 3
Example anti-CD166 ICD antibody sequence 1:
Heavy Chain CDR1 Amino Acid Sequence

DYYMH

SEQ ID NO: 4
Example anti-CD166 ICD antibody sequence 1:
Heavy Chain CDR2 Amino Acid Sequence

KIDPENGETKYAPKFQG

SEQ ID NO: 5
Example anti-CD166 ICD antibody sequence 1:
Heavy Chain CDR3 Amino Acid Sequence

EGFMDY

SEQ ID NO: 6
Example anti-CD166 ICD antibody sequence 1:
Heavy Chain DNA Sequence GAAGTCCAGCTCCAACAAAGTGGGGCAGAGCTCGTGAAACCTGGTGCGTCC
GTAAAGTTGTCCTGTACGGCATCTGGGTTTAACATCAAAGATTACTATATG
CATTGGGTGAAACAACGCACGGAGCAGGGGTTGGAATGGATTGGTAAAATT
GACCCCGAAAATGGTGAAACAAAATACGCCCCGAAGTTTCAAGGAAAAGCT
ACTATAACTGCTGACACTAGTAGCTCTACCGCCTATTTGCAGCTGTCAAGC
CTCACCTCAGAAGATACAGCGGTGTATTATTGCGCGAGGGAAGGATTCATG
GACTACTGGGGCCAGGGAGCCTCAGTCACAGTCAGCTCTGCGAAAACTACG
CCTCCCAGTGTATATCCTTTGGCCCCCGGCTCAGCTGCCCAGACTAATAGT
ATGGTGACTCTTGGCTGTTTGGTAAAAGGTTATTTTCCTGAACCTGTGACT
GTCACATGGAATTCTGGGTCCCTGTCCTCCGGAGTCCACACGTTTCCTGCT
GTATTGCAGAGTGACCTCTACACGCTTTCTAGCTCCGTTACAGTGCCTTCT
AGTACATGGCCCTCACAGACAGTAACGTGCAACGTCGCACATCCGGCAAGC
TCAACGAAGGTAGACAAAAAGATAGTTCCCAGGGATTGTGGTTGCAAGCCA
TGCATCTGTACAGTGCCCGAAGTATCTAGTGTGTTTATCTTTCCCCCAAAA
CCAAAGGACGTACTTACTATTACCCTTACCCCCAAGGTCACTTGTGTCGTA
GTAGATATATCTAAAGATGACCCGGAAGTACAATTCTCCTGGTTCGTGGAT
GACGTAGAAGTTCACACGGCTCAGACACAGCCACGCGAGGAGCAGTTCAAC
TCTACTTTTAGAAGCGTTAGTGAACTGCCAATTATGCATCAGGACTGGCTC
AACGGCAAAGAGTTTAAATGTAGGGTCAATAGTGCCGCTTTTCCGGCCCCC
ATCGAGAAGACTATCTCTAAAACGAAGGGCCGCCCAAAAGCACCTCAAGTA
TACACCATACCCCCGCCGAAGGAACAAATGGCCAAAGATAAGGTTTCATTG
ACATGTATGATAACCGATTTTTTCCCAGAAGATATAACTGTGGAGTGGCAA
TGGAATGGACAACCTGCTGAGAATTACAAAAATACCCAGCCGATCATGGAC
ACCGATGGAAGCTATTTCGTGTATAGCAAGCTCAACGTGCAAAAATCCAAC
TGGGAAGCTGGGAACACATTCACGTGTAGCGTGCTCCACGAAGGGCTTCAT
AATCATCACACTGAAAAGTCCCTCTCCCACAGTCCGGGCAAA SEQ ID NO: 7
Example anti-CD166 ICD antibody sequence 1:
Heavy Chain Variable Region DNA Sequence GAGGTTCAGCTGCAGCAGTCTGGGGCAGAGCTTGTGAAGCCAGGGGCCTCA
GTCAAGTTGTCCTGCACAGCTTCTGGCTTCAACATTAAAGACTACTATATG
CACTGGGTGAAGCAGAGGACTGAACAGGGCCTGGAGTGGATTGGAAAGATT
GATCCTGAGAATGGTGAAACTAAATATGCCCCGAAATTCCAGGGCAAGGCC
ACTATAACAGCAGACACATCCTCCAGCACAGCCTACCTGCAACTCAGCAGC -continued
CTGACATCTGAGGACACTGCCGTCTATTACTGTGCTAGAGAGGGTTTTATG

GACTACTGGGGTCAAGGAGCCTCAGTCACCGTCTCCTCA

SEQ ID NO: 8
Example anti-CD166 ICD antibody sequence 1:
Heavy Chain CDR1 DNA Sequence

GATTACTATATGCAT

SEQ ID NO: 9
Example anti-CD166 ICD antibody sequence 1:
Heavy Chain CDR2 DNA Sequence

AAAATTGACCCCGAAAATGGTGAAACAAAATACGCCCCGAAGTTTCAAGGA

SEQ ID NO: 10
Example anti-CD166 ICD antibody sequence 1:
Heavy Chain CDR3 DNA Sequence

GAAGGATTCATGGACTAC

SEQ ID NO: 69
Example anti-CD166 ICD antibody sequence 1:
Heavy Chain Variable Region DNA Sequence

GAAGTCCAGCTCCAACAAAGTGGGGCAGAGCTCGTGAAACCTGGTGCGTCC

GTAAAGTTGTCCTGTACGGCATCTGGGTTTAACATCAAAGATTACTATATG

CATTGGGTGAAACAACGCACGGAGCAGGGGTTGGAATGGATTGGTAAAATT

GACCCCGAAAATGGTGAAACAAAATACGCCCCGAAGTTTCAAGGAAAAGCT

ACTATAACTGCTGACACTAGTAGCTCTACCGCCTATTTGCAGCTGTCAAGC

CTCACCTCAGAAGATACAGCGGTGTATTATTGCGCGAGGGAAGGATTCATG

GACTACTGGGGCCAGGGAGCCTCAGTCACAGTCAGCTCT

SEQ ID NO: 11
Example anti-CD166 ICD antibody sequence 1:
Light Chain Amino Acid Sequence

DVVMTQTPLSLPVSLGDQASISCRSSQSLVHSNGNTYLHWYLQKPGQSPKL

LIYKVSNRFSGVPDRFSGSGSGTDFTLKISRVEAEDLGVYFCSQSTFVPLT

FGAGTKLELKRADAAPTVSIFPPSSEQLTSGGASVVCFLNNFYPKDINVKW

KIDGSERQNGVLNSWTDQDSKDSTYSMSSTLTLTKDEYERHNSYTCEATHK

TSTSPIVKSFNRNEC

SEQ ID NO: 12
Example anti-CD166 ICD antibody sequence 1:
Light Chain Variable Domain Amino Acid Sequence

DVVMTQTPLSLPVSLGDQASISCRSSQSLVHSNGNTYLHWYLQKPGQSPKL

LIYKVSNRFSGVPDRFSGSGSGTDFTLKISRVEAEDLGVYFCSQSTFVPLT

FGAGTKLELK

SEQ ID NO: 13
Example anti-CD166 ICD antibody sequence 1:
Light Chain CDR1 Amino Acid Sequence

RSSQSLVHSNGNTYLH

SEQ ID NO: 14
Example anti-CD166 ICD antibody sequence 1:
Light Chain CDR2 Amino Acid Sequence

KVSNRFS

SEQ ID NO: 15
Example anti-CD166 ICD antibody sequence 1:
Light Chain CDR3 Amino Acid Sequence

SQSTFVPLT

SEQ ID NO: 16
Example anti-CD166 ICD antibody sequence 1:
Light Chain DNA Sequence

GATGTAGTAATGACGCAGACGCCACTTTCCCTTCCAGTGTCTCTCGGAGAT

CAGGCTTCAATAAGTTGCCGGTCTAGTCAATCCCTCGTTCATTCCAACGGG

AATACCTATTTGCATTGGTATCTCCAGAAACCTGGGCAGTCCCGAAACTC

CTGATCTACAAAGTATCAAATCGATTTTCTGGAGTCCCTGATCGCTTCTCA

GGTTCCGGAAGCGGAACGGACTTTACGCTCAAGATAAGTCGCGTTGAGGCC

GAGGACCTGGGTGTTTATTTCTGTAGCCAATCCACGTTTGTACCACTCACA

TTCGGAGCAGGAACGAAGCTGGAACTGAAGAGGGCGGATGCGGCGCCGACA

GTTTCAATCTTTCCTCCAAGTTCCGAGCAGCTTACTAGCGGAGGGGCATCT

GTCGTGTGTTTTTTGAATAACTTTTACCCTAAGGATATCAATGTCAAGTGG

AAGATCGACGGGAGTGAACGGCAGAACGGCGTCCTCAACAGTTGGACAGAC

CAAGATAGTAAAGACTCAACCTATAGTATGAGTTCAACACTCACACTCACT

AAAGACGAGTACGAGAGGCACAATAGCTATACTTGTGAGGCTACACACAAA

ACAAGTACATCACCTATCGTGAAAAGCTTCAATCGGAACGAATGC

SEQ ID NO: 17
Example anti-CD166 ICD antibody sequence 1:
Light Chain Variable Region DNA Sequence

GATGTTGTGATGACCCAAACTCCACTCTCCCTGCCTGTCAGTCTTGGAGAT

CAAGCCTCCATCTCTTGCAGATCTAGTCAGAGCCTTGTACACAGTAATGGA

AACACCTATTTACATTGGTACCTGCAGAAGCCAGGCCAGTCTCCAAAGCTC

CTGATCTACAAAGTTTCCAACCGATTTTCTGGGGTCCCAGACAGGTTCAGT

GGCAGTGGATCAGGAACAGATTTCACACTCAAGATCAGCAGAGTGGAGGCT

GAGGATCTGGGAGTTTATTTCTGCTCTCAAAGTACATTTGTTCCGCTCACG

TTCGGTGCTGGGACCAAGCTGGAGCTGAAA

SEQ ID NO: 18
Example anti-CD166 ICD antibody sequence 1:
Light Chain CDR1 DNA Sequence

CGGTCTAGTCAATCCCTCGTTCATTCCAACGGGAATACCTATTTGCAT

SEQ ID NO: 19
Example anti-CD166 ICD antibody sequence 1:
Light Chain CDR2 DNA Sequence

AAAGTATCAAATCGATTTTCT

SEQ ID NO: 20
Example anti-CD166 ICD antibody sequence 1:
Light Chain CDR3 DNA Sequence

AGCCAATCCACGTTTGTACCACTCACA

SEQ ID NO: 70
Example anti-CD166 ICD antibody sequence 1:
Light Chain Variable Region DNA Sequence

GATGTAGTAATGACGCAGACGCCACTTTCCCTTCCAGTGTCTCTCGGAGAT

CAGGCTTCAATAAGTTGCCGGTCTAGTCAATCCCTCGTTCATTCCAACGGG

AATACCTATTTGCATTGGTATCTCCAGAAACCTGGGCAGTCCCCGAAACTC

CTGATCTACAAAGTATCAAATCGATTTTCTGGAGTCCCTGATCGCTTCTCA

GGTTCCGGAAGCGGAACGGACTTTACGCTCAAGATAAGTCGCGTTGAGGCC

GAGGACCTGGGTGTTTATTTCTGTAGCCAATCCACGTTTGTACCACTCACA

TTCGGAGCAGGAACGAAGCTGGAACTGAAG

SEQ ID NO: 21
Example anti-CD166 ICD antibody sequence 2:
Heavy Chain Amino Acid Sequence (IgG1)

EVQLQQSGAELVKPGASVKLSCTASGFNIKDYYMHWVRQRTEQGLEWIGKI

DPEDGETKYAPKFQGKATITADTSSNTAYLQLSSLTSEDTAVYYCAREGFM

DYWGQGTSVTVSSAKTTPPSVYPLAPGSAAQTNSMVTLGCLVKGYFPEPVT

VTWNSGSLSSGVHTFPAVLQSDLYTLSSSVTVPSSTWPSQTVTCNVAHPAS

STKVDKKIVPRDCGCKPCICTVPEVSSVFIFPPKPKDVLTITLTPKVTCVV

VDISKDDPEVQFSWFVDDVEVHTAQTQPREEQFNSTFRSVSELPIMHQDWL

NGKEFKCRVNSAAFPAPIEKTISKTKGRPKAPQVYTIPPPKEQMAKDKVSL

TCMITDFFPEDITVEWQWNGQPAENYKNTQPIMDTDGSYFVYSKLNVQKSN

WEAGNTFTCSVLHEGLHNHHTEKSLSHSPGK

SEQ ID NO: 22
Example anti-CD166 ICD antibody sequence 2:
Heavy Chain Variable Domain Amino Acid Sequence

EVQLQQSGAELVKPGASVKLSCTASGFNIKDYYMHWVRQRTEQGLEWIGKI

DPEDGETKYAPKFQGKATITADTSSNTAYLQLSSLTSEDTAVYYCAREGFM

DYWGQGTSVTVSS

SEQ ID NO: 23
Example anti-CD166 ICD antibody sequence 2:
Heavy Chain CDR1 Amino Acid Sequence

DYYMH

SEQ ID NO: 24
Example anti-CD166 ICD antibody sequence 2:
Heavy Chain CDR2 Amino Acid Sequence

KIDPEDGETKYAPKFQG

SEQ ID NO: 25
Example anti-CD166 ICD antibody sequence 2:
Heavy Chain CDR3 Amino Acid Sequence

EGFMDY

SEQ ID NO: 26
Example anti-CD166 ICD antibody sequence 2:
Heavy Chain DNA Sequence

GAAGTACAGCTCCAGCAGAGTGGAGCGGAACTGGTCAAACCTGGGGCTTC

CGTCAAGCTTTCATGCACCGCCTCCGGTTTCAATATAAAGGACTACTATA

TGCATTGGGTGCGGCAACGAACTGAGCAGGGGTTGGAGTGGATCGGCAAG

ATTGATCCAGAAGACGGTGAAACCAAATATGCCCCGAAATTTCAGGGTAA

GGCAACTATTACAGCGGATACAAGCTCAAATACAGCATATCTTCAGCTTT

CCAGTCTTACTAGCGAAGATACAGCGGTCTACTATTGTGCTCGGGAGGGG

TTCATGGACTACTGGGGCAGGGCACGTCTGTAACAGTTAGCTCAGCCAA

GACAACGCCACCTTCTGTTTATCCTTTGGCTCCTGGGTCCGCTGCTCAGA

CGAATAGCATGGTCACCCTGGGTTGCCTGGTCAAAGGCTACTTCCCTGAA

CCAGTGACTGTTACATGGAATTCAGGCTCTCTCTCATCTGGAGTCCACAC

CTTTCCTGCAGTCCTTCAGTCAGATCTTTACACATTGTCCTCCAGTGTAA

CGGTTCCTTCATCTACATGGCCCAGTCAGACTGTTACCTGTAATGTGGCA

CATCCAGCGAGTTCCACGAAAGTAGATAAAAAGATTGTGCCGAGGGACTG

TGGGTGTAAACCATGTATCTGCACAGTTCCAGAAGTGTCAAGCGTCTTCA

TCTTCCCACCCAAACCAAAAGATGTATTGACGATAACTCTTACACCTAAG

GTGACATGCGTGGTAGTCGACATTTCTAAAGACGACCCAGAGGTCCAATT

CAGTTGGTTTGTCGATGATGTAGAGGTACATACCGCTCAAACTCAGCCTA

GAGAGGAACAGTTCAACTCAACCTTCCGGTCAGTTTCTGAGTTGCCAATA

ATGCATCAAGATTGGCTCAACGGAAAAGAATTTAAGTGCCGAGTGAATTC

AGCAGCATTTCCAGCACCTATAGAGAAAACAATCAGCAAAACGAAGGGGC

GGCCGAAAGCACCACAGGTGTACACGATACCACCCCGAAGGAACAAATG

GCGAAGGATAAAGTGAGCCTCACGTGCATGATAACAGACTTTTTTCCTGA

AGATATAACAGTCGAATGGCAGTGGAATGGTCAACCAGCAGAAATTACA

AGAATACAGCCGATCATGGACACTGACGGATCCTACTTCGTGTATTCA

AAGCTCAATGTCCAGAAAAGCAACTGGGAGGCTGGGAACACTTTCACGTG

TAGCGTTTTGCACGAAGGGCTGCATAATCATCATACCGAAAAGTCACTCA

GCCACTCCCCCGGCAAG

SEQ ID NO: 27
Example anti-CD166 ICD antibody sequence 2:
Heavy Chain Variable Region DNA Sequence

GAGGTTCAGCTGCAGCAGTCTGGGGCAGAGCTTGTGAAGCCAGGGGCCTC

AGTCAAGTTGTCCTGCACAGCTTCTGGCTTCAACATTAAAGACTACTATA

TGCACTGGGTGAGGCAGAGGACTGAACAGGGCCTGGAGTGGATTGGAAAG

ATTGATCCTGAGGATGGTGAAACTAAATATGCCCCGAAATTCCAGGGCAA

GGCCACTATAACAGCAGACACATCCTCCAACACAGCCTACCTGCAACTCA

GCAGCCTGACATCTGAGGACACTGCCGTCTATTACTGTGCTAGAGAGGGT

TTTATGGACTACTGGGGTCAAGGAACCTCAGTCACCGTCTCCTCA

SEQ ID NO: 28
Example anti-CD166 ICD antibody sequence 2:
Heavy Chain CDR1 DNA Sequence

GACTACTATATGCAT

SEQ ID NO: 29
Example anti-CD166 ICD antibody sequence 2:
Heavy Chain CDR2 DNA Sequence

AAGATTGATCCAGAAGACGGTGAAACCAAATATGCCCCGAAATTTCAGG

GT

SEQ ID NO: 30
Example anti-CD166 ICD antibody sequence 2:
Heavy Chain CDR3 DNA Sequence

GAGGGGTTCATGGACTAC

SEQ ID NO: 71
Example anti-CD166 ICD antibody sequence 2:
Heavy Chain Variable Region DNA Sequence

GAAGTACAGCTCCAGCAGAGTGGAGCGGAACTGGTCAAACCTGGGGCTTC

CGTCAAGCTTTCATGCACCGCCTCCGGTTTCAATATAAAGGACTACTATA

TGCATTGGGTGCGGCAACGAACTGAGCAGGGGTTGGAGTGGATCGGCAAG

ATTGATCCAGAAGACGGTGAAACCAAATATGCCCCGAAATTTCAGGGTAA

GGCAACTATTACAGCGGATACAAGCTCAAATACAGCATATCTTCAGCTTT

CCAGTCTTACTAGCGAAGATACAGCGGTCTACTATTGTGCTCGGGAGGGG

TTCATGGACTACTGGGGGCAGGGCACGTCTGTAACAGTTAGCTCA

SEQ ID NO: 31
Example anti-CD166 ICD antibody sequence 2:
Light Chain Amino Acid Sequence

DNVMTQTPLSLSVSLGDQASISCRSSQSLVHSNGNTYLHWYLQKPGQSPK

LLIYKVSNRFSGVPDRFSGSGSGTDFTLKISRVEAEDLGVYFCSQSTHVP

LTFGAGTKLELKRADAAPTVSIFPPSSEQLTSGGASVVCFLNNFYPKDIN

VKWKIDGSERQNGVLNSWTDQDSKDSTYSMSSTLTLTKDEYERHNSYTCE

ATHKTSTSPIVKSFNRNEC

SEQ ID NO: 32
Example anti-CD166 ICD antibody sequence 2:
Light Chain Variable Domain Amino Acid Sequence

DNVMTQTPLSLSVSLGDQASISCRSSQSLVHSNGNTYLHWYLQKPGQSPK

LLIYKVSNRFSGVPDRFSGSGSGTDFTLKISRVEAEDLGVYFCSQSTHVP

LTFGAGTKLELK

SEQ ID NO: 33
Example anti-CD166 ICD antibody sequence 2:
Light Chain CDR1 Amino Acid Sequence

RSSQSLVHSNGNTYLH

SEQ ID NO: 34
Example anti-CD166 ICD antibody sequence 2:
Light Chain CDR2 Amino Acid Sequence

KVSNRFS

SEQ ID NO: 35
Example anti-CD166 ICD antibody sequence 2:
Light Chain CDR3 Amino Acid Sequence

SQSTHVPLT

SEQ ID NO: 36
Example anti-CD166 ICD antibody sequence 2:
Light Chain DNA Sequence

GATAACGTAATGACACAGACACCACTCTCTTTGTCCGTCTCCCTGGGCGA

CCAGGCGAGTATCTCCTGTCGGAGTTCTCAGTCTCTTGTCCATAGTAATG

GGAATACCTATCTGCACTGGTATTTGCAGAAGCCAGGACAATCCCCTAAG

CTTTTGATCTATAAAGTCTCAAACAGGTTTAGTGGTGTACCGGATCGCTT

TAGTGGGAGTGGAAGCGGGACTGACTTTACGCTCAAAATTAGCCGAGTCG

AAGCAGAGGATCTTGGGGTGTACTTCTGTTCTCAGAGTACGCATGTTCCG

TTGACTTTTGGAGCGGGTACGAAACTCGAGTTGAAGCGGGCGGATGCCGC

ACCCACAGTCAGCATCTTCCCTCCTAGTTCCGAGCAGCTGACGTCCGGTG

GTGCGTCCGTCGTATGTTTTCTCAATAACTTCTATCCTAAAGATATAAAC

GTCAAATGGAAGATAGATGGGAGCGAACGACAGAATGGGGTGCTCAACTC

TTGGACCGATCAAGATTCCAAAGACTCCACTTATAGTATGAGCTCTACAT

TGACGCTGACCAAGGACGAGTATGAGCGACACAACTCTTACACCTGCGAG

GCGACCCATAAGACTTCAACTTCTCCCATCGTGAAAAGCTTTAATCGAAA

CGAATGC

SEQ ID NO: 37
Example anti-CD166 ICD antibody sequence 2:
Light Chain Variable Region DNA Sequence

GATAATGTGATGACCCAAACTCCACTCTCCCTGTCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTATAAAGTTTCCAACCGATTTTCTGGGGTCCCAGACAGGTT

```
CAGTGGCAGTGGATCAGGGACAGATTTCACACTCAAGATCAGCAGAGTGG

AGGCTGAGGATCTGGGAGTTTATTTCTGCTCTCAAAGCACACATGTTCCG

CTCACGTTCGGTGCTGGGACCAAGCTGGAGCTGAAA
```

SEQ ID NO: 38
Example anti-CD166 ICD antibody sequence 2:
Light Chain CDR1 DNA Sequence

```
CGGAGTTCTCAGTCTCTTGTCCATAGTAATGGGAATACCTATCTGCAC
```

SEQ ID NO: 39
Example anti-CD166 CD antibody sequence 2:
Light Chain CDR2 DNA Sequence

```
AAAGTCTCAAACAGGTTTAGT
```

SEQ ID NO: 40
Example anti-CD166 ICD antibody sequence 2:
Light Chain CDR3 DNA Sequence

```
TCTCAGAGTACGCATGTTCCGTTGACT
```

SEQ ID NO: 72
Example anti-CD166 ICD antibody sequence 2:
Light Chain Variable Region DNA Sequence

```
GATAACGTAATGACACAGACACCACTCTCTTTGTCCGTCTCCCTGGGCGA

CCAGGCGAGTATCTCCTGTCGGAGTTCTCAGTCTCTTGTCCATAGTAATG

GGAATACCTATCTGCACTGGTATTTGCAGAAGCCAGGACAATCCCCTAAG

CTTTTGATCTATAAAGTCTCAAACAGGTTTAGTGGTGTACCGGATCGCTT

TAGTGGGAGTGGAAGCGGGACTGACTTTACGCTCAAAATTAGCCGAGTCG

AAGCAGAGGATCTTGGGGTGTACTTCTGTTCTCAGAGTACGCATGTTCCG

TTGACTTTTGGAGCGGGTACGAAACTCGAGTTGAAG
```

SEQ ID NO: 41
Example anti-CD166 ICD antibodies 1, 2:
Heavy Chain Variable Domain Consensus Amino Acid Sequence

```
EVQLQQSGAELVKPGASVKLSCTASGFNIKDYYMHWVXQRTEQGLEWIGK

IDPEXGETKYAPKFQGKATITADTSSXTAYLQLSSLTSEDTAVYYCAREG

FMDYWGQGXSVTVSS
```

SEQ ID NO: 42
Example anti-CD166 ICD antibodies 1, 2:
Light Chain Variable Domain Consensus Amino Acid Sequence

```
DXVMTQTPLSLXVSLGDQASISCRSSQSLVHSNGNTYLHWYLQKPGQSPK

LLIYKVSNRFSGVPDRFSGSGSGTDFTLKISRVEAEDLGVYFCSQSTXVP

LTFGAGTKLELK
```

SEQ ID NO: 43
Example anti-CD166 ICD antibodies 1, 2:
HCDR2 Consensus 1

```
KIDPEXGETKYAPKFQG
```

SEQ ID NO: 44
Example anti-CD166 ICD antibodies 1, 2:
HCDR2 Consensus 2

```
KIDPE(Asx)GETKYAPKFQG
```

SEQ ID NO: 45
Example anti-CD166 ICD antibodies 1, 2:
LCDR3 Consensus

```
SQSTXVPLT
```

SEQ ID NO: 67
Example anti-CD166 ICD antibodies 1, 2:
Heavy Chain Consensus

```
EVQLQQSGAELVKPGASVKLSCTASGFNIKDYYMHWVXQRTEQGLEWIGK

IDPEXGETKYAPKFQGKATITADTSSXTAYLQLSSLTSEDTAVYYCAREG

FMDYWGQGXSVTVSSAKTTPPSVYPLAPGSAAQTNSMVTLGCLVKGYFPE

PVTVTWNSGSLSSGVHTFPAVLQSDLYTLSSSVTVPSSTWPSQTVTCNVA

HPASSTKVDKKIVPRDCGCKPCICTVPEVSSVFIFPPKPKDVLTITLTPK

VTCVVVDISKDDPEVQFSWFVDDVEVHTAQTQPREEQFNSTFRSVSELPI

MHQDWLNGKEFKCRVNSAAFPAPIEKTISKTKGRPKAPQVYTIPPPKEQM

AKDKVSLTCMITDFFPEDITVEWQWNGQPAENYKNTQPIMDTDGSYFVYS

KLNVQKSNWEAGNTFTCSVLHEGLHNHHTEKSLSHSPGK
```

SEQ ID NO: 68
Example anti-CD166 ICD antibodies 1, 2:
Light Chain Consensus

```
DXVMTQTPLSLXVSLGDQASISCRSSQSLVHSNGNTYLHWYLQKPGQSPK

LLIYKVSNRFSGVPDRFSGSGSGTDFTLKISRVEAEDLGVYFCSQSTXVP

LTFGAGTKLELKRADAAPTVSIFPPSSEQLTSGGASVVCFLNNFYPKDIN

VKWKIDGSERQNGVLNSWTDQDSKDSTYSMSSTLTLTKDEYERHNSYTCE

ATHKTSTSPIVKSFNRNEC
```

SEQ ID NO: 46
Example therapeutic anti-CD166 ICD sequence:
Heavy Chain Amino Acid Sequence (IgG1)

```
QITLKESGPTLVKPTQTLTLTCTFSGFSLSTYGMGVGWIRQPPGKALEWL

ANIWWSEDKHYSPSLKSRLTITKDTSKNQVVLTITNVDPVDTATYYCVQI

DYGNDYAFTYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLEPPK

PKDTLMISRTPEVTCVVVDVSHEDPEVKFNWYVDGVEVHNAKTKPREEQY
```

-continued
NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 47
Example therapeutic anti-CD166 sequence:
Heavy Chain Variable Domain Amino Acid Sequence (1)

QITLKESGPTLVKPTQTLTLTCTFSGFSLSTYGMGVGWIRQPPGKALEWL

ANIWWSEDKHYSPSLKSRLTITKDTSKNQVVLTMTNMDPVDTATYYCVQI

DYGNDYAFTYWGQGTLVTVSS

SEQ ID NO: 48
Example therapeutic anti-CD166 sequence:
Heavy Chain Variable Domain Amino Acid Sequence (2)

QITLKESGPTLVKPTQTLTLTCTFSGFSLSTYGMGVGWIRQPPGKALEWL

ANIWWSEDKHYSPSLKSRLTITKDTSKNQVVLTITNVDPVDTATYYCVQI

DYGNDYAFTYWGQGTLVTVSS

SEQ ID NO: 49
Example therapeutic anti-CD166 sequence:
Heavy Chain CDR1 Amino Acid Sequence

GFSLSTYGMGVG

SEQ ID NO: 50
Example therapeutic anti-CD166 sequence:
Heavy Chain CDR2 Amino Acid Sequence

NIWWSEDKH

SEQ ID NO: 51
Example therapeutic anti-CD166 sequence:
Heavy Chain CDR3 Amino Acid Sequence

IDYGNDY AFTY

SEQ ID NO: 52
Example therapeutic anti-CD166 sequence:
Light Chain Amino Acid Sequence

DIVMTQSPLSLPVTPGEPASISCRSSKSLLHSNGITYLYWYLQKPGQSPQ

LLIYQMSNLASGVPDRFSGSGSGTDFTLKISRVEAEDVGVYYCAQNLELP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

SEQ ID NO: 53
Example therapeutic anti-CD166 sequence:
Light Chain Variable Domain Amino Acid Sequence (123)

DIVMTQSPLSLPVTPGEPASISCRSSKSLLHSNGITYLYWYLQKPGQSPQ

LLIYQMSNLASGVPDRFSGSGSGTDFTLKISRVEAEDVGVYYCAQNLELP

YTFGQGTKLEIK

SEQ ID NO: 54
Example therapeutic anti-CD166 sequence:
Light Chain Variable Domain Amino Acid Sequence (124)

DIVMTQSPLSLPVTPGEPASISCRSSKSLLHSNGITYLYWYLQKPGQSPQ

LLIYQMSNLASGVPDRFSSSGSGTDFTLKISRVEAEDVGVYYCAQNLELP

YTFGQGTKLEIK

SEQ ID NO: 55
Example therapeutic anti-CD166 sequence:
Light Chain Variable Domain Amino Acid Sequence (125)

DIVMTQSPLSLPVTPGEPASISCRSSQSLLHSNGITYLYWYLQKPGQSP

QLLIYQMSNRASGVPDRFSGSGSGTDFTLKISRVEAEDVGVYYCAQNLE

LPYTFGQGTKLEIK

SEQ ID NO: 56
Example therapeutic anti-CD166 sequence:
Light Chain Variable Domain Amino Acid Sequence (126)

DIVMTQSPLSLPVTPGEPASISCRSSQSLLHSNGITYLYWYLQKPGQSP

QLLIYQMSNRASGVPDRFSSSGSGTDFTLKISRVEAEDVGVYYCAQNLE

LPYTFGQGTKLEIK

SEQ ID NO: 57
Example therapeutic anti-CD166 sequence:
Light Chain CDR1 Amino Acid Sequence (1)

RSSKSLLHSNGITYLY

SEQ ID NO: 58
Example therapeutic anti-CD 166 sequence:
Light Chain CDR1 Amino Acid Sequence (2)

RSSQSLLHSNGITYLY

SEQ ID NO: 59
Example therapeutic anti-CD166 sequence:
Light Chain CDR2 Amino Acid Sequence (1)

QMSNLAS

SEQ ID NO: 60
Example therapeutic anti-CD166 sequence:
Light Chain CDR2 Amino Acid Sequence (2)

QMSNRAS

SEQ ID NO: 61
Example therapeutic anti-CD166 sequence:
Light Chain CDR3 Amino Acid Sequence

AQNLELPYT

SEQ ID NO: 62
CD166 Intracellular Domain:

YMKKSKTASKHVNKDLGNMEENKKLEENNHKTEA

SEQ ID NO: 63
CD166 ICD Peptide/Epitope 1:

CYMKKSKTASKHVNKDLGNME

SEQ ID NO: 64
CD166 ICD Peptide/Epitope 2:

YMKKSKTASKHVNKDLGNME

SEQ ID NO: 65
CD166 ICD Peptide/Epitope 3:

CLGNMEENKKLEENNHKTEA

SEQ ID NO: 66
CD166 ICD Peptide/Epitope 4:

LGNMEENKKLEENNHKTEA

OTHER EMBODIMENTS

While we have described a number of embodiments of this invention, it is apparent that our basic disclosure and examples may be altered to provide other embodiments that utilize the compounds and methods of this invention. Therefore, it will be appreciated that the scope of this invention is to be defined by the appended claims rather than by the specific embodiments that have been represented by way of example.

All references cited herein are hereby incorporated by reference.

---

What is claimed is:

1. An antibody or antigen-binding polypeptide thereof comprising a heavy chain variable domain and a light chain variable domain, wherein:
   (i) the heavy chain variable domain comprises:
   a heavy chain complementarity-determining region 1 (HCDR1) comprising an amino acid sequence that is identical to SEQ ID NO: 3,
   a heavy chain complementarity-determining region 2 (HCDR2) comprising an amino acid sequence that is identical to SEQ ID NO: 4, and
   a heavy chain complementarity-determining region 3 (HCDR3) comprising an amino acid sequence that is identical to SEQ ID NO: 5; and
   (ii) the light chain variable domain comprises:
   a light chain complementarity-determining region 1 (LCDR1) comprising an amino acid sequence that is identical to SEQ ID NO: 13,
   a light chain complementarity-determining region 2 (LCDR2) comprising an amino acid sequence that is identical to SEQ ID NO: 14, and
   a light chain complementarity-determining region 3 (LCDR3) comprising an amino acid sequence that is identical to SEQ ID NO: 15.

2. The antibody or antigen-binding polypeptide thereof of claim 1, wherein the heavy chain variable domain comprises an amino acid sequence having at least 90% identity to the amino acid sequence of SEQ ID NO: 2.

3. The antibody or antigen-binding polypeptide thereof of claim 2, wherein the light chain variable domain comprises an amino acid sequence having at least 90% identity to the amino acid sequence of SEQ ID NO: 12.

4. The antibody or antigen-binding polypeptide thereof of claim 2, wherein the antibody or antigen-binding polypeptide thereof specifically binds to an epitope within a C-terminal intracellular domain of CD166.

5. The antibody or antigen-binding polypeptide thereof of claim 4, wherein the CD166 is mammalian CD166, primate CD166, human CD166, or the antibody or antigen-binding polypeptide thereof specifically binds to an epitope within SEQ ID NO: 62, SEQ ID NO: 64, or SEQ ID NO: 66.

6. The antibody or antigen-binding peptide thereof of claim 1, wherein the heavy chain variable domain comprises an amino acid sequence of SEQ ID NO: 2.

7. The antibody or antigen-binding polypeptide thereof of claim 1, wherein the light chain variable domain comprises an amino acid sequence having at least 90% identity to the amino acid sequence of SEQ ID NO: 12.

8. The antibody or antigen-binding polypeptide thereof of claim 1, wherein the antibody or antigen-binding polypeptide thereof specifically binds to an epitope within a C-terminal intracellular domain of CD166.

9. The antibody or antigen-binding polypeptide thereof of claim 8, wherein the CD166 is mammalian CD166, primate CD166, human CD166, or the antibody or antigen-binding polypeptide thereof specifically binds to an epitope within SEQ ID NO: 62, SEQ ID NO: 64, or SEQ ID NO: 66.

10. The antibody or antigen-binding polypeptide thereof of claim 1, wherein the antibody or antigen-binding polypeptide thereof is conjugated to a label, and wherein the label is or comprises biotin, an enzymatic reporter, a fluorescent label, a chemiluminescent label, an in vivo imaging agent, or a radioactive label.

11. The antibody or antigen-binding polypeptide thereof of claim 10, wherein the label is or comprises an enzymatic reporter selected from peroxidase, alkaline phosphatase (AP), glucose oxidase, or 13-galactosidase.

12. The antibody or antigen-binding polypeptide thereof of claim 10, wherein the label is or comprises a radioactive label that comprises zirconium-89 (89Zr), iodine-124 (124I), iodine-131 (131I) iodine-125 (125I), bismuth-212 (212Bi), bismuth-213 (213Bi), astatine-221 (221At), copper-67 (67Cu), copper-64 (64Cu), rhenium-186 (186Re), rhenium-188 (188Re), phosphorus-32 (32P), samarium-153 (153Sm), lutetium-177 (177Lu), technetium-99m (99mTc), gallium-67 (67Ga), indium-111 (111In), or thallium-201 (201Tl).

13. The antibody or antigen-binding polypeptide thereof of claim 1, wherein the antibody or antigen-binding polypeptide thereof is conjugated to a drug.

14. The antibody or antigen-binding polypeptide thereof of claim 13, wherein the drug is a cytotoxic agent, chemotherapeutic agent, toxin, radionuclide.

15. A host cell comprising a nucleic acid sequence encoding the heavy chain variable domain and the light chain variable domain of the antibody or antigen-binding polypeptide thereof of claim 1.

16. A method of producing an antibody or antigen-binding polypeptide thereof comprising culturing the host cell of claim 15 under conditions that allow the host cell to express the antibody or antigen-binding polypeptide thereof.

17. The method of claim 16, further comprising isolating the antibody or antigen-binding polypeptide thereof.

18. A kit comprising the antibody or antigen-binding polypeptide thereof of claim 1, further comprising a secondary antibody characterized by an ability to bind to the antibody or antigen-binding polypeptide thereof, and at least one buffer.

19. The kit of claim 18, wherein the secondary antibody is conjugated to an agent.

20. The kit of claim 19, wherein the agent is a detectable moiety.

21. The kit of claim 20, wherein the detectable moiety is or comprises biotin, an enzymatic reporter, a fluorescent label, a chemiluminescent label, an in vivo imaging agent, or a radioactive label.

22. The kit of claim 20, wherein the detectable moiety is or comprises an enzymatic reporter selected from peroxidase, alkaline phosphatase (AP), glucose oxidase, or 13-galactosidase.

23. The kit of claim 20, wherein the detectable moiety is or comprises a radioactive label that comprises zirconium-89 (89Zr), iodine-124 (124I), iodine-131 (131I) iodine-125 (125I), bismuth-212 (212Bi), bismuth-213 (213Bi), astatine-221 (221At), copper-67 (67Cu), copper-64 (64Cu), rhenium-186 (186Re), rhenium-188 (188Re), phosphorus-32 (32P), samarium-153 (153Sm), lutetium-177 (177Lu), technetium-99m (99mTc), gallium-67 (67Ga), indium-111 (111In), or thallium-201 (201Tl).

24. The kit of claim 18, wherein the antibody or antigen-binding polypeptide thereof is conjugated to a drug.

25. The kit of claim 24, wherein the drug is a cytotoxic agent, chemotherapeutic agent, toxin, radionuclide.

26. The kit of claim 18, further comprising a therapeutic antibody or therapeutic antigen binding polypeptide thereof.

27. A method of detecting CD166 in a sample comprising: contacting the sample with the antibody or antigen-binding polypeptide thereof of claim 1, and detecting the presence or absence of antibody or antigen-binding polypeptide thereof binding with a portion of the sample, thereby detecting the presence or absence of CD166, wherein the CD166 is a primate CD166.

28. The method of claim 27, wherein the sample comprises cancer cells.

29. The method of claim 28, wherein the cancer cells are solid tumor cells.

30. The method of claim 28, wherein the cancer cells comprise non-small cell lung cancer cells, breast cancer cells, ovarian cancer cells, endometrial cancer cells, cholangiocarcinoma cells, head and neck cancer cells, or castration-resistant prostate cancer cells.

31. The method of claim 28, wherein the cancer cells comprise H292 cells, HCC1806 cells, MDA-MB-231 cells, BXPC3 cells, HT29 cells, or BT20 cells.

32. The method of claim 27, wherein the sample is embedded in a medium.

33. The method of claim 27, wherein the sample is fixed.

34. The method of claim 27, wherein the sample is a formalin- fixed paraffin-embedded sample.

35. A method of detecting an CD166-expressing cell in a tissue sample comprising:
contacting the tissue sample with the antibody or antigen-binding polypeptide thereof of claim 1, and
detecting the presence or absence of antibody or antigen-binding polypeptide thereof binding with at least one cell in the tissue sample, thereby detecting the presence or absence of a CD166 expressing cell in the tissue sample, wherein the CD166 is a mammalian CD166.

36. The method of claim 35, wherein the mammalian CD166 is a primate CD166.

37. The method of claim 35, wherein the sample comprises cancer cells.

38. A method of detecting an activated lymphocyte or activated monocyte (leukocyte) in a tissue sample comprising:
contacting the tissue sample with the antibody or antigen-binding polypeptide thereof of claim 1, and
detecting the presence or absence of antibody or antigen-binding polypeptide thereof binding with at least one cell in the sample, thereby detecting the presence or absence of the activated lymphocyte or the activated monocyte (leukocyte) in the tissue sample,
wherein the antibody or antigen-binding polypeptide thereof is an anti-mammalian CD166 antibody or antigen-binding polypeptide.

39. A method of treating a disease or disorder comprising:
administering a therapeutic anti-CD166 antibody or therapeutic antigen-binding polypeptide thereof to a subject suffering from cancer mediated through a CD166 pathway, wherein prior to administration, the presence of CD166 was detected in a sample from the subject by performing the steps of:
contacting the sample with an antibody or antigen-binding polypeptide thereof of claim 1, and
detecting the presence or absence of antibody or antigen-binding polypeptide thereof binding with a portion of the sample, thereby detecting the presence or absence of CD166.

40. The method of claim 39, wherein the therapeutic anti-CD166 antibody or therapeutic antigen-binding polypeptide thereof comprises:
(i) a heavy chain variable domain comprising:
(a) a heavy chain HCDR1 that is identical to SEQ ID NO: 49;
(b) a heavy chain HCDR2 that is identical to SEQ ID NO: 50; and
(c) a heavy chain HCDR3 that is identical to SEQ ID NO: 51; and
(ii) a light chain variable domain comprising:
(a) a light chain LCDR1 that is identical to SEQ ID NO: 57 or SEQ ID NO: 58;
(b) a light chain LCDR2 that is identical to SEQ ID NO: 59 or SEQ ID NO: 60; and
(c) a light chain LCDR3 that is identical to SEQ ID NO: 61.

41. The method of claim 40, wherein the cancer comprises solid tumor cells.

42. The method of claim 40, wherein the cancer comprises non-small cell lung cancer cells, breast cancer cells, ovarian cancer cells, endometrial cancer cells, cholangiocarcinoma cells, head and neck cancer cells, or castration-resistant prostate cancer cells.

43. A method of aiding in the selection of a therapy for a subject at risk of or suffering from a disease or disorder mediated through a CD166 pathway comprising:
contacting a sample from the subject with the antibody or antigen-binding polypeptide thereof of claim 1,
detecting the presence or absence of antibody or antigen-binding polypeptide thereof binding with a portion of the sample, thereby detecting the presence or absence of CD166, and
recording the presence or absence of CD166 in the sample,
wherein detecting the presence of antibody or antigen-binding polypeptide thereof binding with a portion of the sample comprises performing immunohistochemistry, electropherography, Western blot analysis, immunoprecipitation analysis, and/or microscopy.

44. The antibody or antigen-binding polypeptide thereof of claim 1, wherein the antibody or antigen-binding polypeptide thereof comprises a heavy chain variable domain that comprises the amino acid sequence of SEQ ID NO: 2 and a light chain variable domain that comprises the amino acid sequence of SEQ ID NO: 12.

45. The antibody or antigen-binding polypeptide thereof of claim 1, wherein the antibody or antigen-binding polypeptide thereof comprises a heavy chain variable domain that comprises the amino acid sequence of SEQ ID NO:1 and a light chain variable domain that comprises the amino acid sequence of SEQ ID NO: 11.

46. The antibody or antigen-binding polypeptide thereof of claim 1, wherein the light chain variable domain comprises an amino acid sequence of SEQ ID NO: 12.

* * * * *